(12) United States Patent
Shelton, IV et al.

(10) Patent No.: US 10,357,246 B2
(45) Date of Patent: Jul. 23, 2019

(54) ROTARY POWERED SURGICAL INSTRUMENT WITH MANUALLY ACTUATABLE BAILOUT SYSTEM

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 533 days.

(21) Appl. No.: 15/089,262

(22) Filed: Apr. 1, 2016

(65) Prior Publication Data
US 2017/0281161 A1    Oct. 5, 2017

(51) Int. Cl.
*A61B 17/072*    (2006.01)
*A61B 17/00*     (2006.01)
(Continued)

(52) U.S. Cl.
CPC ...... *A61B 17/072* (2013.01); *A61B 17/07207* (2013.01); *A61B 2017/00017* (2013.01);
(Continued)

(58) Field of Classification Search
CPC ............ A61B 17/072; A61B 17/07207; A61B 2017/00407; A61B 2017/2923;
(Continued)

(56) References Cited

U.S. PATENT DOCUMENTS 2,224,882 A    12/1940  Peck
2,742,955 A     4/1956  Dominguez
(Continued)

FOREIGN PATENT DOCUMENTS

AU    2008207624 A1    3/2009
AU    2010214687 A1    9/2010
(Continued)

OTHER PUBLICATIONS

Disclosed Anonymously, "Motor-Driven Surgical Stapler Improvements," Research Disclosure Database No. 526041, Published: Feb. 2008.
(Continued)

*Primary Examiner* — Alexander M Valvis
*Assistant Examiner* — Mobeen Ahmed

(57) ABSTRACT

A motor-driven surgical instrument is disclosed. The surgical instrument comprises a motor that is supported in a housing and includes at least one rotary drive system that is configured for selective operable engagement and disengagement with the motor assembly. A bailout drive train is supported by the housing assembly and is configured for selective operable engagement and disengagement with the at least one rotary drive system. A bailout handle assembly is selectively movable between a stored position within the housing assembly and an actuation position such that, when the bailout handle assembly is in the stored position, the at least one rotary drive system is retained in operable engagement with the motor assembly and when the bailout handle assembly is in the actuation position, the bailout drive train is in operable engagement with the at least one rotary drive system.

18 Claims, 36 Drawing Sheets

(51) Int. Cl.
*A61B 17/29* (2006.01)
*A61B 90/00* (2016.01)
(52) U.S. Cl.
CPC ............ *A61B 2017/00115* (2013.01); *A61B 2017/00123* (2013.01); *A61B 2017/00367* (2013.01); *A61B 2017/00398* (2013.01); *A61B 2017/00407* (2013.01); *A61B 2017/00464* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/291* (2013.01); *A61B 2017/2912* (2013.01); *A61B 2017/2922* (2013.01); *A61B 2017/2923* (2013.01); *A61B 2017/2927* (2013.01); *A61B 2017/2932* (2013.01); *A61B 2090/034* (2016.02)
(58) Field of Classification Search
CPC .... A61B 2017/2922; A61B 2017/2912; A61B 2017/291; A61B 2017/07278; A61B 2017/00734; A61B 2017/00464; A61B 2090/034; A61B 2017/00367; A61B 2017/00115; A61B 2017/00017; A61B 2017/2927; A61B 2017/07285; A61B 2017/07271; A61B 2017/07257; A61B 2017/00398; A61B 2017/00123; A61B 2017/2932
See application file for complete search history.

(56) References Cited

U.S. PATENT DOCUMENTS

| | | |
|---|---|---|
| 2,853,074 A | 9/1958 | Olson |
| 3,080,564 A | 3/1963 | Strekopitov et al. |
| 3,166,072 A | 1/1965 | Sullivan, Jr. |
| 3,266,494 A | 8/1966 | Brownrigg et al. |
| 3,359,978 A | 12/1967 | Smith, Jr. |
| 3,490,675 A | 1/1970 | Green et al. |
| 3,494,533 A | 2/1970 | Green et al. |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,744,495 A | 7/1973 | Johnson |
| 3,746,002 A | 7/1973 | Haller |
| 3,819,100 A | 6/1974 | Noiles et al. |
| 3,863,639 A | 2/1975 | Kleaveland |
| RE28,932 E | 8/1976 | Noiles et al. |
| 4,111,206 A | 9/1978 | Vishnevsky et al. |
| 4,190,042 A | 2/1980 | Sinnreich |
| 4,198,982 A | 4/1980 | Fortner et al. |
| 4,207,898 A | 6/1980 | Becht |
| 4,272,002 A | 6/1981 | Moshofsky |
| 4,274,398 A | 6/1981 | Scott, Jr. |
| 4,304,236 A | 12/1981 | Conta et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,408,692 A | 10/1983 | Sigel et al. |
| 4,415,112 A | 11/1983 | Green |
| 4,417,890 A | 11/1983 | Dennehey et al. |
| 4,429,695 A | 2/1984 | Green |
| 4,473,077 A | 9/1984 | Noiles et al. |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |
| 4,573,468 A | 3/1986 | Conta et al. |
| 4,573,622 A | 3/1986 | Green et al. |
| 4,580,712 A | 4/1986 | Green |
| 4,585,153 A | 4/1986 | Failla et al. |
| 4,605,004 A | 8/1986 | Di Giovanni et al. |
| 4,610,383 A | 9/1986 | Rothfuss et al. |
| 4,619,262 A | 10/1986 | Taylor |
| 4,619,391 A | 10/1986 | Sharkany et al. |
| 4,629,107 A | 12/1986 | Fedotov et al. |
| 4,632,290 A | 12/1986 | Green et al. |
| 4,654,028 A | 3/1987 | Suma |
| 4,655,222 A | 4/1987 | Florez et al. |
| 4,662,555 A | 5/1987 | Thornton |
| 4,664,305 A | 5/1987 | Blake, III et al. |
| 4,669,647 A | 6/1987 | Storace |
| 4,671,445 A | 6/1987 | Barker et al. |
| 4,684,051 A | 8/1987 | Akopov et al. |
| 4,700,703 A | 10/1987 | Resnick et al. |
| 4,715,520 A | 12/1987 | Roehr, Jr. et al. |
| 4,728,020 A | 3/1988 | Green et al. |
| 4,744,363 A | 5/1988 | Hasson |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,848,637 A | 7/1989 | Pruitt |
| 4,869,414 A | 9/1989 | Green et al. |
| 4,869,415 A | 9/1989 | Fox |
| 4,873,977 A | 10/1989 | Avant et al. |
| 4,892,244 A | 1/1990 | Fox et al. |
| 4,893,622 A | 1/1990 | Green et al. |
| 4,903,697 A | 2/1990 | Resnick et al. |
| 4,909,789 A | 3/1990 | Taguchi et al. |
| 4,921,479 A | 5/1990 | Grayzel |
| 4,930,674 A | 6/1990 | Barak |
| 4,941,623 A | 7/1990 | Pruitt |
| 4,944,443 A | 7/1990 | Oddsen et al. |
| 4,973,302 A | 11/1990 | Armour et al. |
| 4,984,564 A | 1/1991 | Yuen |
| 5,002,553 A | 3/1991 | Shiber |
| 5,014,899 A | 5/1991 | Presty et al. |
| 5,027,834 A | 7/1991 | Pruitt |
| 5,065,929 A | 11/1991 | Schulze et al. |
| 5,071,430 A | 12/1991 | de Salis et al. |
| 5,074,454 A | 12/1991 | Peters |
| 5,080,088 A | 1/1992 | LeVahn |
| 5,082,005 A | 1/1992 | Kaldany |
| 5,084,057 A | 1/1992 | Green et al. |
| 5,104,025 A | 4/1992 | Main et al. |
| 5,104,397 A | 4/1992 | Vasconcelos et al. |
| 5,108,368 A | 4/1992 | Hammerslag et al. |
| 5,116,349 A | 5/1992 | Aranyi |
| 5,119,983 A | 6/1992 | Green et al. |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,609 A | 10/1992 | Nakao et al. |
| 5,158,567 A | 10/1992 | Green |
| 5,171,247 A | 12/1992 | Hughett et al. |
| 5,171,249 A | 12/1992 | Stefanchik et al. |
| 5,195,505 A | 3/1993 | Josefsen |
| 5,197,649 A | 3/1993 | Bessler et al. |
| 5,205,459 A | 4/1993 | Brinkerhoff et al. |
| 5,211,649 A | 5/1993 | Kohler et al. |
| 5,211,655 A | 5/1993 | Hasson |
| 5,221,036 A | 6/1993 | Takase |
| 5,222,945 A | 6/1993 | Basnight |
| 5,222,963 A | 6/1993 | Brinkerhoff et al. |

(56) References Cited

U.S. PATENT DOCUMENTS

| | | |
|---|---|---|
| 5,222,975 A | 6/1993 | Crainich |
| 5,234,447 A | 8/1993 | Kaster et al. |
| 5,236,440 A | 8/1993 | Hlavacek |
| 5,239,981 A | 8/1993 | Anapliotis |
| 5,258,009 A | 11/1993 | Conners |
| 5,263,937 A | 11/1993 | Shipp |
| 5,271,543 A | 12/1993 | Grant et al. |
| 5,275,322 A | 1/1994 | Brinkerhoff et al. |
| 5,282,806 A | 2/1994 | Haber et al. |
| 5,282,829 A | 2/1994 | Hermes |
| 5,285,945 A | 2/1994 | Brinkerhoff et al. |
| 5,304,204 A | 4/1994 | Bregen |
| 5,309,896 A | 5/1994 | Moll et al. |
| 5,309,927 A | 5/1994 | Welch |
| 5,312,023 A | 5/1994 | Green et al. |
| 5,314,445 A | 5/1994 | Heidmueller nee Degwitz et al. |
| 5,330,502 A | 7/1994 | Hassler et al. |
| 5,333,772 A | 8/1994 | Rothfuss et al. |
| 5,336,232 A | 8/1994 | Green et al. |
| 5,342,385 A | 8/1994 | Norelli et al. |
| 5,342,395 A | 8/1994 | Jarrett et al. |
| 5,342,396 A | 8/1994 | Cook |
| 5,346,115 A | 9/1994 | Perouse et al. |
| 5,350,104 A | 9/1994 | Main et al. |
| 5,350,400 A | 9/1994 | Esposito et al. |
| 5,354,250 A | 10/1994 | Christensen |
| 5,354,303 A | 10/1994 | Spaeth et al. |
| 5,358,506 A | 10/1994 | Green et al. |
| 5,366,479 A | 11/1994 | McGarry et al. |
| 5,374,277 A | 12/1994 | Hassler |
| 5,375,588 A | 12/1994 | Yoon |
| 5,383,880 A | 1/1995 | Hooven |
| 5,383,888 A | 1/1995 | Zvenyatsky et al. |
| 5,383,895 A | 1/1995 | Holmes et al. |
| 5,391,180 A | 2/1995 | Tovey et al. |
| 5,395,030 A | 3/1995 | Kuramoto et al. |
| 5,395,033 A | 3/1995 | Byrne et al. |
| 5,395,384 A | 3/1995 | Duthoit et al. |
| 5,397,324 A | 3/1995 | Carroll et al. |
| 5,403,312 A | 4/1995 | Yates et al. |
| 5,404,870 A | 4/1995 | Brinkerhoff et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,411,508 A | 5/1995 | Bessler et al. |
| 5,413,267 A | 5/1995 | Solyntjes et al. |
| 5,413,272 A | 5/1995 | Green et al. |
| 5,413,573 A | 5/1995 | Koivukangas |
| 5,415,334 A | 5/1995 | Williamson et al. |
| 5,417,361 A | 5/1995 | Williamson, IV |
| 5,419,766 A | 5/1995 | Chang et al. |
| 5,425,745 A | 6/1995 | Green et al. |
| 5,433,721 A | 7/1995 | Hooven et al. |
| 5,441,494 A | 8/1995 | Ortiz |
| 5,445,644 A | 8/1995 | Pietrafitta et al. |
| 5,449,365 A | 9/1995 | Green et al. |
| 5,452,836 A | 9/1995 | Huitema et al. |
| 5,452,837 A | 9/1995 | Williamson, IV et al. |
| 5,458,279 A | 10/1995 | Plyley |
| 5,462,215 A | 10/1995 | Viola et al. |
| 5,465,894 A | 11/1995 | Clark et al. |
| 5,470,006 A | 11/1995 | Rodak |
| 5,470,009 A | 11/1995 | Rodak |
| 5,474,057 A | 12/1995 | Makower et al. |
| 5,474,566 A | 12/1995 | Alesi et al. |
| 5,476,479 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,490,819 A | 2/1996 | Nicholas et al. |
| 5,497,933 A | 3/1996 | DeFonzo et al. |
| 5,503,320 A | 4/1996 | Webster et al. |
| 5,503,635 A | 4/1996 | Sauer et al. |
| 5,505,363 A | 4/1996 | Green et al. |
| 5,507,426 A | 4/1996 | Young et al. |
| 5,509,596 A | 4/1996 | Green et al. |
| 5,511,564 A | 4/1996 | Wilk |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,678 A | 5/1996 | Heckele et al. |
| 5,520,700 A | 5/1996 | Beyar et al. |
| 5,527,264 A | 6/1996 | Moll et al. |
| 5,529,235 A | 6/1996 | Boiarski et al. |
| 5,531,856 A | 7/1996 | Moll et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,549,621 A | 8/1996 | Bessler et al. |
| 5,549,637 A | 8/1996 | Crainich |
| 5,551,622 A | 9/1996 | Yoon |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,571,116 A | 11/1996 | Bolanos et al. |
| 5,571,285 A | 11/1996 | Chow et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,613,937 A | 3/1997 | Garrison et al. |
| 5,615,820 A | 4/1997 | Viola |
| 5,618,303 A | 4/1997 | Marlow et al. |
| 5,618,307 A | 4/1997 | Donlon et al. |
| 5,620,452 A | 4/1997 | Yoon |
| 5,624,452 A | 4/1997 | Yates |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |

(56) References Cited

U.S. PATENT DOCUMENTS

| | | |
|---|---|---|
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,651,762 A | 7/1997 | Bridges |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,685,826 A | 11/1997 | Bonutti |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,408 A | 12/1997 | Wales et al. |
| 5,702,409 A | 12/1997 | Rayburn et al. |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,359 A | 2/1998 | Palmer et al. |
| 5,718,360 A | 2/1998 | Green et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,874 A | 4/1998 | Measamer et al. |
| 5,738,629 A | 4/1998 | Moll et al. |
| 5,741,271 A | 4/1998 | Nakao et al. |
| 5,743,456 A | 4/1998 | Jones et al. |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,752,970 A | 5/1998 | Yoon |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,859 A | 7/1998 | Nicholas et al. |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,797,959 A | 8/1998 | Castro et al. |
| 5,799,857 A | 9/1998 | Robertson et al. |
| 5,807,376 A | 9/1998 | Viola et al. |
| 5,807,378 A | 9/1998 | Jensen et al. |
| 5,810,721 A | 9/1998 | Mueller et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,817,084 A | 10/1998 | Jensen |
| 5,817,093 A | 10/1998 | Williamson, IV et al. |
| 5,820,009 A | 10/1998 | Melling et al. |
| 5,826,776 A | 10/1998 | Schulze et al. |
| 5,827,298 A | 10/1998 | Hart et al. |
| 5,829,662 A | 11/1998 | Allen et al. |
| 5,833,695 A | 11/1998 | Yoon |
| 5,836,503 A | 11/1998 | Ehrenfels et al. |
| 5,839,369 A | 11/1998 | Chatterjee et al. |
| 5,839,639 A | 11/1998 | Sauer et al. |
| 5,843,096 A | 12/1998 | Igaki et al. |
| 5,855,311 A | 1/1999 | Hamblin et al. |
| 5,855,583 A | 1/1999 | Wang et al. |
| 5,860,581 A | 1/1999 | Robertson et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,876,401 A | 3/1999 | Schulze et al. |
| 5,878,937 A | 3/1999 | Green et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,902,312 A | 5/1999 | Frater et al. |
| 5,906,577 A | 5/1999 | Beane et al. |
| 5,906,625 A | 5/1999 | Bito et al. |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,947,984 A | 9/1999 | Whipple |
| 5,951,576 A | 9/1999 | Wakabayashi |
| 5,954,259 A | 9/1999 | Viola et al. |
| 5,964,774 A | 10/1999 | McKean et al. |
| 5,997,528 A | 12/1999 | Bisch et al. |
| 5,997,552 A | 12/1999 | Person et al. |
| 6,003,517 A | 12/1999 | Sheffield et al. |
| 6,010,054 A | 1/2000 | Johnson et al. |
| 6,017,356 A | 1/2000 | Frederick et al. |
| 6,024,741 A | 2/2000 | Williamson, IV et al. |
| 6,024,748 A | 2/2000 | Manzo et al. |
| 6,032,849 A * | 3/2000 | Mastri ............ A61B 17/07207 227/176.1 |
| 6,045,560 A | 4/2000 | McKean et al. |
| 6,050,472 A | 4/2000 | Shibata |
| 6,053,390 A | 4/2000 | Green et al. |
| RE36,720 E | 5/2000 | Green et al. |
| 6,056,735 A | 5/2000 | Okada et al. |
| 6,063,025 A | 5/2000 | Bridges et al. |
| 6,063,097 A | 5/2000 | Oi et al. |
| 6,066,132 A | 5/2000 | Chen et al. |
| 6,074,401 A | 6/2000 | Gardiner et al. |

(56) References Cited

U.S. PATENT DOCUMENTS

| | | | |
|---|---|---|---|
| 6,079,606 A | 6/2000 | Milliman et al. |
| 6,083,234 A | 7/2000 | Nicholas et al. |
| 6,083,241 A | 7/2000 | Longo et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| H1904 H | 10/2000 | Yates et al. |
| 6,126,058 A | 10/2000 | Adams et al. |
| 6,131,790 A | 10/2000 | Piraka |
| 6,142,933 A | 11/2000 | Longo et al. |
| 6,155,473 A | 12/2000 | Tompkins et al. |
| 6,159,146 A | 12/2000 | El Gazayerli |
| 6,159,200 A | 12/2000 | Verdura et al. |
| 6,162,208 A | 12/2000 | Hipps |
| 6,165,188 A | 12/2000 | Saadat et al. |
| 6,171,330 B1 | 1/2001 | Benchetrit |
| 6,174,318 B1 | 1/2001 | Bates et al. |
| 6,179,195 B1 | 1/2001 | Adams et al. |
| 6,193,129 B1 | 2/2001 | Bittner et al. |
| 6,202,914 B1 | 3/2001 | Geiste et al. |
| 6,214,020 B1 | 4/2001 | Mulhauser et al. |
| 6,214,028 B1 | 4/2001 | Yoon et al. |
| 6,216,698 B1 | 4/2001 | Regula |
| 6,221,007 B1 | 4/2001 | Green |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,248,117 B1 | 6/2001 | Blatter |
| 6,250,532 B1 | 6/2001 | Green et al. |
| 6,254,534 B1 | 7/2001 | Butler et al. |
| 6,258,107 B1 | 7/2001 | Balazs et al. |
| 6,264,086 B1 | 7/2001 | McGuckin, Jr. |
| 6,264,087 B1 | 7/2001 | Whitman |
| 6,267,772 B1 | 7/2001 | Mulhauser et al. |
| 6,273,897 B1 | 8/2001 | Dalessandro et al. |
| 6,293,927 B1 | 9/2001 | McGuckin, Jr. |
| 6,302,311 B1 | 10/2001 | Adams et al. |
| 6,309,403 B1 | 10/2001 | Minor et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,364,888 B1 | 4/2002 | Niemeyer et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| RE37,814 E | 8/2002 | Allgeyer |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,523 B1 | 9/2002 | Middleman et al. |
| 6,450,391 B1 | 9/2002 | Kayan et al. |
| 6,458,077 B1 | 10/2002 | Boebel et al. |
| 6,478,210 B2 | 11/2002 | Adams et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,701 B2 | 12/2002 | Tierney et al. |
| 6,494,885 B1 | 12/2002 | Dhindsa |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,543,456 B1 | 4/2003 | Freeman |
| 6,551,333 B2 | 4/2003 | Kuhns et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,585,144 B2 | 7/2003 | Adams et al. |
| 6,588,643 B2 | 7/2003 | Bolduc et al. |
| 6,592,597 B2 | 7/2003 | Grant et al. |
| 6,601,749 B2 | 8/2003 | Sullivan et al. |
| 6,605,078 B2 | 8/2003 | Adams |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,285 B2 | 10/2003 | Gabbay |
| 6,638,297 B1 | 10/2003 | Huitema |
| 6,644,532 B2 | 11/2003 | Green et al. |
| 6,645,201 B1 | 11/2003 | Utley et al. |
| 6,648,901 B2 | 11/2003 | Fleischman et al. |
| 6,656,193 B2 | 12/2003 | Grant et al. |
| 6,666,854 B1 | 12/2003 | Lange |
| 6,669,073 B2 | 12/2003 | Milliman et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,726,697 B2 | 4/2004 | Nicholas et al. |
| 6,736,825 B2 | 5/2004 | Blatter et al. |
| 6,749,600 B1 | 6/2004 | Levy |
| 6,752,816 B2 | 6/2004 | Culp et al. |
| 6,755,338 B2 | 6/2004 | Hahnen et al. |
| 6,769,590 B2 | 8/2004 | Vresh et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,820,791 B2 | 11/2004 | Adams |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,830,174 B2 | 12/2004 | Hillstead et al. |
| 6,835,199 B2 | 12/2004 | McGuckin, Jr. et al. |
| 6,840,423 B2 | 1/2005 | Adams et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,913,608 B2 | 7/2005 | Liddicoat et al. |
| 6,913,613 B2 | 7/2005 | Schwarz et al. |
| 6,936,042 B2 | 8/2005 | Wallace et al. |

(56) References Cited

U.S. PATENT DOCUMENTS

| | | |
|---|---|---|
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,220 B2 | 11/2005 | Marino et al. |
| 6,964,363 B2 | 11/2005 | Wales et al. |
| 6,971,988 B2 | 12/2005 | Orban, III |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,032,798 B2 | 4/2006 | Whitman et al. |
| 7,032,799 B2 | 4/2006 | Viola et al. |
| 7,037,314 B2 | 5/2006 | Armstrong |
| 7,044,352 B2 | 5/2006 | Shelton, IV et al. |
| 7,044,353 B2 | 5/2006 | Mastri et al. |
| 7,052,454 B2 | 5/2006 | Taylor |
| 7,055,731 B2 | 6/2006 | Shelton, IV et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,083,626 B2 | 8/2006 | Hart et al. |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,247 B2 | 8/2006 | Monassevitch et al. |
| 7,097,089 B2 | 8/2006 | Marczyk |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,134,587 B2 | 11/2006 | Schwemberger et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,147,139 B2 | 12/2006 | Schwemberger et al. |
| 7,147,650 B2 | 12/2006 | Lee |
| 7,156,863 B2 | 1/2007 | Sonnenschein et al. |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,229,408 B2 | 6/2007 | Douglas et al. |
| 7,234,624 B2 | 6/2007 | Gresham et al. |
| 7,235,089 B1 | 6/2007 | McGuckin, Jr. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,252,660 B2 | 8/2007 | Kunz |
| 7,258,262 B2 | 8/2007 | Mastri et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,334,718 B2 | 2/2008 | McAlister et al. |
| 7,338,505 B2 | 3/2008 | Belson |
| 7,338,513 B2 | 3/2008 | Lee et al. |
| 7,343,920 B2 | 3/2008 | Toby et al. |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |

(56) References Cited

U.S. PATENT DOCUMENTS

| | | |
|---|---|---|
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,641,091 B2 | 1/2010 | Olson et al. |
| 7,641,092 B2 | 1/2010 | Kruszynski et al. |
| 7,641,095 B2 | 1/2010 | Viola |
| 7,644,848 B2 | 1/2010 | Swayze et al. |
| 7,648,519 B2 | 1/2010 | Lee et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,686 B2 | 3/2010 | Curro et al. |
| 7,686,201 B2 | 3/2010 | Csiky |
| 7,686,826 B2 | 3/2010 | Lee et al. |
| 7,691,098 B2 | 4/2010 | Wallace et al. |
| 7,694,864 B2 | 4/2010 | Okada et al. |
| 7,694,865 B2 | 4/2010 | Scirica |
| 7,699,204 B2 | 4/2010 | Viola |
| 7,699,844 B2 | 4/2010 | Utley et al. |
| 7,699,859 B2 | 4/2010 | Bombard et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,873 B2 | 5/2010 | Swick |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,736,306 B2 | 6/2010 | Brustad et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,426 B2 | 11/2010 | Racenet et al. |
| 7,828,189 B2 | 11/2010 | Holsten et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,534 B2 | 12/2010 | Viola et al. |

(56) References Cited

U.S. PATENT DOCUMENTS

| | | |
|---|---|---|
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,862,502 B2 | 1/2011 | Pool et al. |
| 7,866,525 B2 | 1/2011 | Scirica |
| 7,866,527 B2 | 1/2011 | Hall et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,461 B2 | 2/2011 | Albrecht et al. |
| 7,886,952 B2 | 2/2011 | Scirica et al. |
| 7,891,531 B1 | 2/2011 | Ward |
| 7,891,532 B2 | 2/2011 | Mastri et al. |
| 7,896,214 B2 | 3/2011 | Farascioni |
| 7,896,215 B2 | 3/2011 | Adams et al. |
| 7,896,897 B2 | 3/2011 | Gresham et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,963,433 B2 | 6/2011 | Whitman et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,791 B2 | 6/2011 | Franer et al. |
| 7,980,443 B2 | 7/2011 | Scheib et al. |
| 7,981,132 B2 | 7/2011 | Dubrul et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,469 B2 | 8/2011 | Olson et al. |
| 8,002,696 B2 | 8/2011 | Suzuki |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,021,389 B2 | 9/2011 | Molz, IV |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,043,207 B2 | 10/2011 | Adams |
| 8,043,328 B2 | 10/2011 | Hahnen et al. |
| 8,056,787 B2 | 11/2011 | Boudreaux et al. |
| 8,056,788 B2 | 11/2011 | Mastri et al. |
| 8,061,558 B2 | 11/2011 | Jordan et al. |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,075,476 B2 | 12/2011 | Vargas |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,096,457 B1 | 1/2012 | Manoux et al. |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,767 B2 | 2/2012 | Bauman et al. |
| 8,127,975 B2 | 3/2012 | Olson et al. |
| 8,128,559 B2 | 3/2012 | Minnelli |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,141,762 B2 | 3/2012 | Bedi et al. |
| 8,141,763 B2 | 3/2012 | Milliman |
| 8,146,790 B2 | 4/2012 | Milliman |
| 8,147,456 B2 | 4/2012 | Fisher et al. |
| 8,152,041 B2 | 4/2012 | Kostrzewski |
| 8,152,773 B2 | 4/2012 | Albrecht et al. |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,215,531 B2 | 7/2012 | Shelton, IV et al. |
| 8,215,533 B2 | 7/2012 | Viola et al. |

(56) References Cited

U.S. PATENT DOCUMENTS

| | | |
|---|---|---|
| 8,220,688 B2 | 7/2012 | Laurent et al. |
| 8,220,690 B2 | 7/2012 | Hess et al. |
| 8,225,799 B2 | 7/2012 | Bettuchi |
| 8,226,553 B2 | 7/2012 | Shelton, IV et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,189 B2 | 10/2012 | Fisher et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,638 B2 | 11/2012 | Hart |
| 8,313,496 B2 | 11/2012 | Sauer et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,333,691 B2 | 12/2012 | Schaaf |
| 8,336,753 B2 | 12/2012 | Olson et al. |
| 8,337,517 B2 | 12/2012 | Van Dalen |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,669 B2 | 3/2013 | Kim |
| 8,403,198 B2 | 3/2013 | Sorrentino et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,740 B2 | 4/2013 | Shelton, IV et al. |
| 8,424,741 B2 | 4/2013 | McGuckin, Jr. et al. |
| 8,439,246 B1 | 5/2013 | Knodel |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,515 B2 | 6/2013 | Drew et al. |
| 8,474,677 B2 | 7/2013 | Woodard, Jr. et al. |
| 8,475,457 B2 | 7/2013 | Shano |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,485,414 B2 | 7/2013 | Criscuolo et al. |
| 8,485,970 B2 | 7/2013 | Widenhouse et al. |
| 8,490,853 B2 | 7/2013 | Criscuolo et al. |
| 8,491,603 B2 | 7/2013 | Yeung et al. |
| 8,496,156 B2 | 7/2013 | Sniffin et al. |
| 8,499,993 B2 | 8/2013 | Shelton, IV et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,931 B2 | 8/2013 | Minnelli et al. |
| 8,523,043 B2 | 9/2013 | Ullrich et al. |
| 8,523,881 B2 | 9/2013 | Cabiri et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,603,089 B2 | 12/2013 | Viola |
| 8,608,043 B2 | 12/2013 | Scirica |
| 8,608,044 B2 | 12/2013 | Hueil et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter et al. |
| 8,627,993 B2 | 1/2014 | Smith et al. |
| 8,627,995 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |

(56) References Cited

U.S. PATENT DOCUMENTS

| | | |
|---|---|---|
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,640,788 B2 | 2/2014 | Dachs, II et al. |
| 8,640,940 B2 | 2/2014 | Ohdaira |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,839 B2 | 3/2014 | Ewers et al. |
| 8,672,951 B2 | 3/2014 | Smith et al. |
| 8,679,154 B2 | 3/2014 | Smith et al. |
| 8,679,156 B2 | 3/2014 | Smith et al. |
| 8,684,253 B2 | 4/2014 | Giordano et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,213 B2 | 4/2014 | Shelton, IV et al. |
| 8,714,429 B2 | 5/2014 | Demmy |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,961 B2 | 5/2014 | Ziv |
| 8,733,612 B2 | 5/2014 | Ma |
| 8,733,613 B2 | 5/2014 | Huitema et al. |
| 8,734,336 B2 | 5/2014 | Bonadio et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,773 B2 | 7/2014 | Harari et al. |
| 8,770,458 B2 | 7/2014 | Scirica |
| 8,770,459 B2 | 7/2014 | Racenet et al. |
| 8,770,460 B2 | 7/2014 | Belzer |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,814,788 B2 | 8/2014 | Gan |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,834,464 B2 | 9/2014 | Stewart et al. |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,888,695 B2 | 11/2014 | Piskun et al. |
| 8,893,946 B2 | 11/2014 | Boudreaux et al. |
| 8,893,949 B2 | 11/2014 | Shelton, IV et al. |
| 8,899,462 B2 | 12/2014 | Kostrzewski et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,910,847 B2 | 12/2014 | Nalagatla et al. |
| 8,911,471 B2 | 12/2014 | Spivey et al. |
| 8,920,435 B2 | 12/2014 | Smith et al. |
| 8,925,782 B2 | 1/2015 | Shelton, IV |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,682 B2 | 1/2015 | Timm et al. |
| 8,955,732 B2 | 2/2015 | Zemlok et al. |
| 8,956,390 B2 | 2/2015 | Shah et al. |
| 8,960,519 B2 | 2/2015 | Whitman et al. |
| 8,967,448 B2 | 3/2015 | Carter et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,005,243 B2 | 4/2015 | Stopek et al. |
| 9,016,541 B2 | 4/2015 | Viola et al. |
| 9,016,542 B2 | 4/2015 | Shelton, IV et al. |
| 9,028,494 B2 | 5/2015 | Shelton, IV et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,120 B2 | 6/2015 | Swarup et al. |
| 9,055,941 B2 | 6/2015 | Schmid et al. |
| 9,055,942 B2 | 6/2015 | Balbierz et al. |
| 9,055,945 B2 | 6/2015 | Miksza et al. |
| 9,060,770 B2 | 6/2015 | Shelton, IV et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |

(56) References Cited

U.S. PATENT DOCUMENTS

| | | |
|---|---|---|
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,957 B2 | 9/2015 | Gantz et al. |
| 9,125,654 B2 | 9/2015 | Aronhalt et al. |
| 9,125,662 B2 | 9/2015 | Shelton, IV |
| 9,131,835 B2 | 9/2015 | Widenhouse et al. |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,173,978 B2 | 11/2015 | Kelly et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,186,148 B2 | 11/2015 | Felder et al. |
| 9,198,661 B2 | 12/2015 | Swensgard |
| 9,198,662 B2 | 12/2015 | Barton et al. |
| 9,204,830 B2 | 12/2015 | Zand et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,463 B2 | 3/2016 | Viola et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,812 B2 | 5/2016 | Waaler et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,082 B2 | 5/2016 | Wei et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,351,734 B2 | 5/2016 | Prior |
| 9,358,003 B2 | 6/2016 | Hall et al. |
| 9,358,005 B2 | 6/2016 | Shelton, IV et al. |
| 9,364,217 B2 | 6/2016 | Kostrzewski et al. |
| 9,364,219 B2 | 6/2016 | Olson et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,427,223 B2 | 8/2016 | Park et al. |
| 9,433,419 B2 | 9/2016 | Gonzalez et al. |
| 9,439,649 B2 | 9/2016 | Shelton, IV et al. |
| 9,439,651 B2 | 9/2016 | Smith et al. |
| 9,451,958 B2 | 9/2016 | Shelton, IV et al. |
| 9,451,980 B2 | 9/2016 | Alfieri |
| 9,463,260 B2 | 10/2016 | Stopek |
| 9,468,438 B2 | 10/2016 | Baber et al. |
| 9,474,519 B2 | 10/2016 | Brustad et al. |
| 9,480,476 B2 | 11/2016 | Aldridge et al. |
| 9,486,132 B2 | 11/2016 | Green |
| 9,486,200 B2 | 11/2016 | Melsheimer et al. |
| 9,486,213 B2 | 11/2016 | Altman et al. |
| 9,486,214 B2 | 11/2016 | Shelton, IV |
| 9,492,154 B2 | 11/2016 | Melsheimer et al. |
| 9,492,167 B2 | 11/2016 | Shelton, IV et al. |
| 9,492,170 B2 | 11/2016 | Bear et al. |
| 9,498,219 B2 | 11/2016 | Moore et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,549,732 B2 | 1/2017 | Yates et al. |
| 9,554,794 B2 | 1/2017 | Baber et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,572,573 B2 | 2/2017 | Scheib et al. |
| 9,572,574 B2 | 2/2017 | Shelton, IV et al. |
| 9,572,577 B2 | 2/2017 | Lloyd et al. |
| 9,585,550 B2 | 3/2017 | Abel et al. |
| 9,585,657 B2 | 3/2017 | Shelton, IV et al. |
| 9,585,660 B2 | 3/2017 | Laurent et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,615,826 B2 | 4/2017 | Shelton, IV et al. |
| 9,615,892 B2 | 4/2017 | Piferi et al. |
| 9,629,623 B2 | 4/2017 | Lytle, IV et al. |
| 9,629,626 B2 | 4/2017 | Soltz et al. |
| 9,629,631 B2 | 4/2017 | Nicholas et al. |
| 9,629,814 B2 | 4/2017 | Widenhouse et al. |
| 9,636,112 B2 | 5/2017 | Penna et al. |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,662,131 B2 | 5/2017 | Omori et al. |

(56) References Cited

U.S. PATENT DOCUMENTS

| | | |
|---|---|---|
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,236 B2 | 6/2017 | Leimbach et al. |
| 9,690,362 B2 | 6/2017 | Leimbach et al. |
| 9,693,777 B2 | 7/2017 | Schellin et al. |
| 9,700,309 B2 | 7/2017 | Jaworek et al. |
| 9,700,317 B2 | 7/2017 | Aronhalt et al. |
| 9,700,321 B2 | 7/2017 | Shelton, IV et al. |
| 9,700,326 B2 | 7/2017 | Morriss et al. |
| 9,706,991 B2 | 7/2017 | Hess et al. |
| 9,724,091 B2 | 8/2017 | Shelton, IV et al. |
| 9,724,094 B2 | 8/2017 | Baber et al. |
| 9,724,100 B2 | 8/2017 | Scheib et al. |
| 9,730,692 B2 | 8/2017 | Shelton, IV et al. |
| 9,733,663 B2 | 8/2017 | Leimbach et al. |
| 9,737,301 B2 | 8/2017 | Baber et al. |
| 9,737,335 B2 | 8/2017 | Butler et al. |
| 9,743,928 B2 | 8/2017 | Shelton, IV et al. |
| 9,743,929 B2 | 8/2017 | Leimbach et al. |
| 9,750,499 B2 | 9/2017 | Leimbach et al. |
| 9,750,502 B2 | 9/2017 | Scirica et al. |
| 9,750,503 B2 | 9/2017 | Milliman |
| 9,757,123 B2 | 9/2017 | Giordano et al. |
| 9,757,124 B2 | 9/2017 | Schellin et al. |
| 9,757,128 B2 | 9/2017 | Baber et al. |
| 9,757,130 B2 | 9/2017 | Shelton, IV |
| 9,757,133 B2 | 9/2017 | Latimer et al. |
| 9,770,245 B2 | 9/2017 | Swayze et al. |
| 9,775,608 B2 | 10/2017 | Aronhalt et al. |
| 9,775,613 B2 | 10/2017 | Shelton, IV et al. |
| 9,782,169 B2 | 10/2017 | Kimsey et al. |
| 9,788,834 B2 | 10/2017 | Schmid et al. |
| 9,788,836 B2 | 10/2017 | Overmyer et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,814,460 B2 | 11/2017 | Kimsey et al. |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,833,236 B2 | 12/2017 | Shelton, IV et al. |
| 9,833,241 B2 | 12/2017 | Huitema et al. |
| 9,839,420 B2 | 12/2017 | Shelton, IV et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,848,873 B2 | 12/2017 | Shelton, IV |
| 9,848,875 B2 | 12/2017 | Aronhalt et al. |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,872,684 B2 | 1/2018 | Hall et al. |
| 9,877,721 B2 | 1/2018 | Schellin et al. |
| 9,877,722 B2 | 1/2018 | Schellin et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,895,148 B2 | 2/2018 | Shelton, IV et al. |
| 9,901,342 B2 | 2/2018 | Shelton, IV et al. |
| 9,907,600 B2 | 3/2018 | Stulen et al. |
| 9,913,642 B2 | 3/2018 | Leimbach et al. |
| 9,913,646 B2 | 3/2018 | Shelton, IV |
| 9,918,704 B2 | 3/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,974,529 B2 | 5/2018 | Shelton, IV et al. |
| 9,980,713 B2 | 5/2018 | Aronhalt et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 10,004,497 B2 | 6/2018 | Overmyer et al. |
| 10,004,498 B2 | 6/2018 | Morgan et al. |
| 10,004,501 B2 | 6/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| 10,039,529 B2 | 8/2018 | Kerr et al. |
| 10,045,769 B2 | 8/2018 | Aronhalt et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,058,963 B2 | 8/2018 | Shelton, IV et al. |
| 10,064,621 B2 | 9/2018 | Kerr et al. |
| 10,071,452 B2 | 9/2018 | Shelton, IV et al. |
| 10,085,748 B2 | 10/2018 | Morgan et al. |
| 10,111,679 B2 | 10/2018 | Baber et al. |
| 10,117,649 B2 | 11/2018 | Baxter, III et al. |
| 10,123,798 B2 | 11/2018 | Baxter, III et al. |
| 10,130,352 B2 | 11/2018 | Widenhouse et al. |
| 10,130,359 B2 | 11/2018 | Hess et al. |
| 10,130,363 B2 | 11/2018 | Huitema et al. |
| 10,130,366 B2 | 11/2018 | Shelton, IV et al. |
| 10,135,242 B2 | 11/2018 | Baber et al. |
| 10,136,887 B2 | 11/2018 | Shelton, IV et al. |
| 10,136,890 B2 | 11/2018 | Shelton, IV et al. |
| 10,136,891 B2 | 11/2018 | Shelton, IV et al. |
| 10,149,680 B2 | 12/2018 | Parihar et al. |
| 10,149,682 B2 | 12/2018 | Shelton, IV et al. |
| 2001/0025183 A1 | 9/2001 | Shahidi |
| 2002/0095175 A1 | 7/2002 | Brock et al. |
| 2002/0103494 A1 | 8/2002 | Pacey |
| 2002/0117534 A1 | 8/2002 | Green et al. |
| 2003/0190584 A1 | 10/2003 | Heasley |
| 2004/0054353 A1 | 3/2004 | Taylor |
| 2004/0098040 A1 | 5/2004 | Taniguchi et al. |
| 2004/0108357 A1 | 6/2004 | Milliman et al. |
| 2004/0147909 A1 | 7/2004 | Johnston et al. |
| 2004/0158230 A1 | 8/2004 | Hunn et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0254566 A1 | 12/2004 | Plicchi et al. |
| 2004/0260315 A1 | 12/2004 | Dell et al. |
| 2004/0267310 A1 | 12/2004 | Racenet et al. |
| 2005/0033226 A1 | 2/2005 | Kim |
| 2005/0051163 A1 | 3/2005 | Deem et al. |
| 2005/0059997 A1 | 3/2005 | Bauman et al. |
| 2005/0070929 A1 | 3/2005 | Dalessandro et al. |
| 2005/0085693 A1 | 4/2005 | Belson et al. |
| 2005/0131390 A1 | 6/2005 | Heinrich et al. |

(56) References Cited

U.S. PATENT DOCUMENTS

| | | |
|---|---|---|
| 2005/0131457 A1 | 6/2005 | Douglas et al. |
| 2005/0143756 A1 | 6/2005 | Jankowski |
| 2005/0143759 A1 | 6/2005 | Kelly |
| 2005/0154406 A1 | 7/2005 | Bombard et al. |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0203550 A1 | 9/2005 | Laufer et al. |
| 2005/0216055 A1 | 9/2005 | Scirica et al. |
| 2005/0236459 A1 | 10/2005 | Gresham |
| 2005/0245965 A1 | 11/2005 | Orban, III et al. |
| 2005/0246881 A1 | 11/2005 | Kelly et al. |
| 2005/0256452 A1 | 11/2005 | DeMarchi et al. |
| 2005/0263563 A1 | 12/2005 | Racenet et al. |
| 2005/0283188 A1 | 12/2005 | Loshakove et al. |
| 2006/0020258 A1 | 1/2006 | Strauss et al. |
| 2006/0025812 A1 | 2/2006 | Shelton |
| 2006/0041188 A1 | 2/2006 | Dirusso et al. |
| 2006/0049229 A1 | 3/2006 | Milliman et al. |
| 2006/0052669 A1 | 3/2006 | Hart |
| 2006/0052825 A1 | 3/2006 | Ransick et al. |
| 2006/0100643 A1 | 5/2006 | Laufer et al. |
| 2006/0149306 A1 | 7/2006 | Hart et al. |
| 2006/0161050 A1 | 7/2006 | Butler et al. |
| 2006/0161185 A1 | 7/2006 | Saadat et al. |
| 2006/0173470 A1 | 8/2006 | Oray et al. |
| 2006/0175375 A1* | 8/2006 | Shelton, IV ..... A61B 17/07207 227/176.1 |
| 2006/0180634 A1 | 8/2006 | Shelton et al. |
| 2006/0185682 A1 | 8/2006 | Marczyk |
| 2006/0201989 A1 | 9/2006 | Ojeda |
| 2006/0211919 A1 | 9/2006 | Wilk |
| 2006/0235368 A1 | 10/2006 | Oz |
| 2006/0241651 A1 | 10/2006 | Wilk |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2006/0289602 A1 | 12/2006 | Wales et al. |
| 2007/0027468 A1 | 2/2007 | Wales et al. |
| 2007/0043387 A1 | 2/2007 | Vargas et al. |
| 2007/0073341 A1 | 3/2007 | Smith et al. |
| 2007/0078484 A1 | 4/2007 | Talarico et al. |
| 2007/0080188 A1 | 4/2007 | Spence et al. |
| 2007/0080814 A1* | 4/2007 | Ellsworth ............ G08B 27/008 340/573.1 |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0135803 A1 | 6/2007 | Belson |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0208359 A1 | 9/2007 | Hoffman |
| 2007/0225562 A1 | 9/2007 | Spivey et al. |
| 2007/0244471 A1 | 10/2007 | Malackowski |
| 2007/0246505 A1 | 10/2007 | Pace-Floridia et al. |
| 2007/0276409 A1 | 11/2007 | Ortiz et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0190989 A1 | 8/2008 | Crews et al. |
| 2008/0197167 A1 | 8/2008 | Viola et al. |
| 2008/0200933 A1 | 8/2008 | Bakos et al. |
| 2008/0237298 A1* | 10/2008 | Schall .............. A61B 17/07207 227/180.1 |
| 2008/0242939 A1 | 10/2008 | Johnston |
| 2008/0255413 A1 | 10/2008 | Zemlok et al. |
| 2008/0262654 A1 | 10/2008 | Omori et al. |
| 2008/0294179 A1 | 11/2008 | Balbierz et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0012534 A1 | 1/2009 | Madhani et al. |
| 2009/0078736 A1 | 3/2009 | Van Lue |
| 2009/0090763 A1 | 4/2009 | Zemlok et al. |
| 2009/0149871 A9 | 6/2009 | Kagan et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206128 A1* | 8/2009 | Hueil ............... A61B 17/07207 227/175.2 |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0292283 A1 | 11/2009 | Odom |
| 2009/0308907 A1 | 12/2009 | Nalagatla et al. |
| 2010/0001036 A1* | 1/2010 | Marczyk .......... A61B 17/07207 227/175.1 |
| 2010/0069942 A1 | 3/2010 | Shelton, IV |
| 2010/0089970 A1* | 4/2010 | Smith ............... A61B 17/07207 227/175.1 |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2010/0292540 A1 | 11/2010 | Hess et al. |
| 2010/0312261 A1 | 12/2010 | Suzuki et al. |
| 2011/0006101 A1 | 1/2011 | Hall et al. |
| 2011/0011916 A1 | 1/2011 | Levine |
| 2011/0017801 A1* | 1/2011 | Zemlok ............ A61B 17/07207 227/175.1 |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0060363 A1 | 3/2011 | Hess et al. |
| 2011/0071356 A1 | 3/2011 | Edwards |
| 2011/0087276 A1 | 4/2011 | Bedi et al. |
| 2011/0114697 A1 | 5/2011 | Baxter, III et al. |
| 2011/0118706 A1 | 5/2011 | Gingras et al. |
| 2011/0125176 A1 | 5/2011 | Yates et al. |
| 2011/0147433 A1 | 6/2011 | Shelton, IV et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0295295 A1 | 12/2011 | Shelton, IV et al. |
| 2012/0029272 A1 | 2/2012 | Shelton, IV et al. |

(56) References Cited

U.S. PATENT DOCUMENTS

| | | |
|---|---|---|
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080477 A1* | 4/2012 | Leimbach ........ A61B 17/07207 227/175.2 |
| 2012/0080478 A1 | 4/2012 | Morgan et al. |
| 2012/0080498 A1 | 4/2012 | Shelton, IV et al. |
| 2012/0175398 A1 | 7/2012 | Sandborn et al. |
| 2012/0199602 A1 | 8/2012 | Jordan et al. |
| 2012/0234895 A1 | 9/2012 | O'Connor et al. |
| 2012/0234897 A1 | 9/2012 | Shelton, IV et al. |
| 2012/0241494 A1* | 9/2012 | Marczyk .......... A61B 17/07207 227/175.1 |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026209 A1 | 1/2013 | Mozdzierz et al. |
| 2013/0026210 A1 | 1/2013 | Shelton, IV et al. |
| 2013/0030253 A1 | 1/2013 | Titus |
| 2013/0085339 A1 | 4/2013 | Jaworek et al. |
| 2013/0087597 A1 | 4/2013 | Shelton, IV et al. |
| 2013/0098970 A1 | 4/2013 | Racenet et al. |
| 2013/0116669 A1 | 5/2013 | Shelton, IV et al. |
| 2013/0153636 A1 | 6/2013 | Shelton, IV et al. |
| 2013/0153641 A1 | 6/2013 | Shelton, IV et al. |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0214030 A1 | 8/2013 | Aronhalt et al. |
| 2013/0231667 A1 | 9/2013 | Taylor et al. |
| 2013/0233906 A1 | 9/2013 | Hess et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0270322 A1 | 10/2013 | Scheib et al. |
| 2013/0324981 A1 | 12/2013 | Smith et al. |
| 2013/0324982 A1 | 12/2013 | Smith et al. |
| 2013/0331867 A1 | 12/2013 | Reeser et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014704 A1* | 1/2014 | Onukuri ............. A61B 17/068 227/175.1 |
| 2014/0014705 A1 | 1/2014 | Baxter, III |
| 2014/0107640 A1 | 4/2014 | Yates et al. |
| 2014/0151433 A1 | 6/2014 | Shelton, IV et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0200561 A1 | 7/2014 | Ingmanson et al. |
| 2014/0224857 A1 | 8/2014 | Schmid |
| 2014/0239036 A1* | 8/2014 | Zerkle ............. A61B 17/07207 227/175.1 |
| 2014/0243865 A1 | 8/2014 | Swayze et al. |
| 2014/0246475 A1 | 9/2014 | Hall et al. |
| 2014/0249557 A1 | 9/2014 | Koch, Jr. et al. |
| 2014/0263539 A1* | 9/2014 | Leimbach ........ A61B 17/07207 227/175.1 |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0284371 A1 | 9/2014 | Morgan et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0309666 A1 | 10/2014 | Shelton, IV et al. |
| 2015/0053737 A1 | 2/2015 | Leimbach et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0280384 A1 | 10/2015 | Leimbach et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0313594 A1 | 11/2015 | Shelton, IV et al. |
| 2015/0351758 A1 | 12/2015 | Shelton, IV et al. |
| 2016/0066913 A1 | 3/2016 | Swayze et al. |
| 2016/0089146 A1 | 3/2016 | Harris et al. |
| 2016/0113653 A1 | 4/2016 | Zingman |
| 2016/0120544 A1 | 5/2016 | Shelton, IV et al. |
| 2016/0135796 A1 | 5/2016 | Hundertmark et al. |
| 2016/0143637 A1 | 5/2016 | Nering et al. |
| 2016/0174969 A1 | 6/2016 | Kerr et al. |
| 2016/0174972 A1 | 6/2016 | Shelton, IV et al. |
| 2016/0249909 A1 | 9/2016 | Shelton, IV et al. |
| 2016/0249910 A1 | 9/2016 | Shelton, IV et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249927 A1 | 9/2016 | Beckman et al. |
| 2016/0256071 A1 | 9/2016 | Shelton, IV et al. |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256185 A1 | 9/2016 | Shelton, IV et al. |
| 2016/0278775 A1 | 9/2016 | Shelton, IV et al. |
| 2016/0367245 A1 | 12/2016 | Wise et al. |
| 2016/0367246 A1 | 12/2016 | Baxter, III et al. |
| 2016/0367254 A1 | 12/2016 | Baxter, III et al. |
| 2016/0367255 A1 | 12/2016 | Wise et al. |
| 2016/0367256 A1 | 12/2016 | Hensel et al. |
| 2017/0007229 A1 | 1/2017 | Widenhouse et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055986 A1 | 3/2017 | Harris et al. |
| 2017/0056000 A1 | 3/2017 | Nalagatla et al. |
| 2017/0119386 A1 | 5/2017 | Scheib et al. |
| 2017/0119387 A1 | 5/2017 | Dalessandro et al. |
| 2017/0119389 A1 | 5/2017 | Turner et al. |
| 2017/0119390 A1 | 5/2017 | Schellin et al. |
| 2017/0119392 A1 | 5/2017 | Shelton, IV et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224333 A1 | 8/2017 | Hunter et al. |
| 2017/0224334 A1 | 8/2017 | Worthington et al. |
| 2017/0224335 A1 | 8/2017 | Weaner et al. |
| 2017/0224336 A1 | 8/2017 | Hunter et al. |
| 2017/0224342 A1 | 8/2017 | Worthington et al. |
| 2017/0224343 A1 | 8/2017 | Baxter, III et al. |

(56) References Cited

U.S. PATENT DOCUMENTS

| | | | |
|---|---|---|---|
| 2017/0231623 | A1 | 8/2017 | Shelton, IV et al. |
| 2017/0231626 | A1 | 8/2017 | Shelton, IV et al. |
| 2017/0231627 | A1 | 8/2017 | Shelton, IV et al. |
| 2017/0231628 | A1 | 8/2017 | Shelton, IV et al. |
| 2017/0258540 | A1 | 9/2017 | Blatt |
| 2017/0281155 | A1 | 10/2017 | Shelton, IV et al. |
| 2017/0281162 | A1 | 10/2017 | Shelton, IV et al. |
| 2017/0281163 | A1 | 10/2017 | Shelton, IV et al. |
| 2017/0281164 | A1 | 10/2017 | Harris et al. |
| 2017/0281165 | A1 | 10/2017 | Harris et al. |
| 2017/0281166 | A1 | 10/2017 | Morgan et al. |
| 2017/0281167 | A1 | 10/2017 | Shelton, IV et al. |
| 2017/0281168 | A1 | 10/2017 | Shelton, IV et al. |
| 2017/0281169 | A1 | 10/2017 | Harris et al. |
| 2017/0281170 | A1 | 10/2017 | Shelton, IV et al. |
| 2017/0281171 | A1* | 10/2017 | Shelton, IV ....... A61B 17/3211 |
| 2017/0281172 | A1 | 10/2017 | Shelton, IV et al. |
| 2017/0281173 | A1 | 10/2017 | Shelton, IV et al. |
| 2017/0281174 | A1 | 10/2017 | Harris et al. |
| 2017/0281177 | A1 | 10/2017 | Harris et al. |
| 2017/0281178 | A1 | 10/2017 | Shelton, IV et al. |
| 2017/0281179 | A1 | 10/2017 | Shelton, IV et al. |
| 2017/0281180 | A1 | 10/2017 | Morgan et al. |
| 2017/0281183 | A1 | 10/2017 | Miller et al. |
| 2017/0281184 | A1 | 10/2017 | Shelton, IV et al. |
| 2017/0281185 | A1 | 10/2017 | Miller et al. |
| 2017/0281186 | A1 | 10/2017 | Shelton, IV et al. |
| 2017/0281187 | A1 | 10/2017 | Shelton, IV et al. |
| 2017/0281188 | A1 | 10/2017 | Shelton, IV et al. |
| 2017/0281189 | A1 | 10/2017 | Nalagatla et al. |
| 2018/0325508 | A1 | 11/2018 | Aronhalt et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 2686539 Y | 3/2005 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101675898 A | 3/2010 |
| CN | 101683280 A | 3/2010 |
| CN | 102188270 A | 9/2011 |
| CN | 101534723 B | 1/2012 |
| CN | 202313540 U | 7/2012 |
| CN | 101541251 A | 11/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U1 | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 4/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |

(56) References Cited

FOREIGN PATENT DOCUMENTS

| | | |
|---|---|---|
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |

(56) References Cited

FOREIGN PATENT DOCUMENTS

| | | |
|---|---|---|
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110083 A2 | 10/2009 |
| EP | 2110084 A2 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |

(56) References Cited

FOREIGN PATENT DOCUMENTS

| | | |
|---|---|---|
| EP | 2517651 A2 | 10/2012 |
| EP | 2526877 A1 | 11/2012 |
| EP | 1884206 B1 | 3/2013 |
| EP | 2090238 B1 | 4/2013 |
| EP | 1806103 B1 | 5/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2759267 A2 | 7/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | H02279149 A | 11/1990 |
| JP | H0312126 A | 1/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H0672357 A | 1/1994 |
| JP | H0630945 A | 2/1994 |
| JP | H0654857 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H0731623 A | 2/1995 |
| JP | H0747070 A | 2/1995 |
| JP | H0751273 A | 2/1995 |
| JP | H07124166 A | 5/1995 |
| JP | H07163574 A | 6/1995 |
| JP | H07171163 A | 7/1995 |
| JP | H07255735 A | 10/1995 |
| JP | H07285089 A | 10/1995 |
| JP | H0833641 A | 2/1996 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H10113352 A | 5/1998 |
| JP | H10118090 A | 5/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003523251 A | 8/2003 |
| JP | 2003523254 A | 8/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005521109 A | 7/2005 |
| JP | 2005523105 A | 8/2005 |

(56) References Cited

FOREIGN PATENT DOCUMENTS

| | | |
|---|---|---|
| JP | 2005524474 A | 8/2005 |
| JP | 2005296412 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006506106 A | 2/2006 |
| JP | 2006510879 A | 3/2006 |
| JP | 2006187649 A | 7/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 3934161 B2 | 6/2007 |
| JP | 2007203049 A | 8/2007 |
| JP | 2007203051 A | 8/2007 |
| JP | 2007203057 A | 8/2007 |
| JP | 2007209751 A | 8/2007 |
| JP | 2007524435 A | 8/2007 |
| JP | 2007222615 A | 9/2007 |
| JP | 2007229448 A | 9/2007 |
| JP | 4001860 B2 | 10/2007 |
| JP | 2007325922 A | 12/2007 |
| JP | 2008068073 A | 3/2008 |
| JP | 2008206967 A | 9/2008 |
| JP | 2008212637 A | 9/2008 |
| JP | 2008212638 A | 9/2008 |
| JP | 2008220956 A | 9/2008 |
| JP | 2008259860 A | 10/2008 |
| JP | 2008264535 A | 11/2008 |
| JP | 2008283459 A | 11/2008 |
| JP | 2009502351 A | 1/2009 |
| JP | 2009506799 A | 2/2009 |
| JP | 2009507526 A | 2/2009 |
| JP | 2009072599 A | 4/2009 |
| JP | 2009090113 A | 4/2009 |
| JP | 2009106752 A | 5/2009 |
| JP | 2009189836 A | 8/2009 |
| JP | 2009189837 A | 8/2009 |
| JP | 2009189838 A | 8/2009 |
| JP | 2009536082 A | 10/2009 |
| JP | 2009261944 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504846 A | 2/2010 |
| JP | 2010505524 A | 2/2010 |
| JP | 2010069310 A | 4/2010 |
| JP | 2010088876 A | 4/2010 |
| JP | 2010098844 A | 4/2010 |
| JP | 4461008 B2 | 5/2010 |
| JP | 4549018 B2 | 9/2010 |
| JP | 2010540192 A | 12/2010 |
| JP | 4783373 B2 | 9/2011 |
| JP | 5140421 B2 | 2/2013 |
| JP | 5162595 B2 | 3/2013 |
| JP | 2013128791 A | 7/2013 |
| JP | 5333899 B2 | 11/2013 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-9412108 A1 | 6/1994 |
| WO | WO-9418893 A1 | 9/1994 |
| WO | WO-9420030 A1 | 9/1994 |
| WO | WO-9422378 A1 | 10/1994 |
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |

(56) References Cited

FOREIGN PATENT DOCUMENTS

| | | |
|---|---|---|
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024322 A1 | 5/2000 |
| WO | WO-0024330 A1 | 5/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A1 | 1/2003 |
| WO | WO-03001986 A2 | 1/2003 |
| WO | WO-03013363 A1 | 2/2003 |
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005055846 A1 | 6/2005 |
| WO | WO-2005072634 A2 | 8/2005 |

(56) References Cited

FOREIGN PATENT DOCUMENTS

| | | |
|---|---|---|
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006051252 A1 | 5/2006 |
| WO | WO-2006059067 A1 | 6/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007016290 A2 | 2/2007 |
| WO | WO-2007018898 A2 | 2/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007131110 A1 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021969 A2 | 2/2008 |
| WO | WO-2008039249 A1 | 4/2008 |
| WO | WO-2008039270 A1 | 4/2008 |
| WO | WO-2008045383 A2 | 4/2008 |
| WO | WO-2008057281 A2 | 5/2008 |
| WO | WO-2008070763 A1 | 6/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109125 A1 | 9/2008 |
| WO | WO-2008124748 A1 | 10/2008 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2010028332 A2 | 3/2010 |
| WO | WO-2010030434 A1 | 3/2010 |
| WO | WO-2010050771 A2 | 5/2010 |
| WO | WO-2010054404 A1 | 5/2010 |
| WO | WO-2010063795 A1 | 6/2010 |
| WO | WO-2010093333 A1 | 8/2010 |
| WO | WO-2010098871 A2 | 9/2010 |
| WO | WO-2011008672 A2 | 1/2011 |
| WO | WO-2011013103 A1 | 2/2011 |
| WO | WO-2011044343 A2 | 4/2011 |
| WO | WO-2011060311 A2 | 5/2011 |
| WO | WO-2012006306 A2 | 1/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012058213 A2 | 5/2012 |
| WO | WO-2012068156 A2 | 5/2012 |
| WO | WO-2012127462 A1 | 9/2012 |
| WO | WO-2012143913 A2 | 10/2012 |
| WO | WO-2012148667 A2 | 11/2012 |
| WO | WO-2012148703 A2 | 11/2012 |
| WO | WO-2012160163 A1 | 11/2012 |
| WO | WO-2013009699 A2 | 1/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013/087092 A1 | 6/2013 |
| WO | WO-2013148762 A2 | 10/2013 |
| WO | WO-2013167427 A1 | 11/2013 |
| WO | WO-2014004199 A1 | 1/2014 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

"Biomedical Coatings," Fort Wayne Metals, Research Products Corporation, obtained online at www.fwmetals.com on Jun. 21,2010 (1 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

(56) References Cited

OTHER PUBLICATIONS

Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
The Sodem Aseptic Battery Transfer Kit, Sodem Systems, 2000, 3 pages.
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
"Indian Standard: Automotive Vehicles—Brakes and Braking Systems (IS 11852-1:2001)", Mar. 1, 2001.

\* cited by examiner

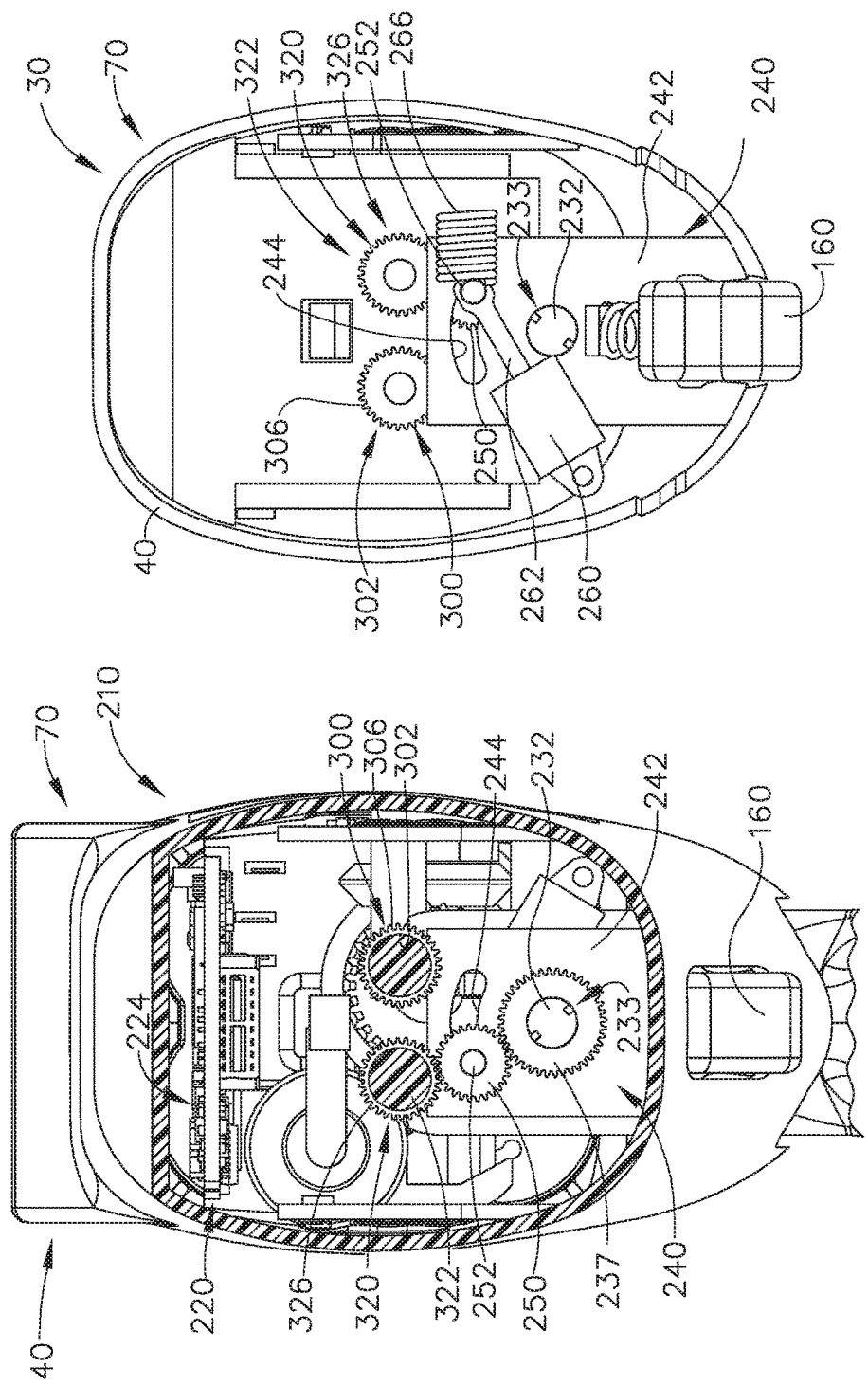

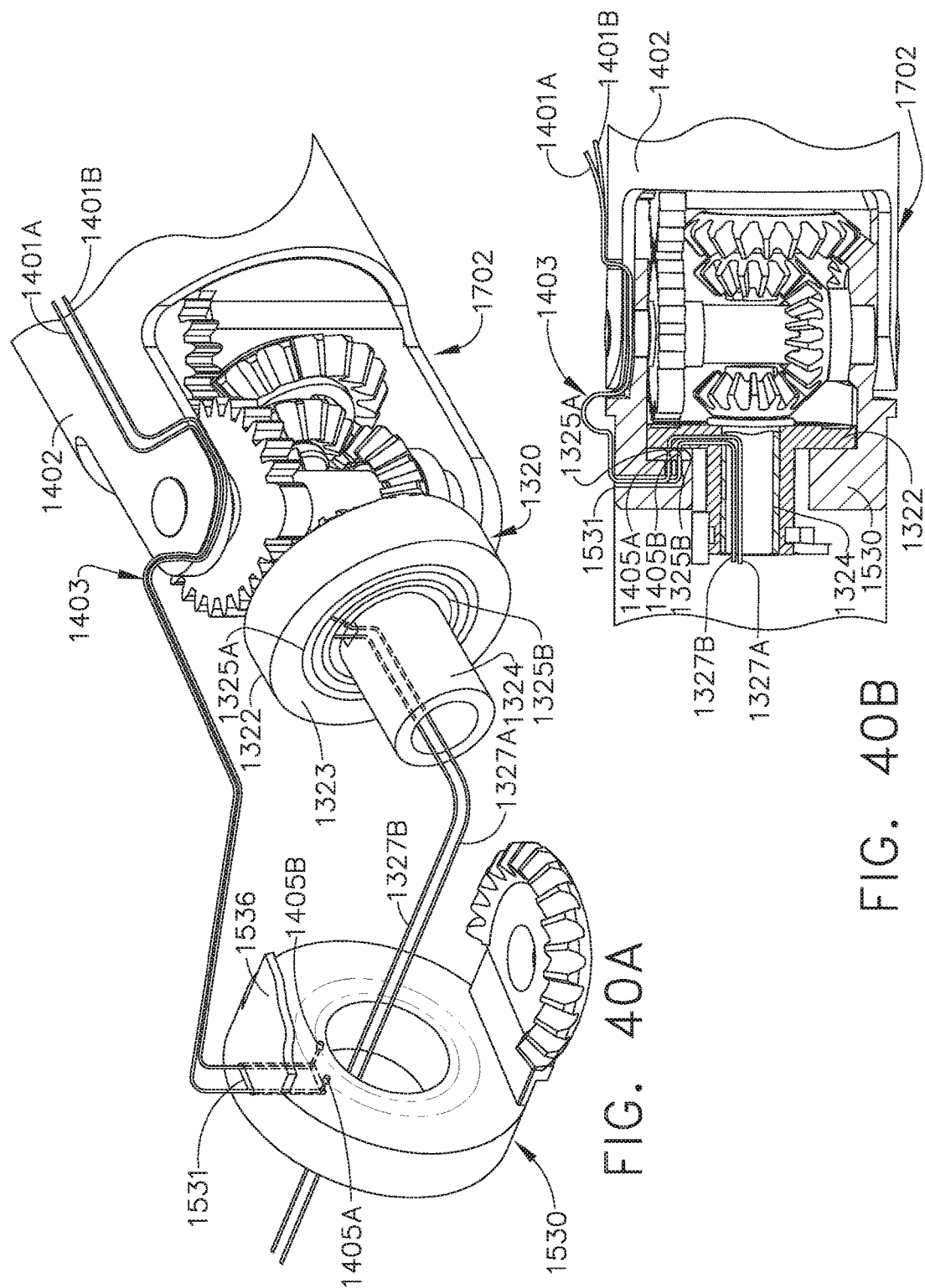

ROTARY POWERED SURGICAL INSTRUMENT WITH MANUALLY ACTUATABLE BAILOUT SYSTEM

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 8 is another end cross-sectional view of the handle assembly of FIGS. 2-7 showing a shifter gear in meshing engagement with a drive gear on a rotary drive socket;

FIG. 9 is another end cross-sectional view of the handle assembly of FIGS. 2-8 showing the position of a shifter solenoid when the shifter gear is in meshing engagement with the drive gear on the rotary drive socket;

FIG. 40A is a partial exploded perspective view of an articulation joint and end effector illustrating one arrangement for facilitating the supply of electrical signals to the end effector around the articulation joint in accordance with at least one embodiment;

FIG. 40B is a side elevational view of the articulation joint and end effector of FIG. 40A with some components thereof shown in cross-section;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
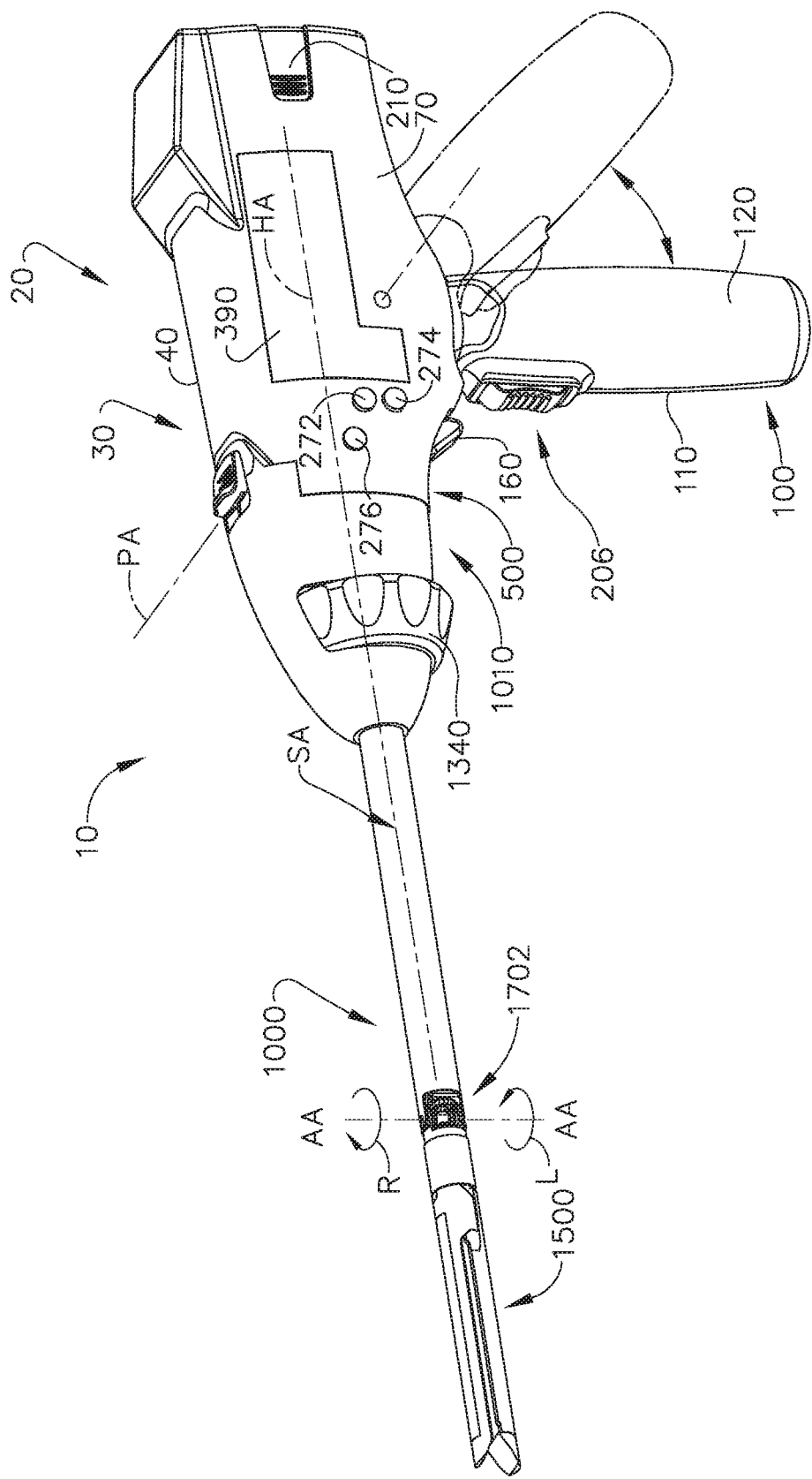
FIG. 1 is a perspective view of a surgical instrument including an interchangeable surgical tool assembly in accordance with at least one embodiment.

Applicant of the present application owns the following patent applications that were filed on Apr. 1, 2016 and which are each herein incorporated by reference in their respective entireties:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Patent Application Publication No. 2017/0281163;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No.; 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,277, entitled SURGICAL CUTTING AND STAPLING END EFFECTOR WITH ANVIL CONCENTRIC DRIVE MEMBER, now U.S. Patent Application No. 2017/0281166;

U.S. patent application Ser. No. 15/089,283, entitled CLOSURE SYSTEM ARRANGEMENTS FOR SURGICAL CUTTING AND STAPLING DEVICES WITH SEPARATE AND DISTINCT FIRING SHAFTS, now U.S. Patent Application Publication No. 2017/0281167;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 2017/0281183;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No.; 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

The Applicant of the present application also owns the U.S. Patent Applications identified below which were filed on Dec. 31, 2015 which are each herein incorporated by reference in their respective entirety:
- U.S. patent application Ser. No. 14/984,488, entitled MECHANISMS FOR COMPENSATING FOR BATTERY PACK FAILURE IN POWERED SURGICAL INSTRUMENTS;
- U.S. patent application Ser. No. 14/984,525, entitled MECHANISMS FOR COMPENSATING FOR DRIVETRAIN FAILURE IN POWERED SURGICAL INSTRUMENTS; and
- U.S. patent application Ser. No. 14/984,552, entitled SURGICAL INSTRUMENTS WITH SEPARABLE MOTORS AND MOTOR CONTROL CIRCUITS.

The Applicant of the present application also owns the U.S. Patent Applications identified below which were filed on Feb. 9, 2016 which are each herein incorporated by reference in their respective entirety:
- U.S. patent application Ser. No. 15/019,220, entitled SURGICAL INSTRUMENT WITH ARTICULATING AND AXIALLY TRANSLATABLE END EFFECTOR;
- U.S. patent application Ser. No. 15/019,228, entitled SURGICAL INSTRUMENTS WITH MULTIPLE LINK ARTICULATION ARRANGEMENTS;
- U.S. patent application Ser. No. 15/019,196, entitled SURGICAL INSTRUMENT ARTICULATION MECHANISM WITH SLOTTED SECONDARY CONSTRAINT;
- U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;
- U.S. patent application Ser. No. 15/019,215, entitled SURGICAL INSTRUMENTS WITH NON-SYMMETRICAL ARTICULATION ARRANGEMENTS;
- U.S. patent application Ser. No. 15/019,227, entitled ARTICULATABLE SURGICAL INSTRUMENTS WITH SINGLE ARTICULATION LINK ARRANGEMENTS;
- U.S. patent application Ser. No. 15/019,235, entitled SURGICAL INSTRUMENTS WITH TENSIONING ARRANGEMENTS FOR CABLE DRIVEN ARTICULATION SYSTEMS;
- U.S. patent application Ser. No. 15/019,230, entitled ARTICULATABLE SURGICAL INSTRUMENTS WITH OFF-AXIS FIRING BEAM ARRANGEMENTS; and
- U.S. patent application Ser. No. 15/019,245, entitled SURGICAL INSTRUMENTS WITH CLOSURE STROKE REDUCTION ARRANGEMENTS.

The Applicant of the present application also owns the U.S. Patent Applications identified below which were filed on Feb. 12, 2016 which are each herein incorporated by reference in their respective entirety:
- U.S. patent application Ser. No. 15/043,254, entitled MECHANISMS FOR COMPENSATING FOR DRIVETRAIN FAILURE IN POWERED SURGICAL INSTRUMENTS;
- U.S. patent application Ser. No. 15/043,259, entitled MECHANISMS FOR COMPENSATING FOR DRIVETRAIN FAILURE IN POWERED SURGICAL INSTRUMENTS;
- U.S. patent application Ser. No. 15/043,275, entitled MECHANISMS FOR COMPENSATING FOR DRIVETRAIN FAILURE IN POWERED SURGICAL INSTRUMENTS; and
- U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entireties:
- U.S. patent application Ser. No. 14/742,925, entitled SURGICAL END EFFECTORS WITH POSITIVE JAW OPENING ARRANGEMENTS;
- U.S. patent application Ser. No. 14/742,941, entitled SURGICAL END EFFECTORS WITH DUAL CAM ACTUATED JAW CLOSING FEATURES;
- U.S. patent application Ser. No. 14/742,914, entitled MOVABLE FIRING BEAM SUPPORT ARRANGEMENTS FOR ARTICULATABLE SURGICAL INSTRUMENTS;
- U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;
- U.S. patent application Ser. No. 14/742,885, entitled DUAL ARTICULATION DRIVE SYSTEM ARRANGEMENTS FOR ARTICULATABLE SURGICAL INSTRUMENTS; and
- U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entireties:
- U.S. patent application Ser. No. 14/640,746, entitled POWERED SURGICAL INSTRUMENT;
- U.S. patent application Ser. No. 14/640,795, entitled MULTIPLE LEVEL THRESHOLDS TO MODIFY OPERATION OF POWERED SURGICAL INSTRUMENTS;
- U.S. patent application Ser. No. 14/640,832, entitled ADAPTIVE TISSUE COMPRESSION TECHNIQUES TO ADJUST CLOSURE RATES FOR MULTIPLE TISSUE TYPES;
- U.S. patent application Ser. No. 14/640,935, entitled OVERLAID MULTI SENSOR RADIO FREQUENCY (RF) ELECTRODE SYSTEM TO MEASURE TISSUE COMPRESSION;
- U.S. patent application Ser. No. 14/640,831, entitled MONITORING SPEED CONTROL AND PRECISION INCREMENTING OF MOTOR FOR POWERED SURGICAL INSTRUMENTS;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES;
- U.S. patent application Ser. No. 14/640,817, entitled INTERACTIVE FEEDBACK SYSTEM FOR POWERED SURGICAL INSTRUMENTS;
- U.S. patent application Ser. No. 14/640,844, entitled CONTROL TECHNIQUES AND SUB-PROCESSOR

CONTAINED WITHIN MODULAR SHAFT WITH SELECT CONTROL PROCESSING FROM HANDLE;

U.S. patent application Ser. No. 14/640,837, entitled SMART SENSORS WITH LOCAL SIGNAL PROCESSING;

U.S. patent application Ser. No. 14/640,765, entitled SYSTEM FOR DETECTING THE MIS-INSERTION OF A STAPLE CARTRIDGE INTO A SURGICAL STAPLER;

U.S. patent application Ser. No. 14/640,799, entitled SIGNAL AND POWER COMMUNICATION SYSTEM POSITIONED ON A ROTATABLE SHAFT; and U.S. patent application Ser. No. 14/640,780, entitled SURGICAL INSTRUMENT COMPRISING A LOCKABLE BATTERY HOUSING.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND;

U.S. patent application Ser. No. 14/633,560, entitled SURGICAL CHARGING SYSTEM THAT CHARGES AND/OR CONDITIONS ONE OR MORE BATTERIES;

U.S. patent application Ser. No. 14/633,566, entitled CHARGING SYSTEM THAT ENABLES EMERGENCY RESOLUTIONS FOR CHARGING A BATTERY;

U.S. patent application Ser. No. 14/633,555, entitled SYSTEM FOR MONITORING WHETHER A SURGICAL INSTRUMENT NEEDS TO BE SERVICED;

U.S. patent application Ser. No. 14/633,542, entitled REINFORCED BATTERY FOR A SURGICAL INSTRUMENT;

U.S. patent application Ser. No. 14/633,548, entitled POWER ADAPTER FOR A SURGICAL INSTRUMENT;

U.S. patent application Ser. No. 14/633,526, entitled ADAPTABLE SURGICAL INSTRUMENT HANDLE;

U.S. patent application Ser. No. 14/633,541, entitled MODULAR STAPLING ASSEMBLY; and U.S. patent application Ser. No. 14/633,562, entitled SURGICAL APPARATUS CONFIGURED TO TRACK AN END-OF-LIFE PARAMETER.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING;

U.S. patent application Ser. No. 14/574,483, entitled SURGICAL INSTRUMENT ASSEMBLY COMPRISING LOCKABLE SYSTEMS;

U.S. patent application Ser. No. 14/575,139, entitled DRIVE ARRANGEMENTS FOR ARTICULATABLE SURGICAL INSTRUMENTS;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE;

U.S. patent application Ser. No. 14/575,143, entitled SURGICAL INSTRUMENTS WITH IMPROVED CLOSURE ARRANGEMENTS;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS;

U.S. patent application Ser. No. 14/574,493, entitled SURGICAL INSTRUMENT ASSEMBLY COMPRISING A FLEXIBLE ARTICULATION SYSTEM; and U.S. patent application Ser. No. 14/574,500, entitled SURGICAL INSTRUMENT ASSEMBLY COMPRISING A LOCKABLE ARTICULATION SYSTEM.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Paten Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Patent Application Publication No. 2014/0246474;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Paten Application Publication No. 2014/0246477;

U.S. patent application Ser. No. 13/782,481, entitled SENSOR STRAIGHTENED END EFFECTOR DURING REMOVAL THROUGH TROCAR, now U.S. Patent Application Publication No. 2014/0246479;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Patent Application Publication No. 2014/0246473; and U.S. patent application Ser. No. 13/782,536, entitled SURGICAL INSTRUMENT SOFT STOP, now U.S. Paten Application Publication No. 2014/0246476.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Paten Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Patent Application Publication No. 2014/0263537;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Paten Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Patent Application Publication No. 2014/0263553;

U.S. patent application Ser. No. 13/803,130, entitled DRIVE TRAIN CONTROL ARRANGEMENTS FOR MODULAR SURGICAL INSTRUMENTS, now U.S. Patent Application Publication No. 2014/0263543; and U.S. patent application Ser. No. 13/803,159, entitled METHOD AND SYSTEM FOR OPERATING A SURGICAL INSTRUMENT, now U.S. Paten Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Paten Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Paten Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Paten Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAIL-OUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Paten Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Paten Application Publication No. 2015/0272572;

U.S. patent application Ser. No. 14/226,133, entitled MODULAR SURGICAL INSTRUMENT SYSTEM, now U.S. Paten Application Publication No. 2015/0272557;

U.S. patent application Ser. No. 14/226,081, entitled SYSTEMS AND METHODS FOR CONTROLLING A SEGMENTED CIRCUIT, now U.S. Paten Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Paten Application Publication No. 2015/0272583; and U.S. patent application Ser. No. 14/226,125, entitled SURGICAL INSTRUMENT COMPRISING A ROTATABLE SHAFT, now U.S. Paten Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Paten Application Publication No. 2016/0066909;

U.S. patent application Ser. No. 14/479,110, entitled USE OF POLARITY OF HALL MAGNET DETECTION TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Paten Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Paten Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Paten Application Publication No. 2014/0305988;

U.S. patent application Ser. No. 14/248,588, entitled POWERED LINEAR SURGICAL STAPLER, now U.S. Paten Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Paten Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Handle Assembly

FIG. 1 depicts a motor-driven surgical system 10 that may be used to perform a variety of different surgical procedures. In the illustrated embodiment, the motor driven surgical system 10 comprises a selectively reconfigurable housing or handle assembly 20 that is attached to one form of an interchangeable surgical tool assembly 1000. For example, the system 10 that is depicted in FIG. 1 includes an interchangeable surgical tool assembly 1000 that comprises a surgical cutting and fastening instrument which may be referred to as an endocutter. As will be discussed in further detail below, the interchangeable surgical tool assemblies may include end effectors that are adapted to support different sizes and types of staple cartridges and, have different shaft lengths, sizes, and types, etc. Such arrangements, for example, may utilize any suitable fastener, or fasteners, to fasten tissue. For instance, a fastener cartridge comprising a plurality of fasteners removably stored therein can be removably inserted into and/or attached to the end effector of a surgical tool assembly. Other surgical tool assemblies may be interchangeably employed with the handle assembly 20. For example, the interchangeable surgical tool assembly 1000 may be detached from the handle assembly 20 and replaced with a different surgical tool assembly that is configured to perform other surgical procedures. In other arrangements, the surgical tool assembly may not be interchangeable with other surgical tool assemblies and essentially comprise a dedicated shaft that is non-removably affixed or coupled to the handle assembly 20, for example. The surgical tool assemblies may also be referred to as elongate shaft assemblies. The surgical tool assemblies may be reusable or, in other configurations, the surgical tool assemblies may be designed to be disposed of after a single use.

As the present Detailed Description proceeds, it will be understood that the various forms of interchangeable surgical tool assemblies disclosed herein may also be effectively employed in connection with robotically-controlled surgical systems. Thus, the terms "housing" and "housing assembly" may also encompass a housing or similar portion of a robotic system that houses or otherwise operably supports at least one drive system that is configured to generate and apply at least one control motion which could be used to actuate the elongate shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the surgical tool assemblies disclosed herein may be employed with various robotic systems, instruments, components, and methods such as, but not limited to, those disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719 which is hereby incorporated by reference herein in its entirety.

Figure 2:
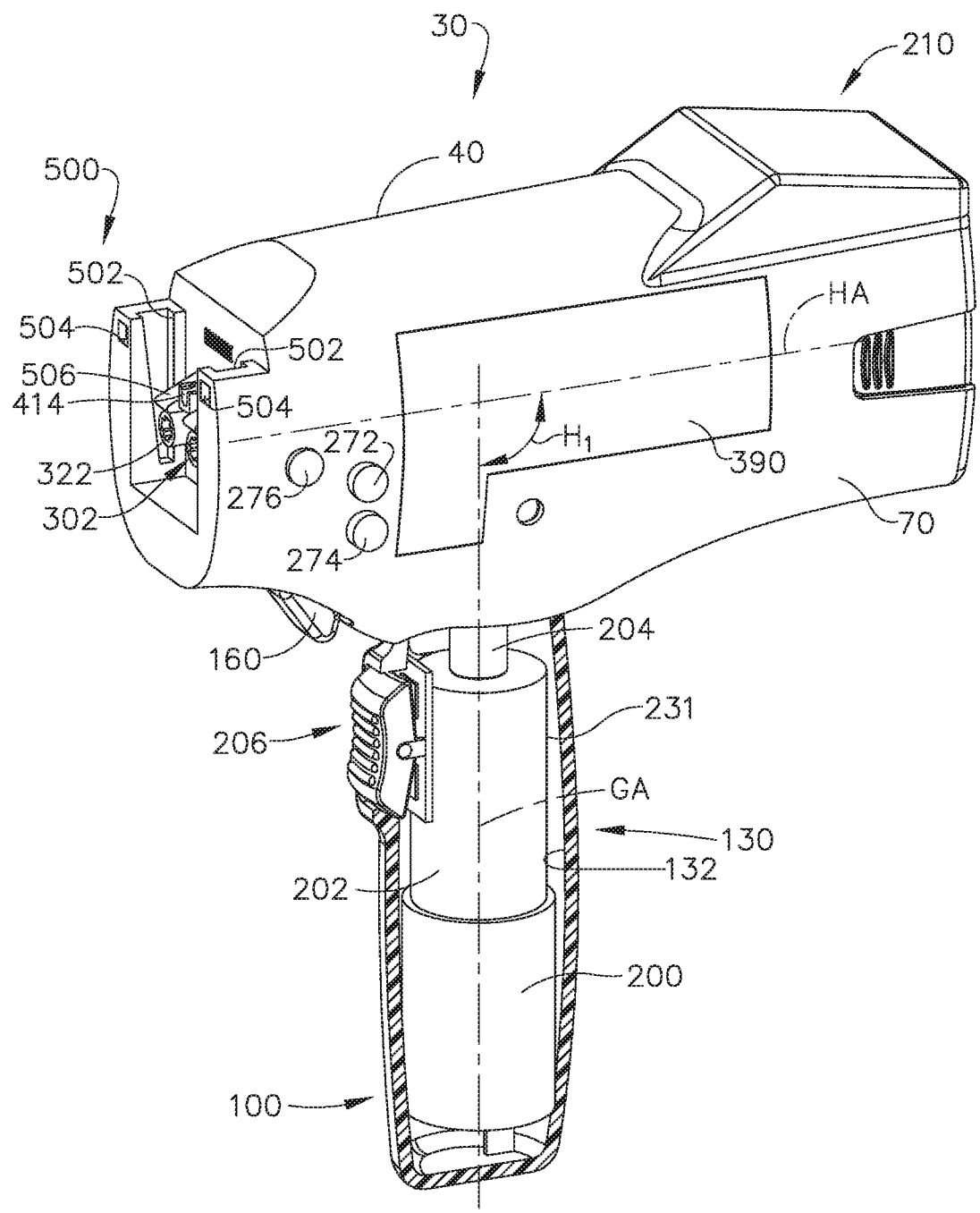
FIG. 2 is another perspective view of a handle assembly of the surgical instrument of FIG. 1, with a portion of the handle housing omitted to expose components housed therein.

Referring now to FIGS. 1 and 2, the housing assembly or handle assembly 20 comprises a primary housing portion 30 that may be formed from a pair of housing segments 40, 70 that may be fabricated from plastic, polymer materials, metal, etc. and be joined together by an appropriate fastener arrangement such as, for example, adhesive, screws, press-fit features, snap-fit features, latches, etc. As will be discussed in further detail below, the primary housing portion 30 operably supports a plurality of drive systems therein that are configured to generate and apply various control motions to corresponding portions of the interchangeable surgical tool assembly that is operably attached thereto. The handle assembly 20 further comprises a grip portion 100 that is movably coupled to the primary housing portion 30 and is configured to be gripped and manipulated by the clinician in various positions relative to the primary housing portion 30. The grip portion 100 may be fabricated from a pair of grip segments 110, 120 that may be fabricated from plastic, polymer materials, metal, etc. and are joined together by an appropriate fastener arrangement such as, for example, adhesive, screws, press-fit features, snap-fit features, latches, etc. for assembly and maintenance purposes.

Figure 5:
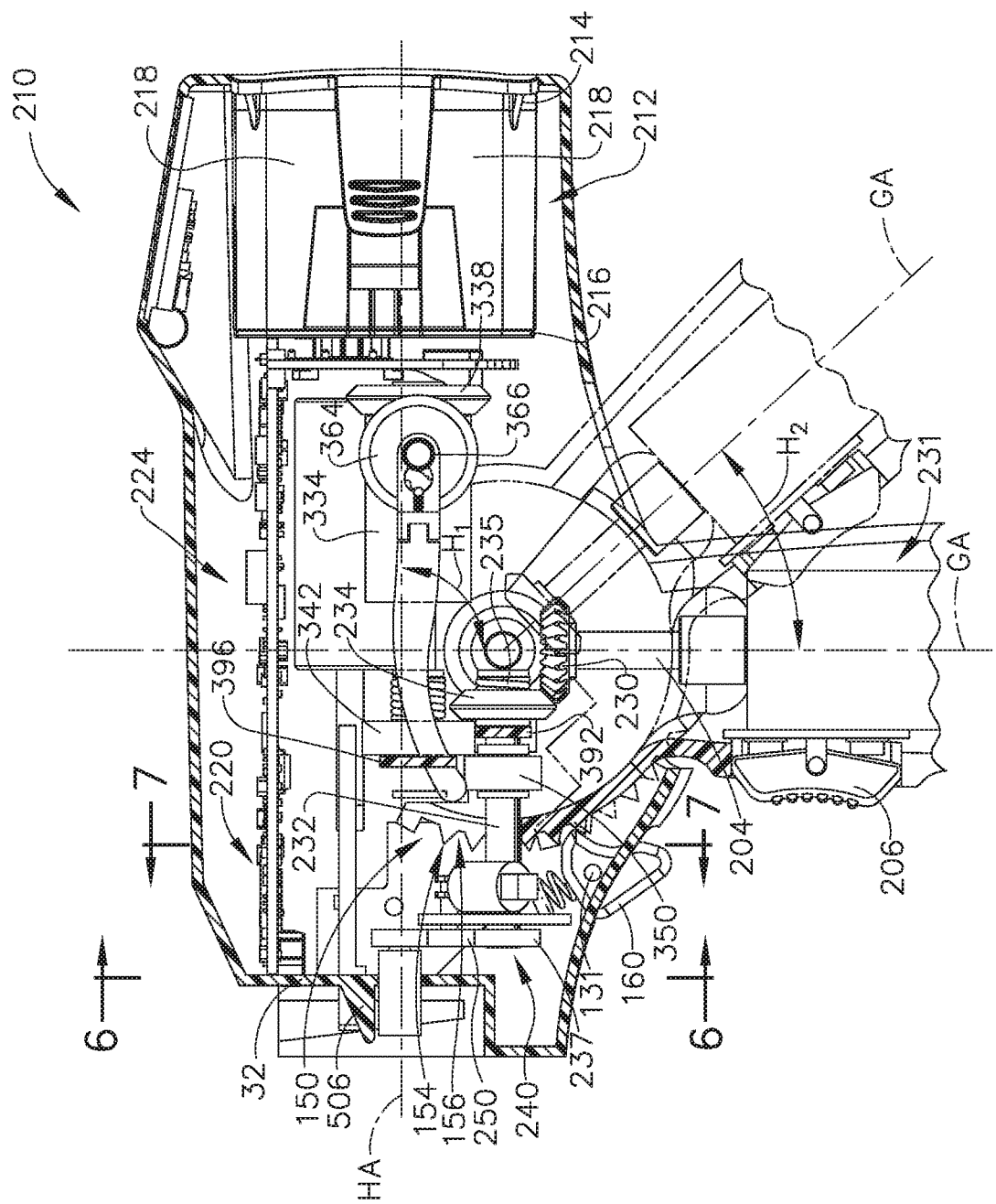
FIG. 5 is a partial cross-sectional side view of the handle assembly of FIGS. 2-4 with a grip portion of the handle assembly shown in solid lines in one position relative to a primary housing portion and in phantom lines in another position relative to the primary housing portion of the handle assembly.

As can be seen in FIG. 2, the grip portion 100 comprises a grip housing 130 that defines a hollow cavity 132 that is configured to operably support a drive motor and gearbox which will be discussed in further detail below. The upper portion 134 of the grip housing 130 is configured to extend through an opening 80 in the primary housing portion 30 and be pivotally journaled on a pivot shaft 180. The pivot shaft 180 defines a pivot axis designated as "PA". See FIG. 3. For reference purposes, the handle assembly 20 defines a handle axis designated as "HA" that may be parallel to the shaft axis "SA" of the elongate shaft assembly of the interchangeable surgical tool that is operably attached to the handle assembly 20. The pivot axis PA is transverse to the handle axis HA. See FIG. 1. Such arrangement enables the grip portion 100 to be pivoted relative to the primary housing portion 30 about the pivot axis PA to a position that is best suited for the type of interchangeable surgical tool assembly that is coupled to the handle assembly 20. The grip housing 130 defines a grip axis, generally designated as "GA". See FIG. 2. When the interchangeable surgical tool assembly that is coupled to the handle assembly 20 comprises an endocutter for example, the clinician might want to position the grip portion 100 relative to the primary housing portion 30 such that the grip axis GA is perpendicular or approximately perpendicular (angle "H1") to the handle axis HA (referred to herein as a "first grip position"). See FIG. 5. However, if the handle assembly 20 is being used to control an interchangeable surgical tool assembly that comprises a circular stapler for example, the clinician may wish to pivot the grip portion 100 relative to the primary housing portion 30 to a position wherein the grip axis GA is at a forty-five degree or approximately forty-five degree angle or other suitable acute angle (angle "H2") relative to the handle axis HA. This position is referred to herein as a "second grip position". FIG. 5 illustrates the grip portion 100 in phantom lines in the second grip position.

Figure 3:
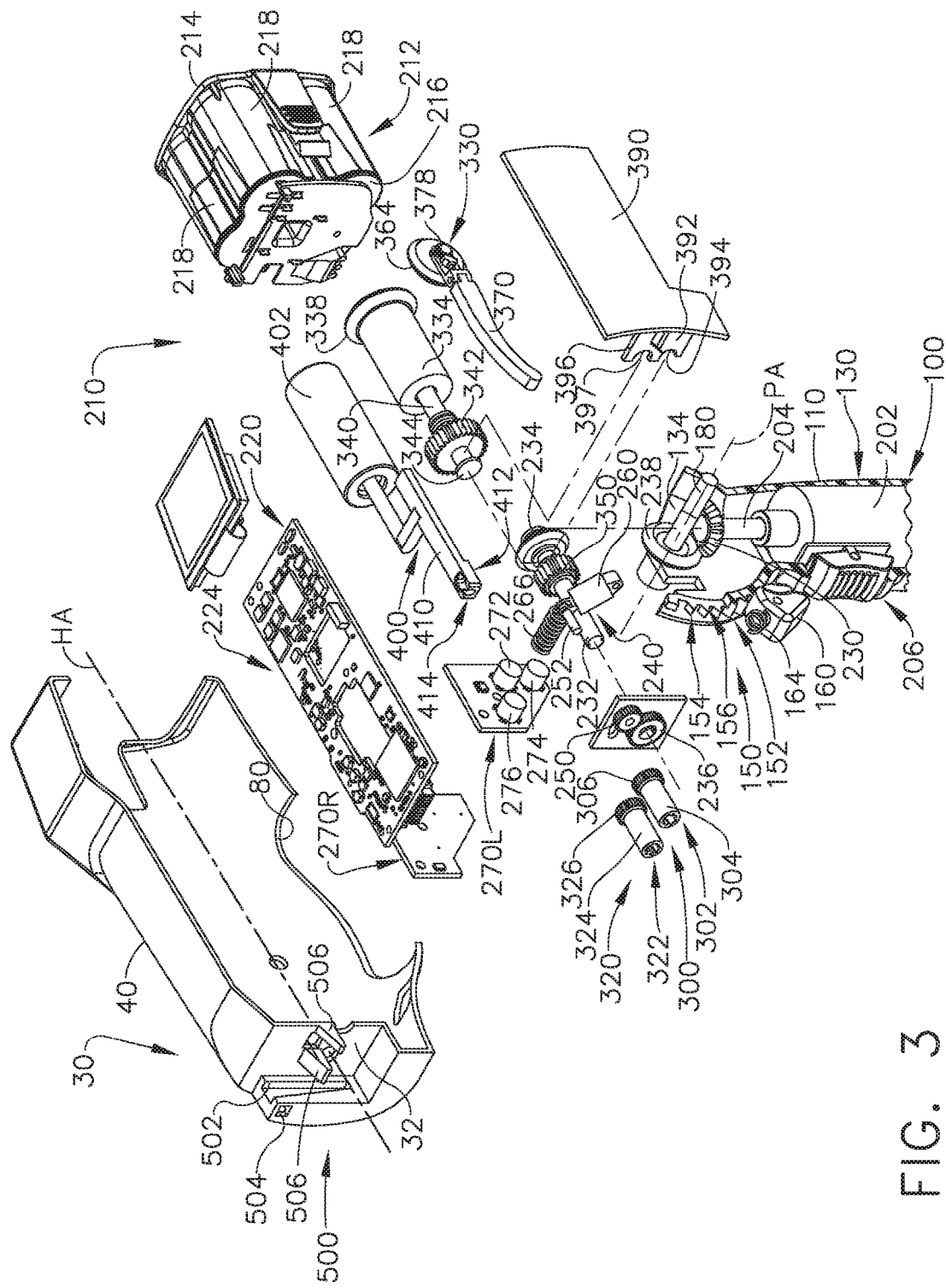
FIG. 3 is an exploded assembly view of portions of the handle assembly of the surgical instrument of FIGS. 1 and 2.
Figure 4:
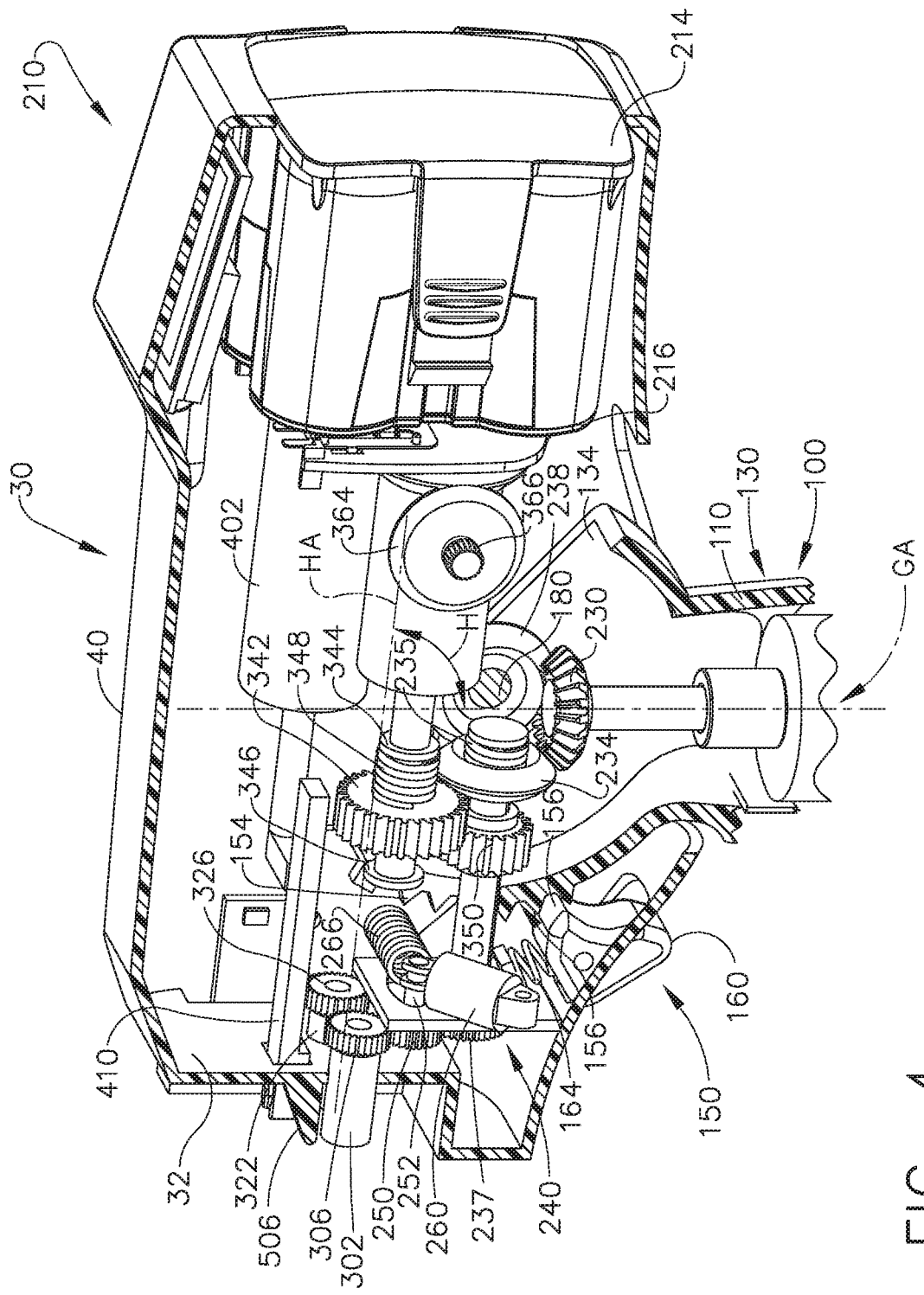
FIG. 4 is a cross-sectional perspective view of the handle assembly of FIGS. 2 and 3.

Referring now to FIGS. 3-5, the handle assembly 20 also includes a grip locking system, generally designated as 150, for selectively locking the grip portion 100 in the desired orientation relative to the primary housing portion 30. In one arrangement, the grip locking system 150 comprises an arcuate series 152 of pointed teeth 154. The teeth 154 are spaced from each other and form a locking groove 156 therebetween. Each locking groove 156 corresponds to a particular angular locking position for the grip portion 100. For example, in at least one arrangement, the teeth 154 and locking grooves or "locking locations" 156 are arranged to permit the grip portion 100 to be locked at 10-15 degree intervals between the first grip position and the second grip position. The arrangement may employ two stop positions which are tailored to the type of instrument (shaft arrangement) employed. For example, for an endocutter shaft arrangement, it may be approximately around ninety degrees to the shaft and for a circular stapler arrangement, the angle may be approximately forty-five degrees to the shaft while being swept forward towards the surgeon. The grip locking system 150 further includes a locking button 160 that has a locking portion that is configured to lockingly engage the locking grooves 156. For example, the locking button 160 is pivotally mounted in the primary handle portion 30 on a pivot pin 131 to permit the locking button 160 to pivot into engagement with a corresponding locking groove 156. A locking spring 164 serves to bias the locking button 160 into an engaged or locked position with the corresponding locking groove 156. The locking portion and the teeth configurations serve to enable the teeth 154 to slide past the locking portion when the clinician depresses the locking button 160. Thus, to adjust the angular position of the grip portion 100 relative to the primary housing portion 30, the clinician depresses the locking button 160 and then pivots the grip portion 100 to the desired angular position. Once the grip portion 100 has been moved to the desired position, the clinician releases the locking button 160. The locking spring 164 will then bias the locking button 160 toward the series of teeth 154 so that the locking portion enters the corresponding locking groove 156 to retain the grip portion 100 in that position during use.

Drive Systems

The handle assembly 20 operably supports a first rotary drive system 300, a second rotary drive system 320 and a third axial drive system 400. The rotary drive systems 300, 320 are each powered by a motor 200 that is operably supported in the grip portion 100. As can be seen in FIG. 2, for example, the motor 200 is supported within the cavity 132 in the grip portion 100 and has a gear box assembly 202 that has an output drive shaft 204 protruding therefrom. In various forms, the motor 200 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 200 may be powered by a power source 210 that, in one form, may comprise a removable power pack 212. The power source 210 may comprise, for example, anyone of the various power source arrangements disclosed in further detail in U.S. Paten Application Publication No. 2015/0272575 and entitled SURGICAL INSTRUMENT COMPRISING A SENSOR SYSTEM, the entire disclosure of which is hereby incorporated by reference herein. In the illustrated arrangement, for example, the power pack 212 may comprise a proximal housing portion 214 that is configured for attachment to a distal housing portion 216. The proximal housing portion 214 and the distal housing portion 216 are configured to operably support a plurality of batteries 218 therein. Batteries 218 may each comprise, for example, a Lithium Ion ("LI") or other suitable battery. The distal housing portion 216 is configured for removable operable attachment to a handle circuit board assembly 220 which is also operably coupled to the motor 200. The handle circuit board assembly 220 may also be generally referred to herein as the "control system or CPU 224". A number of batteries 218 may be connected in series may be used as the power source for the handle assembly 20. In addition, the power source 210 may be replaceable and/or rechargeable. In other embodiments, the surgical instrument 10 may be powered by alternating current (AC) for example. The motor 200 may be controlled by a rocker switch 206 that is mounted to the grip portion 100.

Figure 14:
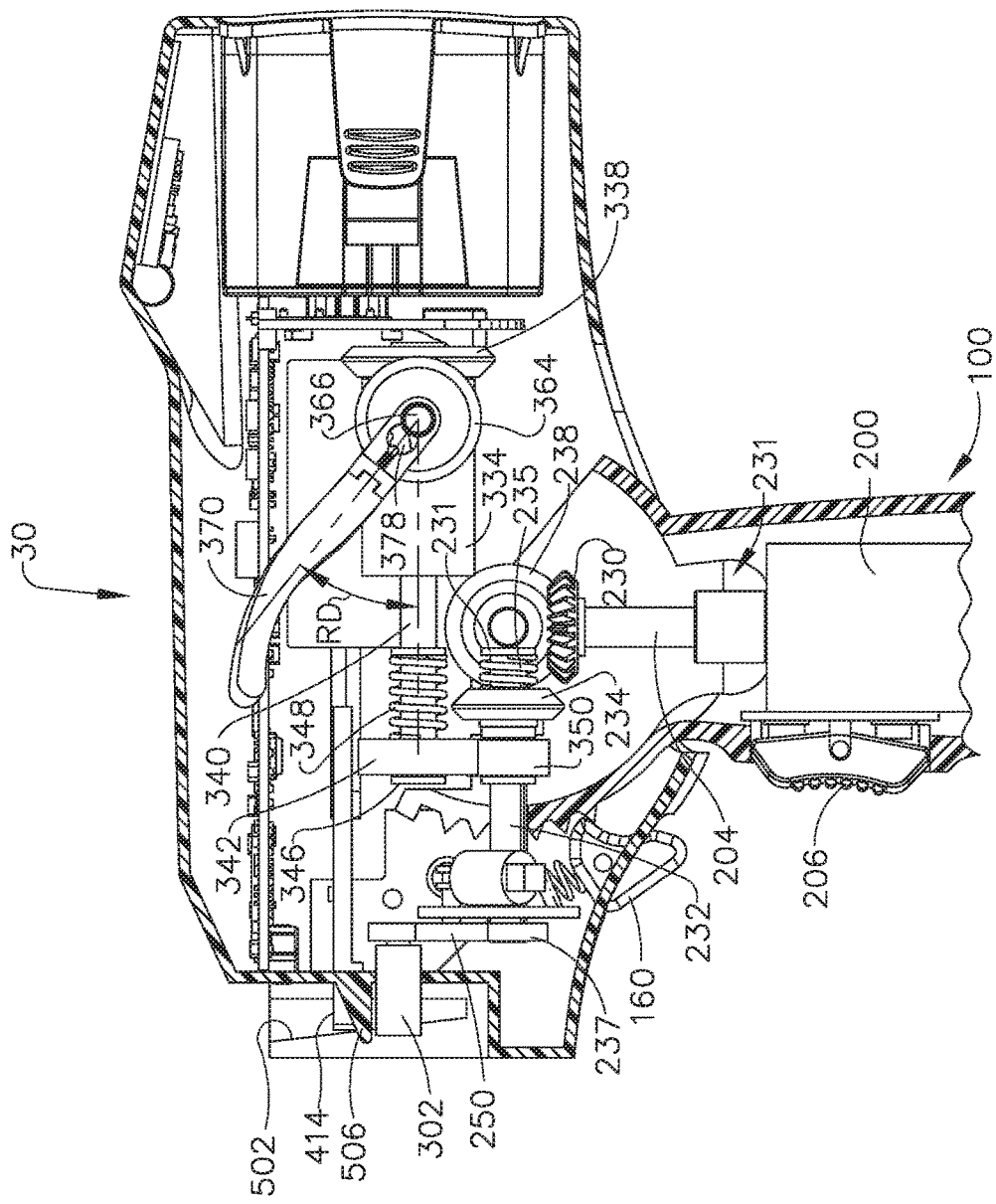
FIG. 14 is a cross-sectional elevation view of the handle assembly of FIG. 11.

As outlined above, the motor 200 is operably coupled to a gear box assembly 202 that includes an output drive shaft 204. Attached to the output drive shaft 204 is a driver bevel gear 230. The motor 200, the gear box assembly 202, the output drive shaft 204 and the driver bevel gear 230 may also be collectively referred to herein as a "motor assembly 231". The driver bevel gear 230 interfaces with a driven bevel gear 234 that is attached to a system drive shaft 232 as well as a pivot bevel gear 238 that is journaled on the pivot shaft 180. The driven bevel gear 234 is axially movable on the system drive shaft 232 between an engaged position wherein the driven bevel gear 234 is in meshing engagement with the driver bevel gear 230 (FIG. 5) and a disengaged position wherein the driven bevel gear 234 is out of meshing engagement with the drive bevel gear 230 (FIG. 14). A drive system spring 235 is journaled between the driven bevel gear 234 and a proximal end flange 236 that is formed on a proximal portion of the system drive shaft 232. See FIGS. 4 and 14. The drive system spring 235 serves to bias the driven bevel gear 234 out of meshing engagement with the driver bevel gear 230 as will be discussed in further detail below. The pivot bevel gear 238 facilitates pivotal travel of the output drive shaft 204 and driver bevel gear 230 with the grip portion 100 relative to the primary handle portion 30.

In the illustrated example, the system drive shaft 232 interfaces with a rotary drive selector system, generally designated as 240. In at least one form, for example, the rotary drive selector system 240 comprises a shifter gear 250 that is selectively movable between the first rotary drive system 300 and the second rotary drive system 320. As can be seen in FIGS. 6-9, for example, the drive selector system 240 comprises a shifter mounting plate 242 that is non-movably mounted within primary handle portion 30. For example, the shifter mounting plate 242 may be frictionally retained between mounting lugs (not shown) formed in the housing segments 40, 70 or be otherwise retained therein by screws, adhesive, etc. Still referring to FIGS. 6-9, the system drive shaft 232 extends through a hole in the shifter mounting plate 242 and has the central, or system, drive gear 237 non-rotatably attached thereto. For example the central drive gear 237 may be attached to the system drive shaft 232 by a keyway arrangement 233. See FIGS. 6-9. In other arrangements, the system drive shaft 232 may be rotatably supported in the shifter mounting plate 242 by a corresponding bearing (not shown) that is mounted thereto. In any event, rotation of the system drive shaft 232 will result in rotation of the central drive gear 234.

As can be seen in FIG. 3, the first drive system 300 includes a first drive socket 302 that is rotatably supported in a distal wall 32 formed in the primary handle portion 30. The first drive socket 302 may comprise a first body portion 304 that has a splined socket formed therein. A first driven gear 306 is formed on or is non-movably attached to the first body portion 304. The first body portion 304 may be rotatably supported in a corresponding hole or passage provided the distal wall 32 or it may be rotatably supported in a corresponding bearing (not shown) that is mounted in the distal wall 32. Similarly, the second rotary drive system 320 includes a second drive socket 322 that is also rotatably supported in the distal wall 32 of the primary handle portion 30. The second drive socket 322 may comprise a second body portion 324 that has a splined socket formed therein. A second driven gear 326 is formed on or is non-rotatably mounted to the second body portion 324. The second body portion 324 may be rotatably supported in a corresponding hole or passage provided the distal wall 32 or it may be rotatably supported in a corresponding bearing (not shown) that is mounted in the distal wall 32. The first and second drive sockets 302, 322 are spaced from each other on each lateral side of the handle axis HA. See FIG. 4, for example.

Figures 6, 7:
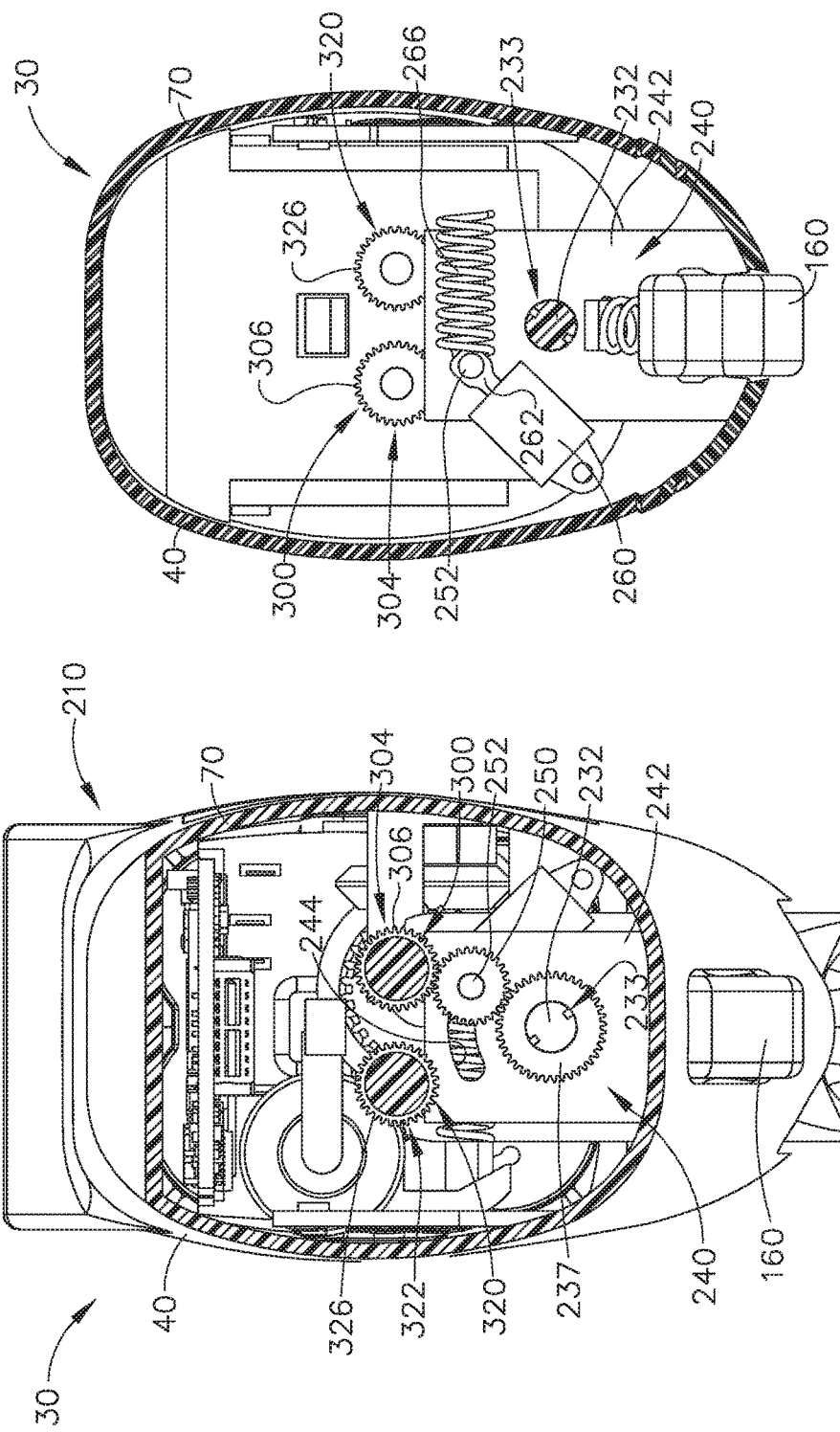
FIG. 6 is an end cross-sectional view of the handle assembly of FIGS. 2-5 taken along line 6-6 in FIG. 5.
FIG. 7 is another end cross-sectional view of the handle assembly of FIGS. 2-6 taken along line 7-7 in FIG. 5.

As indicated above, in the illustrated example, the rotary drive selector system 240 includes a shifter gear 250. As can be seen in FIGS. 6-9, the shifter gear 250 is rotatably mounted on an idler shaft 252 that is movably supported in an arcuate slot 244 in the shifter mounting plate 242. The shifter gear 250 is mounted so as to freely rotate on the idler shaft 252 and remain in meshing engagement with the central drive gear 234. The idler shaft 252 is coupled to an end of a shaft 262 of a shifter solenoid 260. The shifter solenoid 260 is pinned or otherwise mounted with the primary handle housing 30 such that when the shifter solenoid 260 is actuated, the shifter gear 250 is moved into meshing engagement with one of the first driven gear 306 or the second driven gear 326. For example, in one arrangement, when the solenoid shaft is 262 is retracted (FIGS. 6 and 7), the shifter gear 250 is in meshing engagement with the central drive gear 234 and the first driven gear 306 such that actuation of the motor 200 will result in rotation of the first drive socket 302. As can be seen in FIGS. 6 and 7, a shifter spring 266 may be employed to bias the shifter gear 250 into that first actuation position. Thus, should power be lost to the surgical instrument 10, the shifter spring 266 will automatically bias the shifter gear 250 into the first position. When the shifter gear 250 is in that position, subsequent actuation of the motor 200 will result in rotation of the first drive socket 302 of the first rotary drive system 300. When the shifter solenoid is actuated, the shifter gear 250 is moved into meshing engagement with the second driven gear 326 on the second drive socket 322. Thereafter, actuation of the motor 200 will result in actuation or rotation of the second drive socket 322 of the second rotary drive system 320.

Bailout System

As will be discussed in further detail below, the first and second rotary drive systems 300, 320 may be used to power various component portions of the interchangeable surgical tool assembly that is coupled thereto. As indicated above, in at least one arrangement, if during the actuation of the interchangeable surgical tool assembly, power was lost to the motor, the shifter spring 266 will bias the shifter gear 250 to the first position. Depending upon which component portion of the interchangeable surgical tool assembly was being operated, it may be necessary to reverse the application of the rotary drive motion to the first drive system 300 to enable the interchangeable surgical tool assembly to be removed from the patient. The handle assembly 20 of the illustrated example employs a manually actuatable "bailout" system, generally designated as 330, for manually applying a rotary drive motion to the first rotary drive system 300 in the above described scenario, for example.

Figure 10:
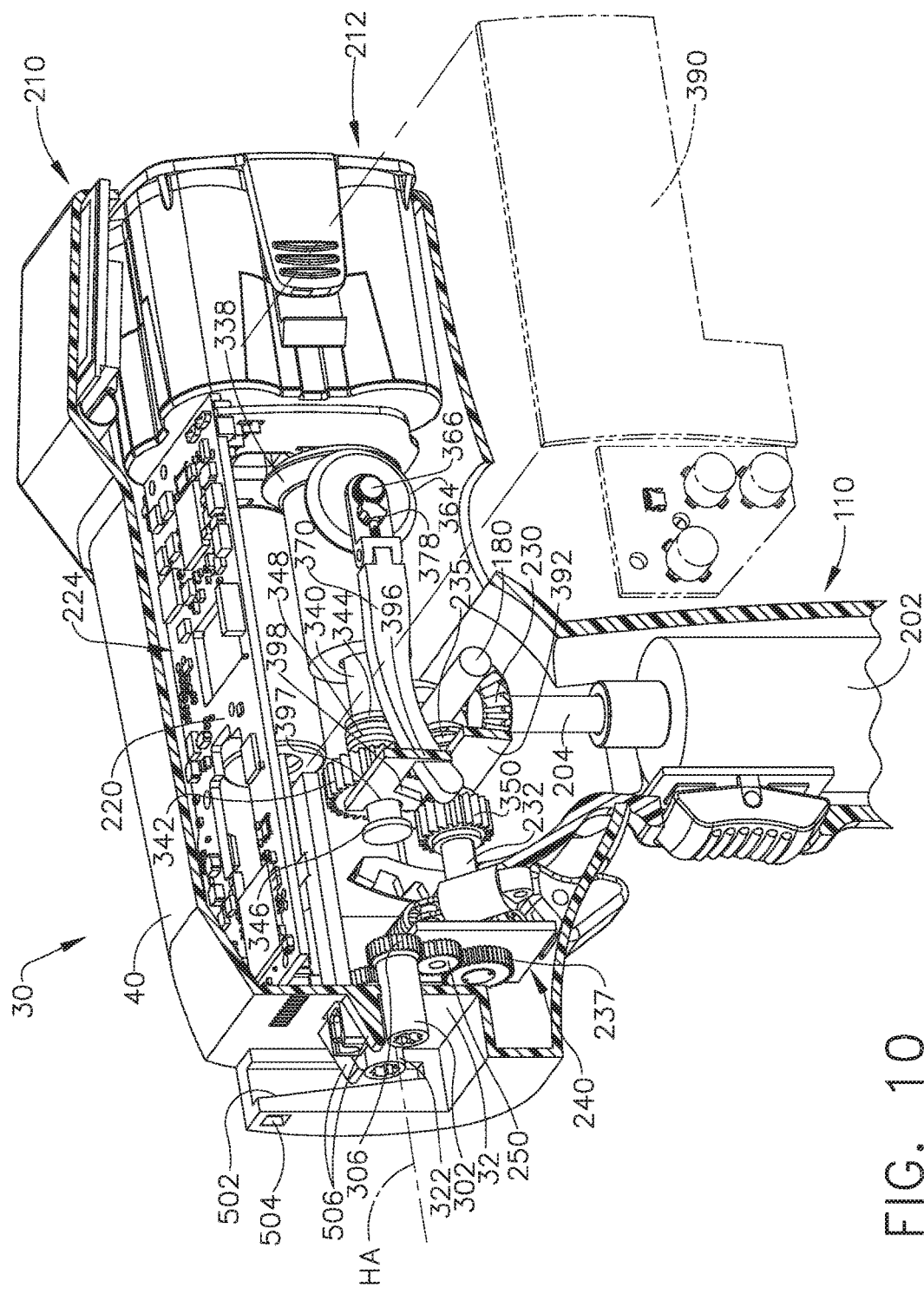
FIG. 10 is another perspective view of the handle assembly of FIGS. 2-9 with certain portions thereof shown in cross-section and with an access panel portion thereof shown in phantom.
Figure 11:
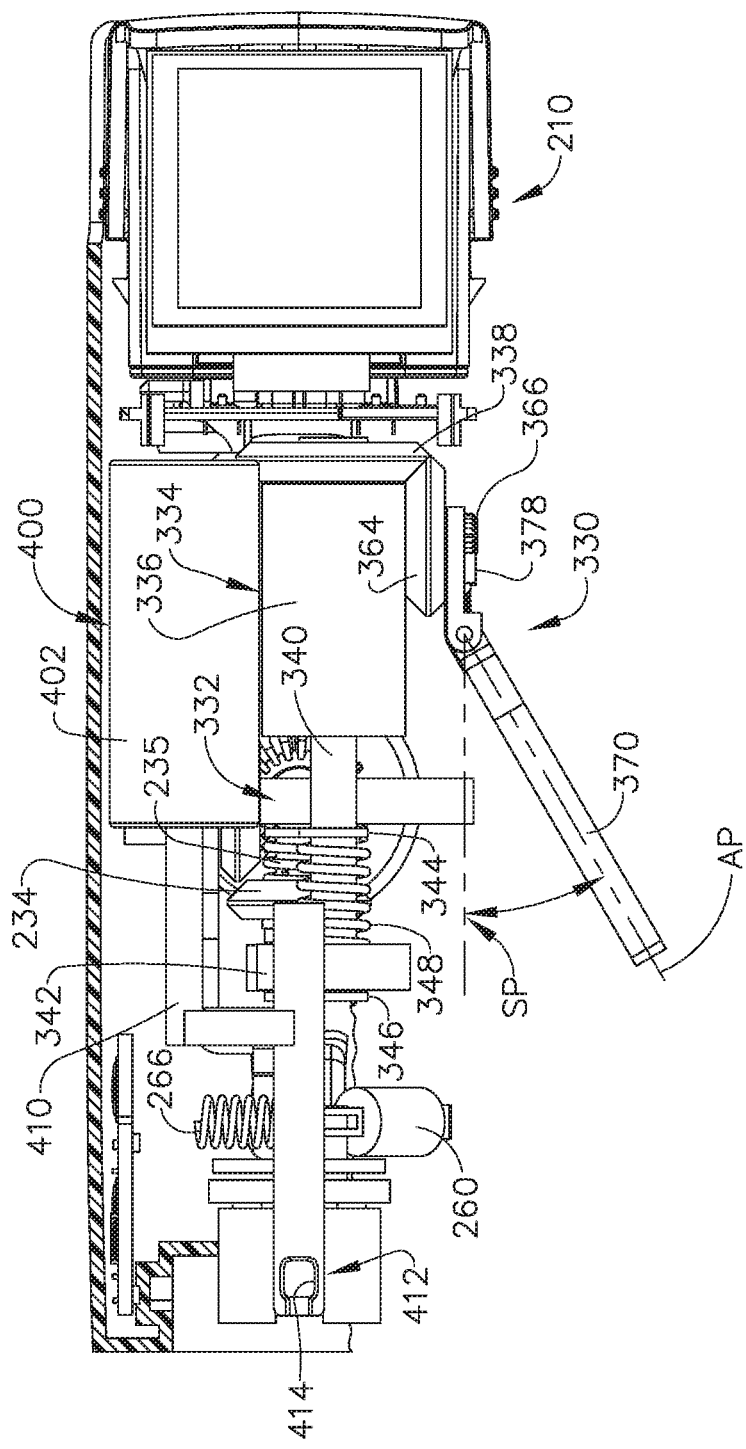
FIG. 11 is a top view of the handle assembly of FIGS. 2-11 with a bailout system shown in an actuatable position.

Referring now to FIGS. 3, 10 and 11, the illustrated bailout system 330 comprises a bailout drive train 332 that includes a planetary gear assembly 334. In at least one form, the planetary gear assembly 334 includes a planetary gear housing 336 that houses a planetary gear arrangement (not shown) that includes a planetary bevel gear 338. The planetary gear assembly 334 includes a bailout drive shaft 340 that is operably coupled to the planetary gear arrangement within the planetary gear housing 336. Rotation of the planetary bevel gear 338 rotates the planetary gear arrangement which ultimately rotates the bailout drive shaft 340. A bailout drive gear 342 is journaled on the bailout drive shaft 340 so that the bailout drive gear 342 can move axially on the bailout drive shaft 340, yet rotate therewith. The bailout drive gear 342 is movable between a spring stop flange 344 that is formed on the bailout drive shaft 340 and a shaft end stop 346 that is formed on the distal end of the bailout drive shaft 340. A bailout shaft spring 348 is journaled on the bailout drive shaft 340 between the bailout drive gear 342 and the spring stop flange 344. The bailout shaft spring 348 biases the bailout drive gear 342 distally on the bailout drive shaft 340. When the bailout drive gear 342 is in its distalmost position on the bail out drive shaft 340, it is in meshing engagement with a bailout driven gear 350 that is non-rotatably mounted to the system drive shaft 232. See FIG. 14.

Figure 12:
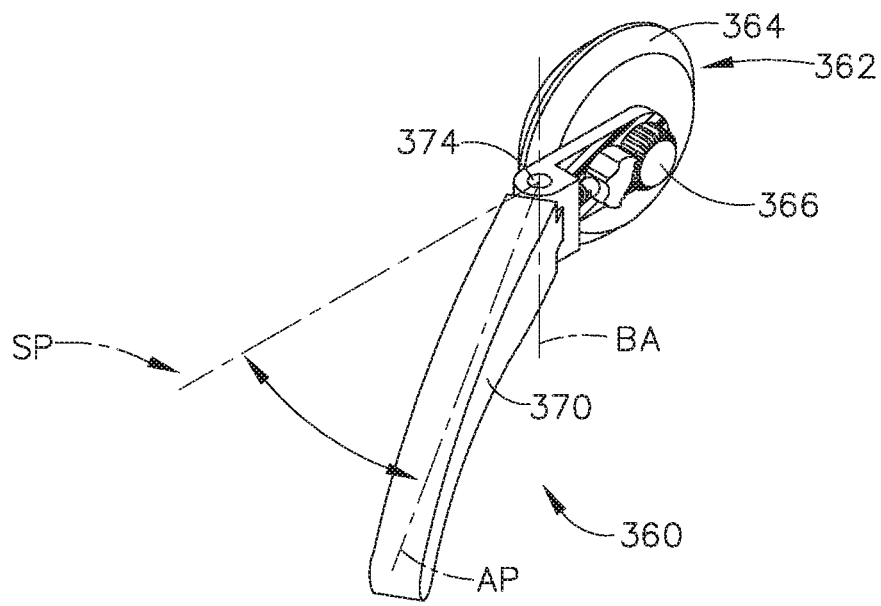
FIG. 12 is a perspective view of a bailout handle of the bailout system depicted in FIGS. 2-11.
Figure 13:
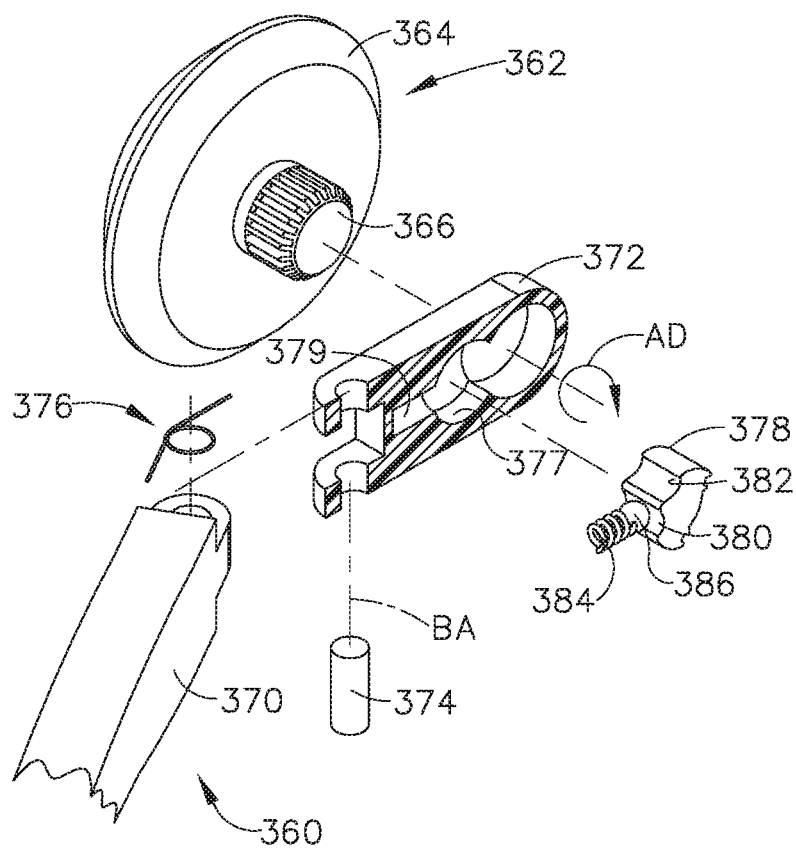
FIG. 13 is an exploded assembly view of portions of the bailout handle of FIG. 12 with portions thereof shown in cross-section.

Referring now to FIGS. 12 and 13, the bailout system 330 includes a bailout actuator assembly or bailout handle assembly 360 that facilitates the manual application of a bailout drive motion to the bailout drive train 332. As can be seen in those Figures, the bailout handle assembly 360 includes a bailout bevel gear assembly 362 that comprises a bailout bevel gear 364 and a ratchet gear 366. The bailout handle assembly 360 further includes a bailout handle 370 that is movably coupled to the bailout bevel gear assembly 362 by a pivot yoke 372 that is pivotally mounted on the ratchet gear 366. The bailout handle 370 is pivotally coupled to the pivot yoke 372 by a pin 374 for selective pivotal travel between a stored position "SP" and an actuation position "AP". See FIG. 12. A handle spring 376 is employed to bias the bailout handle 370 into the actuation position AP. In at least one arrangement, the angle between the axis SP representing the stored position and the axis AP representing the actuation position may be approximately thirty degrees, for example. See FIG. 13. As can also be seen in FIG. 13, the bailout handle assembly 360 further includes a ratchet pawl 378 that is rotatably mounted in a cavity or hole 377 in the pivot yoke 372. The ratchet pawl 378 is configured to meshingly engage the ratchet gear 366 when rotated in an actuation direction "AD" and then rotate out of meshing engagement when rotated in the opposite direction. A ratchet spring 384 and ball member 386 are movably supported in a cavity 379 in the pivot yoke 372 and serve to lockingly engage detents 380, 382 in the ratchet pawl 378 as the bailout handle 370 is actuated (ratcheted).

Referring now to FIGS. 3 and 10, the bailout system 330 further includes a bailout access panel 390 that is maneuverable between an open position and a closed position. In the illustrated arrangement, the bailout access panel 390 is configured to be removably coupled to the housing segment 70 of the primary housing portion 30. Thus, in at least that embodiment, when the bailout access panel 390 is removed or detached from the primary housing portion 30, it is said to be in an "open" position and when the bailout access panel 390 is attached to the primary housing portion 30 as illustrated, it is said to be in a "closed" position. Other embodiments are contemplated, however, wherein the access panel is movably coupled to the primary housing portion such that when the access panel is in the open position, it remains attached thereto. For example, in such embodiments, the access panel may be pivotally attached to the primary housing portion or slidably attached to the primary housing portion and be maneuverable between an open position and a closed position. In the illustrated example, the bailout access panel 390 is configured to snappingly engage corresponding portions of the housing segment 70 to removably retain it in a "closed" position. Other forms of mechanical fasteners such as screws, pins, etc. could also be used.

Regardless of whether the bailout access panel 390 is detachable from the primary housing portion 30 or it remains movably attached to the primary housing portion 30, the bailout access panel 390 includes a drive system locking member or yoke 392 and a bailout locking member or yoke 396 that each protrudes out from the backside thereof or are otherwise formed thereon. The drive system locking yoke 392 includes a drive shaft notch 394 that is configured to receive a portion of the system drive shaft 232 therein when the bailout access panel 390 is installed in the primary housing portion 30 (i.e., the bailout access panel is in the "closed" position). When the bailout access panel 390 is positioned or installed in the closed position, the drive system locking yoke 392 serves to bias the driven bevel gear 234 into meshing engagement with the driver bevel gear 230 (against the bias of the drive system spring 235). In addition, the bailout locking yoke 396 includes a bailout drive shaft notch 397 that is configured to receive a portion of the bailout drive shaft 340 therein when the bailout access panel 390 is installed or positioned in the closed position. As can be seen in FIGS. 5 and 10, the bailout locking yoke 396 also serves to bias the bailout drive gear 342 out of meshing engagement with the bailout driven gear 350 (against the bias of the bailout shaft spring 348). Thus, the bailout locking yoke 396 prevents the bailout drive gear 342 from interfering with rotation of the system drive shaft 232 when the bailout access panel 390 is installed or in the closed position. In addition, the bailout locking yoke 396 includes a handle notch 398 for engaging the bailout handle 370 and retaining it in the stored position SP.

FIGS. 4, 5 and 10 illustrate the configurations of the drive system components and the bailout system components when the bailout access panel 390 is installed or is in the closed position. As can be seen in those Figures, the drive system locking member 392 biases the driven bevel gear 234 into meshing engagement with the driver bevel gear 230. Thus, when the bailout access panel 390 is installed or is in the closed position, actuation of the motor 200 will result in the rotation of the driver bevel gear 230 and ultimately the system drive shaft 232. Also, when in that position, the bailout locking yoke 396 serves to bias the bailout drive gear 342 out of meshing engagement with the bailout driven gear 350 on the system drive shaft 232. Thus, when the bailout access panel 390 is installed or is in the closed position, the drive system is actuatable by the motor 200 and the bailout system 330 is disconnected or prevented from applying any actuation motion to the system drive shaft 232. To activate the bailout system 330, the clinician first removes the bailout access panel 390 or otherwise moves the bailout access panel 390 to the open position. This action removes the drive system locking member 392 from engagement with the driven bevel gear 234 which thereby permits the drive system spring 235 to bias the driven bevel gear 234 out of meshing engagement with the driver bevel gear 230. In addition, removal of the bailout access panel 390 or movement of the bailout access panel to an open position also results in the disengagement of the bailout locking yoke 396 with the bailout drive gear 342 which thereby permits the bailout shaft spring 348 to bias the bailout drive gear 342 into meshing engagement with the bailout driven gear 350 on the system drive shaft 232. Thus, rotation of the bailout drive gear 342 will result in rotation of the bailout driven gear 350 and the system drive shaft 232. Removal of the bailout access panel 390 or otherwise movement of the bailout access panel 390 to an open position also permits the handle spring 376 to bias the bailout handle 370 into the actuation position shown in FIGS. 11 and 14. When in that position, the clinician can manually ratchet the bailout handle 370 in the ratchet directions RD which results in the rotation of the of the ratchet bevel gear 364 (in a clockwise direction in FIG. 14, for example) which ultimately results in the application of a retraction rotary motion to the system drive shaft 232 through the bailout drive train 332. The clinician may ratchet the bailout handle 370 a number of times until the system drive shaft 232 has been sufficiently rotated a number of times to retract a component of the surgical end effector portion of the surgical tool assembly that is attached to the handle assembly 20. Once the bailout system 330 has been sufficiently manually actuated, the clinician may then replace the bailout access panel 390 (i.e., return the bailout access panel 390 to the closed position) to thereby cause the drive system locking member 392 to bias the driven bevel gear 234 into meshing engagement with the driver bevel gear 230 and the bailout locking yoke 396 to bias the bailout drive gear 342 out of meshing engagement with the bailout driven gear 350. As was discussed above, should power be lost or interrupted, the shifter spring 266 will bias the shifter solenoid 260 into the first actuation position. As such, actuation of the bailout system 330 will result in the application of reversing or retraction motions to the first rotary drive system 300.

As discussed above, a surgical stapling instrument can comprise a manually-actuated bailout system configured to retract a staple firing drive, for example. In many instances, the bailout system may need to be operated and/or cranked more than one time to fully retract the staple firing drive. In such instances, the user of the stapling instrument may lose track of how many times they have cranked the bailout and/or otherwise become confused as to how much further the firing drive needs to be retracted. Various embodiments are envisioned in which the stapling instrument comprises a system configured to detect the position of a firing member of the firing drive, determine the distance in which the firing member needs to be retracted, and display that distance to the user of the surgical instrument.

In at least one embodiment, a surgical stapling instrument comprises one or more sensors configured to detect the position of the firing member. In at least one instance, the sensors comprise Hall Effect sensors, for example, and can be positioned in a shaft and/or end effector of the stapling instrument. The sensors are in signal communication with a controller of the surgical stapling instrument which is, in turn, in signal communication with a display on the surgical stapling instrument. The controller comprises a microprocessor configured to compare the actual position of the firing member to a datum, or reference, position—which comprises a fully retracted position of the firing member—and calculate the distance, i.e., the remaining distance, between the actual position of the firing member and the reference position.

Further to the above, the display comprises an electronic display, for example, and the controller is configured to display the remaining distance on the electronic display in any suitable manner. In at least one instance, the controller displays a progress bar on the display. In such instances, an empty progress bar can represent that the firing member is at the end of its firing stroke and a full progress bar can represent that the firing member has been fully retracted, for example. In at least one instance, 0% can represent that the firing member is at the end of its firing stroke and 100% can represent that the firing member has been fully retracted, for example. In certain instances, the controller is configured to display how many actuations of the bailout mechanism are required to retract the firing member to its fully retracted position on the display.

Further to the above, the actuation of the bailout mechanism can operably disconnect a battery, or power source, of the surgical stapling instrument from an electric motor of the firing drive. In at least one embodiment, the actuation of the bailout mechanism flips a switch which electrically decouples the battery from the electric motor. Such a system would prevent the electric motor from resisting the manual retraction of the firing member.

The illustrated handle assembly 20 also supports a third axial drive system that is generally designated as 400. As can be seen in FIGS. 3 and 4, the third axial drive system 400, in at least one form, comprises a solenoid 402 that has a third drive actuator member or rod 410 protruding therefrom. The distal end 412 of the third drive actuator member 410 has a third drive cradle or socket 414 formed therein for receiving a corresponding portion of a drive system component of an interchangeable surgical tool assembly that is operably attached thereto. The solenoid 402 is wired to or otherwise communicates with the handle circuit board assembly 220 and the control system or CPU 224. In at least one arrangement, the solenoid 402 is "spring loaded" such that when the solenoid 402 is unactuated, the spring component thereof biases the third drive actuator 410 back to an unactuated starting position.

As indicated above, the reconfigurable handle assembly 20 may be advantageously employed to actuate a variety of different interchangeable surgical tool assemblies. To that end, the handle assembly 20 includes a tool mounting portion that is generally designated as 500 for operably coupling an interchangeable surgical tool assembly thereto. In the illustrated example, the tool mounting portion 500 includes two inwardly facing dovetail receiving slots 502 that are configured to engage corresponding portions of a tool attachment module portion of the interchangeable surgical tool assembly. Each dovetail receiving slot 502 may be tapered or, stated another way, be somewhat V-shaped. The dovetail receiving slots 502 are configured to releasably receive corresponding tapered attachment or lug portions that are formed on a portion of the tool attachment nozzle portion of the interchangeable surgical tool assembly. Each interchangeable surgical tool assembly may also be equipped with a latching system that is configured to releasable engage corresponding retention pockets 504 that are formed in the tool mounting portion 500 of the handle assembly 20.

The various interchangeable surgical tool assemblies may have a "primary" rotary drive system that is configured to be operably coupled to or interface with the first rotary drive system 310 as well as a "secondary" rotary drive system that is configured to be operably coupled to or interface with the second rotary drive system 320. The primary and secondary rotary drive systems may be configured to provide various rotary motions to portions of the particular type of surgical end effector that comprises a portion of the interchangeable surgical tool assembly. To facilitate operable coupling of the primary rotary drive system to the first rotary drive system and the secondary drive system to the second rotary drive system 320, the tool mounting portion 500 of the handle assembly 20 also includes a pair of insertion ramps 506 that are configured to bias portions of the primary and secondary rotary drive systems of the interchangeable surgical tool assembly distally during the coupling process so as to facilitate alignment and operable coupling of the primary rotary drive system to the first rotary drive system 300 on the handle assembly 20 and the secondary rotary drive system to the second rotary drive system 320 on the handle assembly 20.

The interchangeable surgical tool assembly may also include a "tertiary" axial drive system for applying axial motion(s) to corresponding portions of the surgical end effector of the interchangeable surgical tool assembly. To facilitate operable coupling of the tertiary axial drive system to the third axial drive system 400 on the handle assembly 20, the third drive actuator member 410 is provided with a socket 414 that is configured to operably receive a lug or other portion of the tertiary axial drive system therein.

Interchangeable Surgical Tool Assembly

Figure 15:
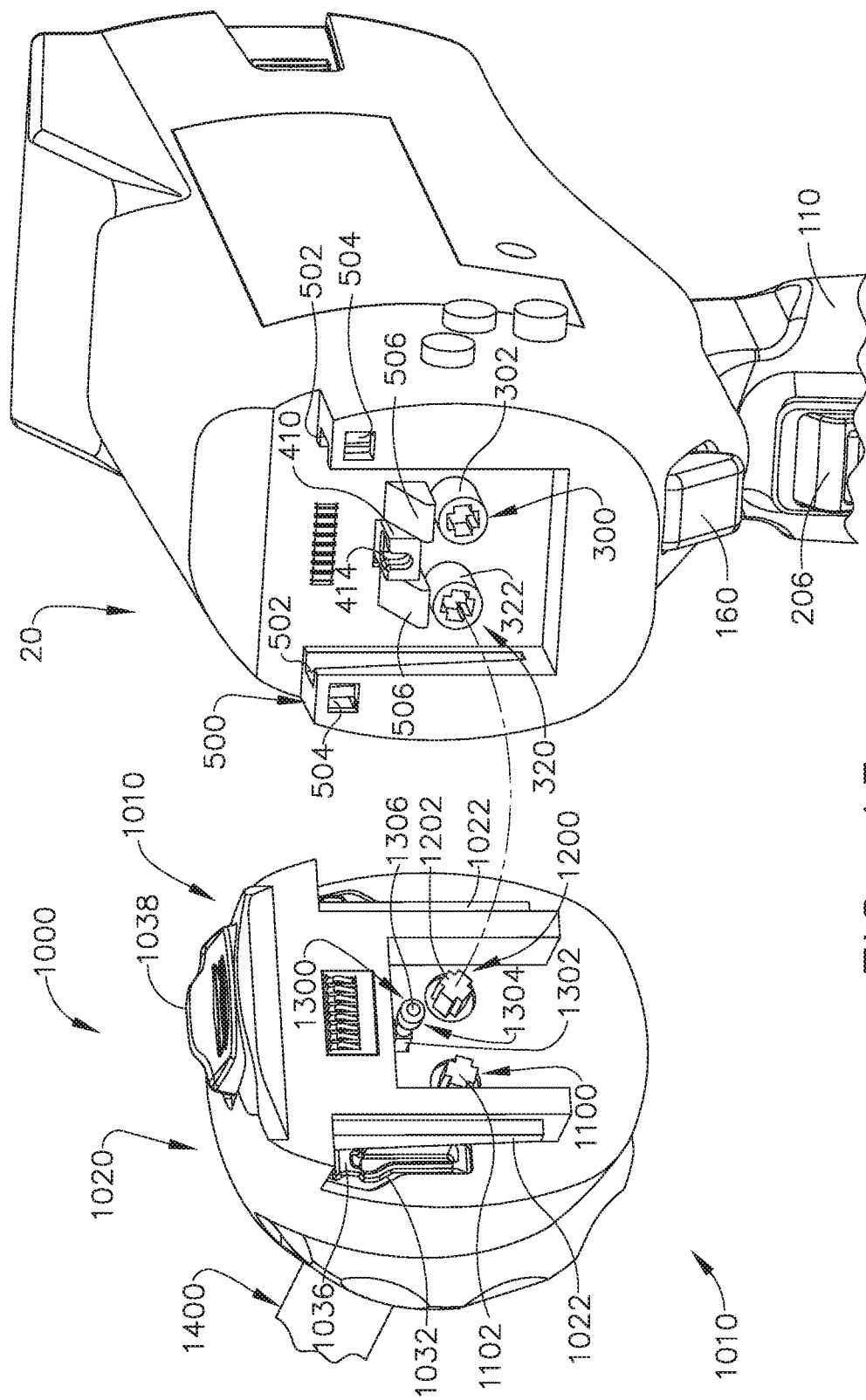
FIG. 15 is a perspective view of the handle assembly of FIGS. 2-11 and a tool attachment module portion of the interchangeable surgical tool assembly of FIG. 1.

FIG. 15 illustrates use of an interchangeable surgical tool assembly 1000 that may be used in connection with the handle assembly 20. As can be seen in that Figure, for example, the interchangeable surgical tool assembly 1000 includes a tool attachment module 1010 that is configured for operable and removable attachment to the tool mounting portion 500 of the handle assembly 20. The tool attachment module 1010 in the illustrated arrangement includes a nozzle frame 1020. In the illustrated arrangement, the interchangeable surgical tool assembly 1000 includes a primary rotary drive system 1100 and a secondary rotary drive system 1200. The primary rotary drive system 1100 is configured to operably interface with the first rotary drive system 300 on the handle assembly 20 and apply rotary firing motions to the surgical end effector 1500 attached thereto as will be discussed in further detail below. The secondary rotary drive system 1200 is configured to operably interface with the second rotary drive system 320 on the handle assembly 20 and apply articulation control motions to an articulation system 1700. The articulation system 1700 couples the surgical end effector 1500 to an elongate shaft assembly 1400 that is coupled to the nozzle frame 1020. The interchangeable surgical tool assembly 1000 further includes a tertiary drive system 1300 that is configured to operably interface with the third axial drive system 400 in the handle assembly 20. The tertiary axial drive system 1300 of the surgical tool assembly comprises a tertiary actuation shaft 1302 that has a shaft attachment lug 1306 formed on the proximal end 1304 thereof. As will be discussed in further detail below, when the interchangeable surgical tool assembly 1000 is coupled to the handle assembly 20, the shaft attachment lug 1306 is received in the shaft attachment socket 414 on the distal end 412 of the third drive actuator member 410.

Figure 18:
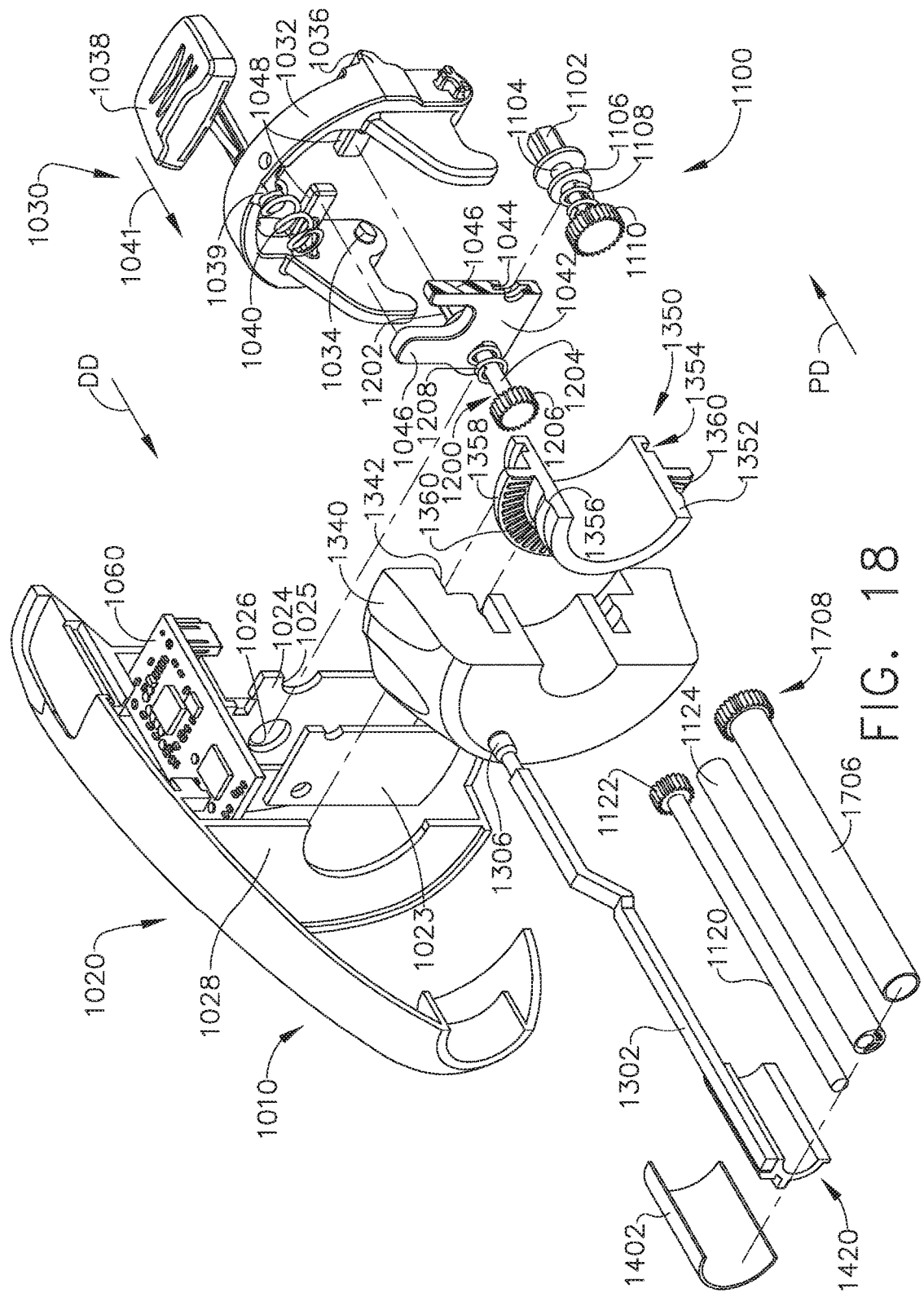
FIG. 18 is an exploded assembly view of the tool attachment module of FIG. 16.

Still referring to FIG. 15, the reader will observe that the tool mounting portion 500 of the handle assembly 20 includes two inwardly facing dovetail receiving slots 502. Each dovetail receiving slot 502 may be tapered or, stated another way, be somewhat V-shaped. The dovetail receiving slots 502 are configured to releasably receive corresponding tapered attachment or lug portions 1022 formed on the nozzle frame 1020. Turning next to FIG. 18, in at least one form, the tool attachment module 1010 is removably latched to the tool mounting portion 500 of the handle assembly 20 by a latching system generally designated as 1030. In the illustrated embodiment, the latching system 1030 comprises a lock yoke 1032 that includes a pair of inwardly extending pivot pins 1034 (only one is shown in FIG. 18) that are received in corresponding pivot holes (not shown) in the nozzle frame 1020. Such arrangement serves to pivotally or movably couple the lock yoke 1032 to the nozzle frame 1020. The lock yoke 1032 further includes a pair of retention lugs or hook formations 1036 (only one can be seen in FIG. 18) that are configured to be hookingly or otherwise retainingly received in corresponding retention pockets 504 that are formed in the tool mounting portion 500 of the handle assembly 20. The lock yoke 1032 may be pivoted out of retaining engagement by applying an unlocking motion (represented by arrow 1041 in FIGS. 18, 20 and 21) to a release button 1038 that is attached to the lock yoke 1032. A lock yoke spring 1040 is received on a spring lug 1039 that is formed on the lock yoke 1032 and a spring mounting lug 1021 that is formed on the nozzle frame 1020. The lock yoke spring 1040 serves to bias the lock yoke 1032 into the locked position.

Figure 19:
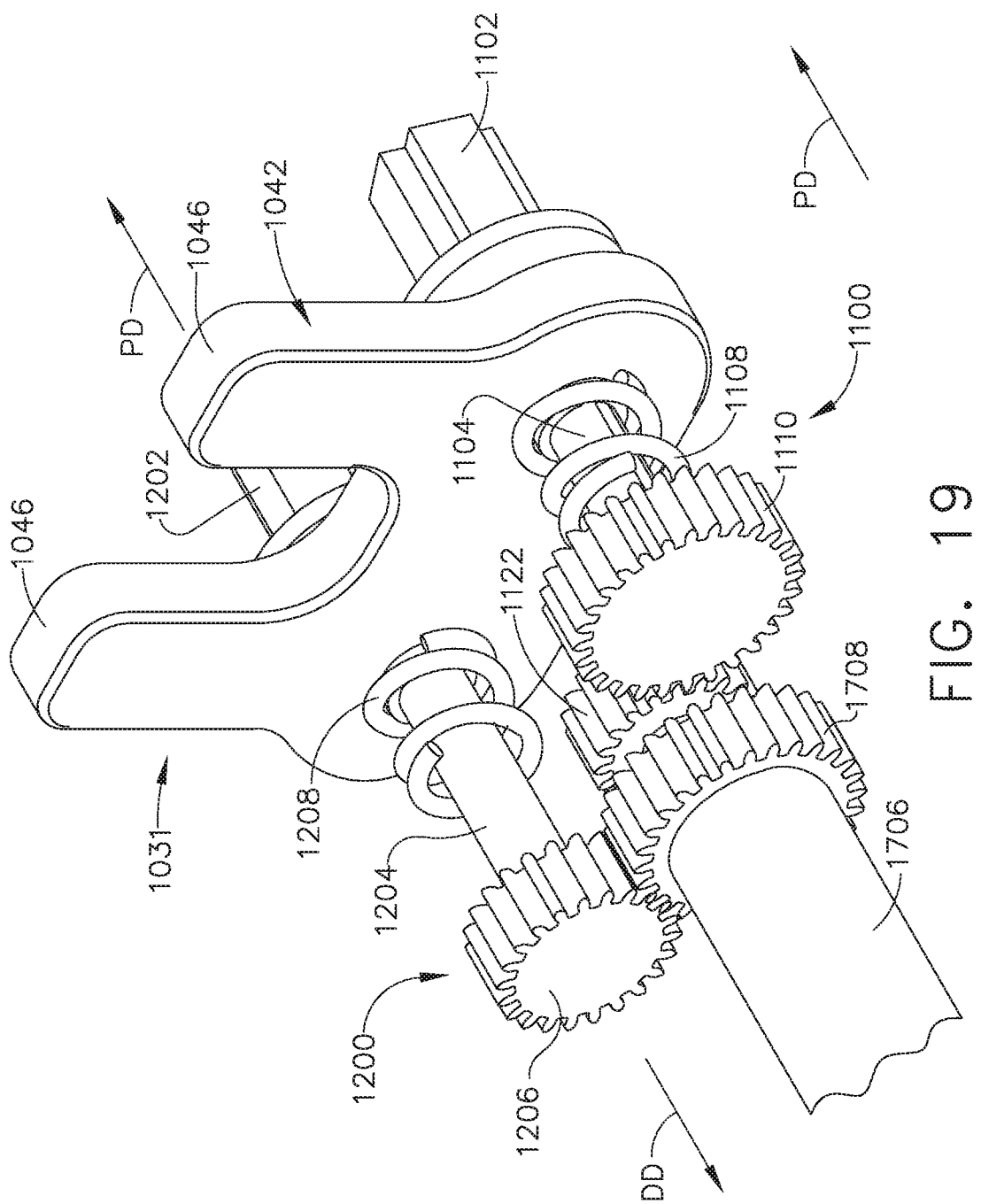
FIG. 19 is a perspective view of one form of a shaft coupler release assembly.

The latching system 1030 of the illustrated example further comprises a shaft coupler release assembly 1031 for releasably engaging the primary rotary drive system 1100 to the first rotary drive system 300 as well as the secondary rotary drive system 1200 to the second rotary drive system 320 on the handle assembly 20. Referring now to FIGS. 18 and 19, the primary rotary drive system 1100 includes a primary drive key 1102 that is configured to be axially received within the first drive socket 302 of the first rotary drive system 300. The primary drive key 1102 is slidably received on a primary transfer shaft 1104 that is rotatably supported by a bulkhead 1023 that is formed in the nozzle frame 1020. The primary drive key 1102 also movably extends through a hole 1025 in another bulkhead 1024 that is formed in the nozzle frame 1020. See FIG. 18. The primary transfer shaft 1104 is splined so that the primary drive key 1102 is free to axially move on the primary transfer shaft 1104 but not rotate relative thereto such that rotation of the primary drive key 1102 results in rotation of the primary transfer shaft 1104. As can be further seen in FIG. 18, the primary drive key 1102 includes an attachment flange 1106 that is received within a cavity 1044 in a coupler release tab 1042. Thus, the primary drive key 1102 and the coupler release tab 1042 move as a unit. A primary transfer spring 1108 is journaled on the primary transfer shaft 1104 and extends between the bulkhead 1023 and the coupler release tab 1042 to bias the coupler release tab 1042 and the primary drive key 1102 in the proximal direction "PD" on the primary transfer shaft 1104.

Still referring to FIGS. 18 and 19, the secondary rotary drive system 1200 includes a secondary drive key 1202 that is configured to be axially received within the second drive socket 322 of the second rotary drive system 320. The secondary drive key 1202 is slidably received on a secondary transfer shaft 1204 that is rotatably supported by the bulkhead 1023. The secondary drive key 1202 also movably extends through a hole 1026 in bulkhead 1024. The secondary transfer shaft 1204 is splined so that the secondary drive key 1202 is free to axially move on the secondary transfer shaft 1204 but not rotate relative thereto such that rotation of the secondary drive key 1202 results in rotation of the secondary transfer shaft 1204. The secondary drive key 1202 includes an attachment flange (not shown) that is received within a cavity (not shown) in the coupler release tab 1042.

Thus, the secondary drive key 1202 and the coupler release tab 1042 move as a unit. A secondary transfer spring 1208 is journaled on the secondary transfer shaft 1204 and extends between the bulkhead 1023 and the coupler release tab 1042 to bias the coupler release tab 1042 and the secondary drive key 1202 in the proximal direction PD on the secondary transfer shaft 1204. As can be seen in FIG. 18, the coupler release tab 1042 is formed with two upstanding actuator portions 1046 that correspond to inwardly extending coupler release tabs 1048 formed on the lock yoke 1032.

Figure 20:
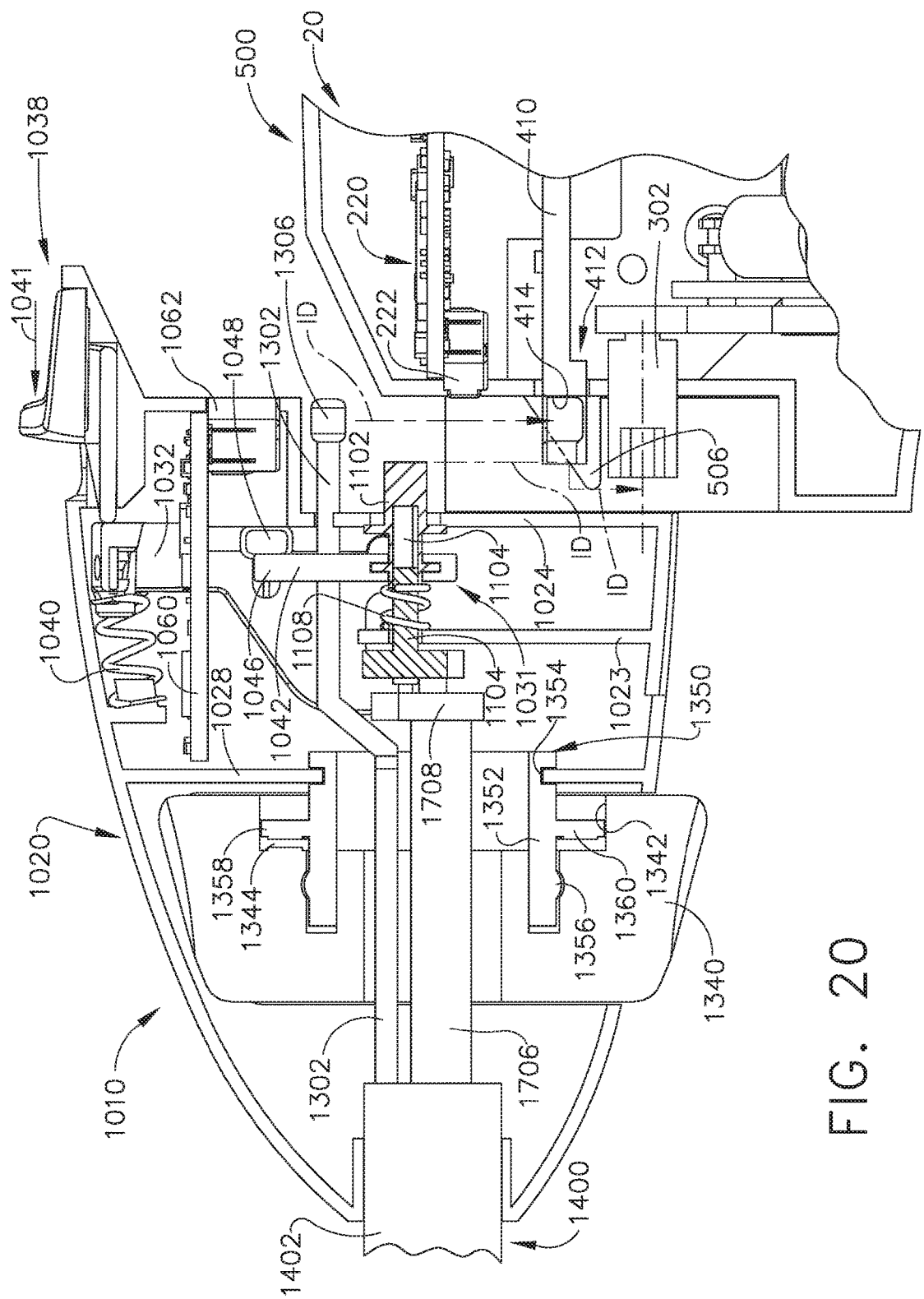
FIG. 20 is a side cross-sectional view of the tool attachment module of FIGS. 16 and 18 being aligned for installation on a tool mounting portion of the handle assembly of FIG. 1.
Figure 21:
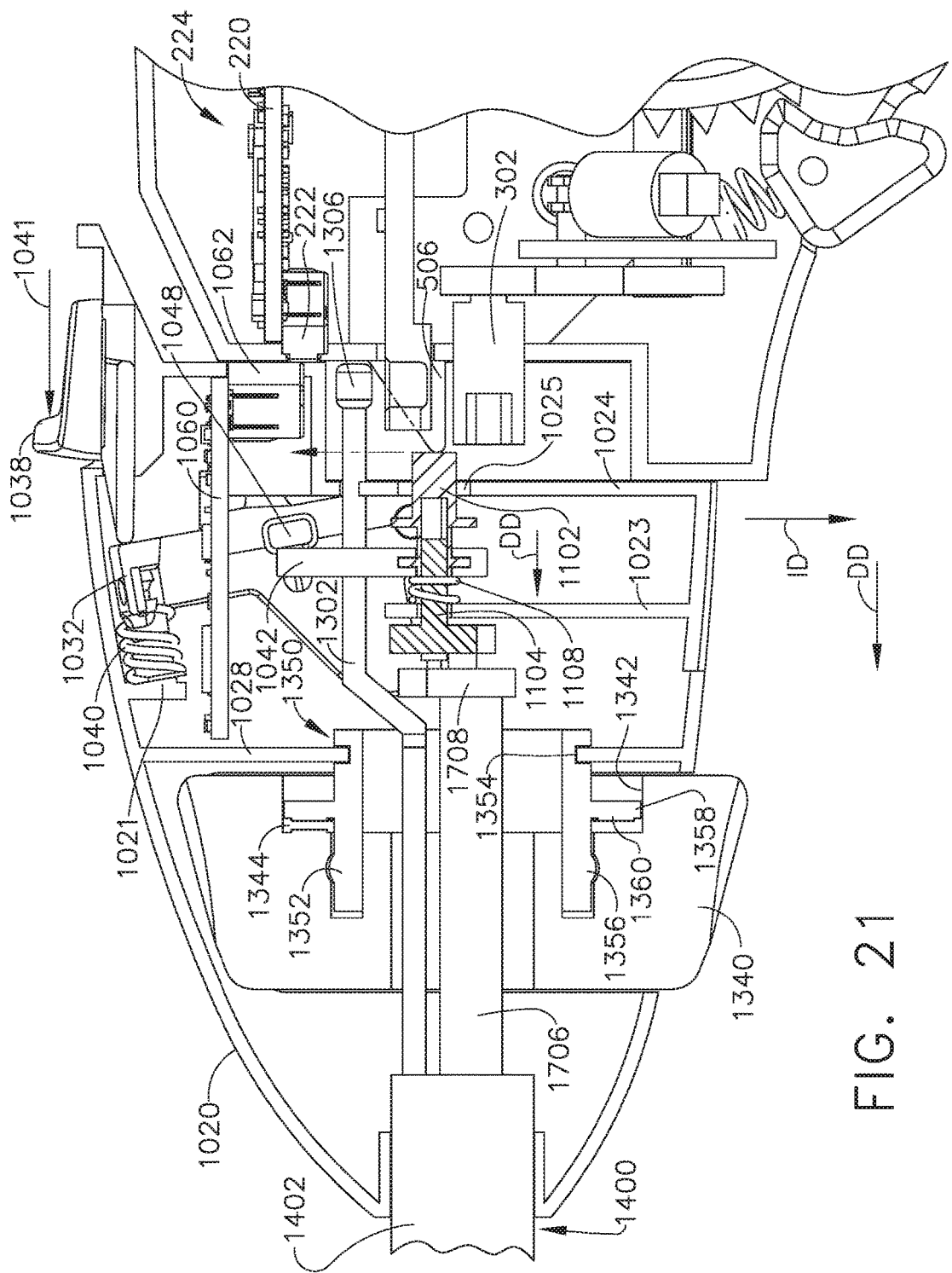
FIG. 21 is another side cross-sectional view of the tool attachment module of FIG. 20 being initially inserted into tool mounting portion of the handle assembly of FIG. 1.
Figure 22:
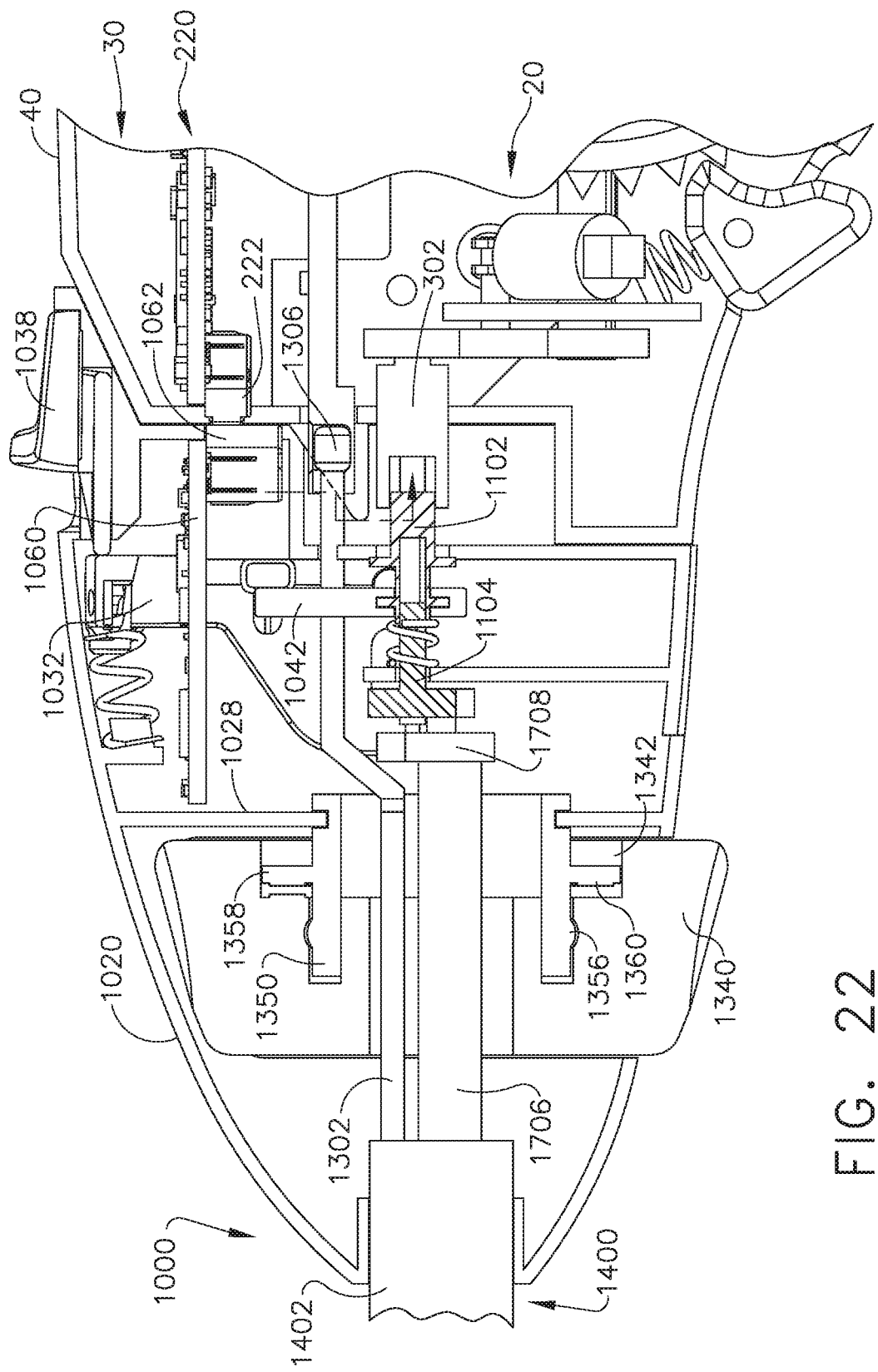
FIG. 22 is another side cross-sectional view of the tool attachment module of FIGS. 20 and 21 attached to the tool mounting portion of the handle assembly of FIG. 1.

Operation of the latching system 1030 may be understood from reference to FIGS. 20-22. FIG. 20 illustrates the beginning of the coupling process wherein the interchangeable surgical tool assembly 1000 is moved in the installation direction "ID" relative to the handle assembly 20. To commence the installation process, the clinician aligns the tapered attachment lugs 1022 on the nozzle frame 1020 with their corresponding dovetail slot 502 on the tool mounting portion 500 of the handle assembly 20 and moves the interchangeable surgical tool assembly 1000 in the insertion direction ID relative to the handle assembly 20. Insertion and movement of the tapered attachment lugs 1022 in their respective dovetail slot 502 serves to align the shaft attachment lug 1306 on the tertiary actuation shaft 1302 with the shaft attachment socket 414 on the distal end 412 of the third drive actuator member 410. Likewise, the primary drive key 1102 and the secondary drive key 1202 are each aligned for contact with corresponding insertion ramps 506 that are formed on the tool mounting portion 500 of the handle assembly 20.

FIG. 21 illustrates contact between the primary drive key 1102 and the corresponding insertion ramp 506 with it being understood that the secondary drive key 1202 would be in a similar position with its corresponding insertion ramp 506. As can be seen in that Figure, the primary drive key 1102 has contacted the insertion ramp 506 and continued advancement of the interchangeable surgical tool assembly 1000 in the installation direction ID causes the insertion ramp 506 to bias the primary drive key 1102 in the distal direction DD on the primary transfer shaft 1104. The secondary drive key 1202 would similarly move in the distal direction DD on the secondary transfer shaft 1204. This movement may be further achieved by pushing the release button 1038 in the direction represented by arrow 1041 which causes the lock yoke 1032 to contact the coupler release tab 1042 and move it in the distal direction DD against the biasing force of the first and second transfer springs 1108, 1208. The clinician may maintain the pressure on the release button 1038 so that once the primary drive key 1102 and secondary drive key 1202 clear their corresponding insertion ramps 506, the primary drive key 1102 and secondary drive key 1202 can move into alignment with the corresponding first and second drive sockets 302, 322, respectively. When the tapered attachment lugs 1022 are seated in their respective dovetail slots 502, the primary drive key 1102 is axially aligned with the first drive socket 302 and the secondary drive key 1202 is axially aligned with the second drive socket 322, such that when the clinician releases the release button 1038, the primary drive key 1102 enters the first drive socket 302 and the secondary drive key 1202 enters the second drive socket 322. See FIG. 22. Thus, rotation of the first drive socket 302 will result in rotation of the primary drive key 1102 and the primary transfer shaft 1104 and rotation of the second drive socket 322 will result in rotation of the secondary drive key 1202 and the secondary transfer shaft 1204. In addition, the shaft attachment lug 1306 is received within the shaft attachment socket 414 on the distal end 412 of the third drive actuator member 410. Thus, axial movement of the third drive actuator member 410 will result in the axial movement of the tertiary actuation shaft 1302. As can also be seen in FIGS. 20-22, the interchangeable surgical tool assembly 1000 further includes an onboard "tool" circuit board 1060 that has a connector portion 1062 that is configured to mate with a corresponding connector 222 on the handle circuit board 220. When the tool circuit board 1060 is coupled to the handle circuit board 220, the tool circuit board provides an identification signal to the control system or CPU 224 so that the control system or CPU 224 can select the appropriate control actions for the type of interchangeable surgical tool assembly that is being employed.

End Effectors

Figure 23:
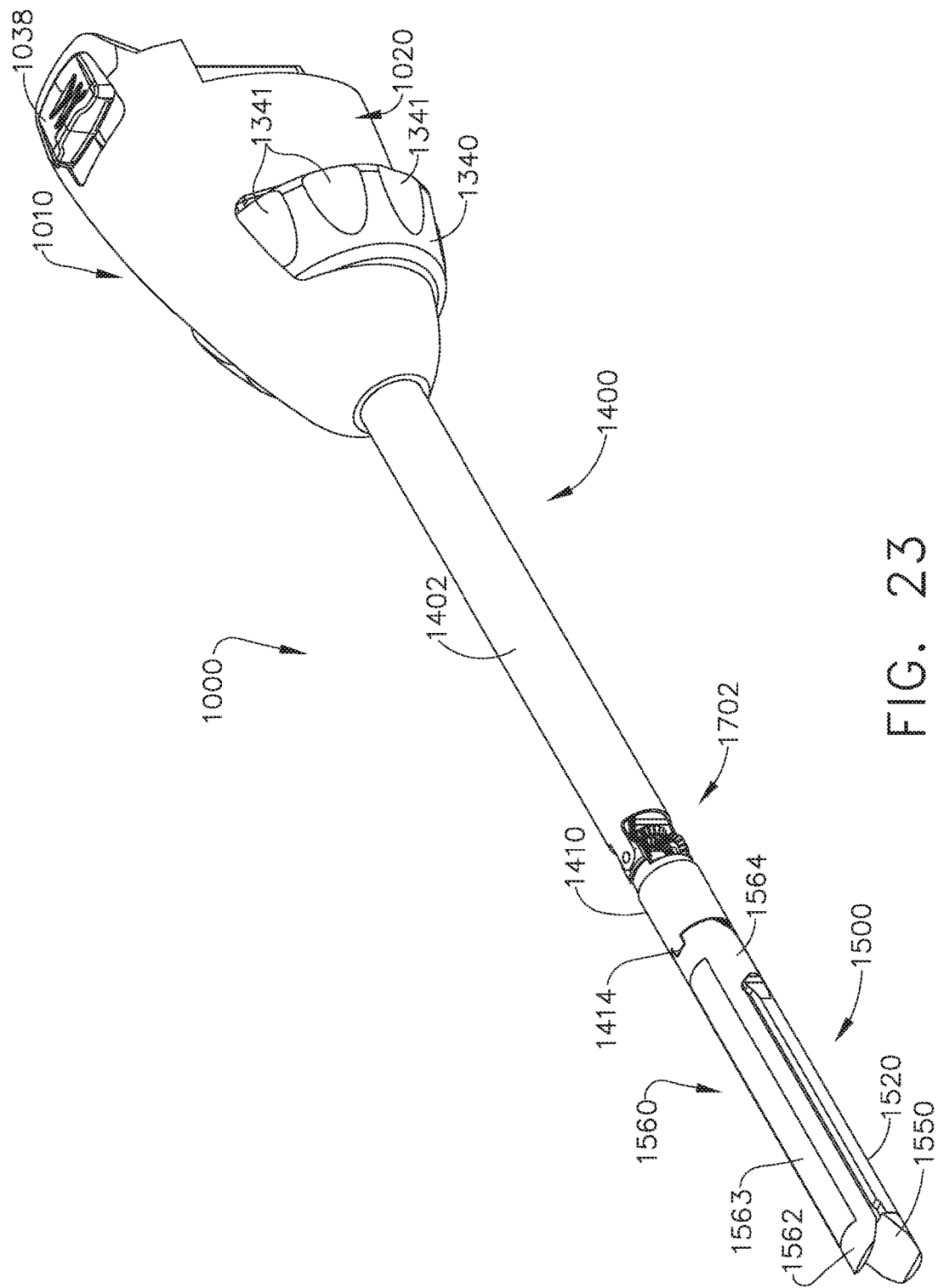
FIG. 23 is a perspective view of the interchangeable surgical tool assembly of FIG. 1.
Figure 24:
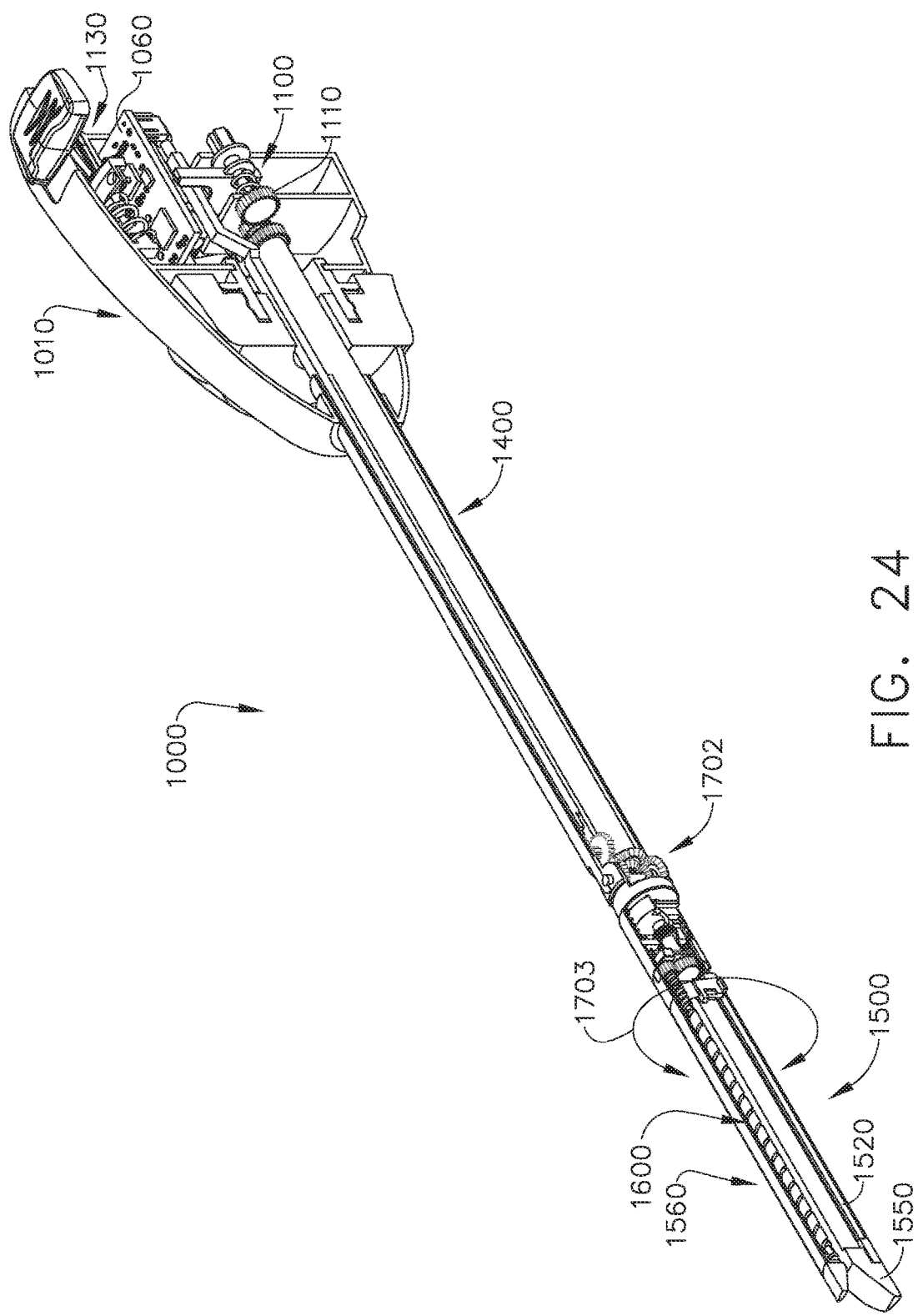
FIG. 24 is a cross-sectional perspective view the interchangeable surgical tool assembly of FIG. 23.
Figure 25:
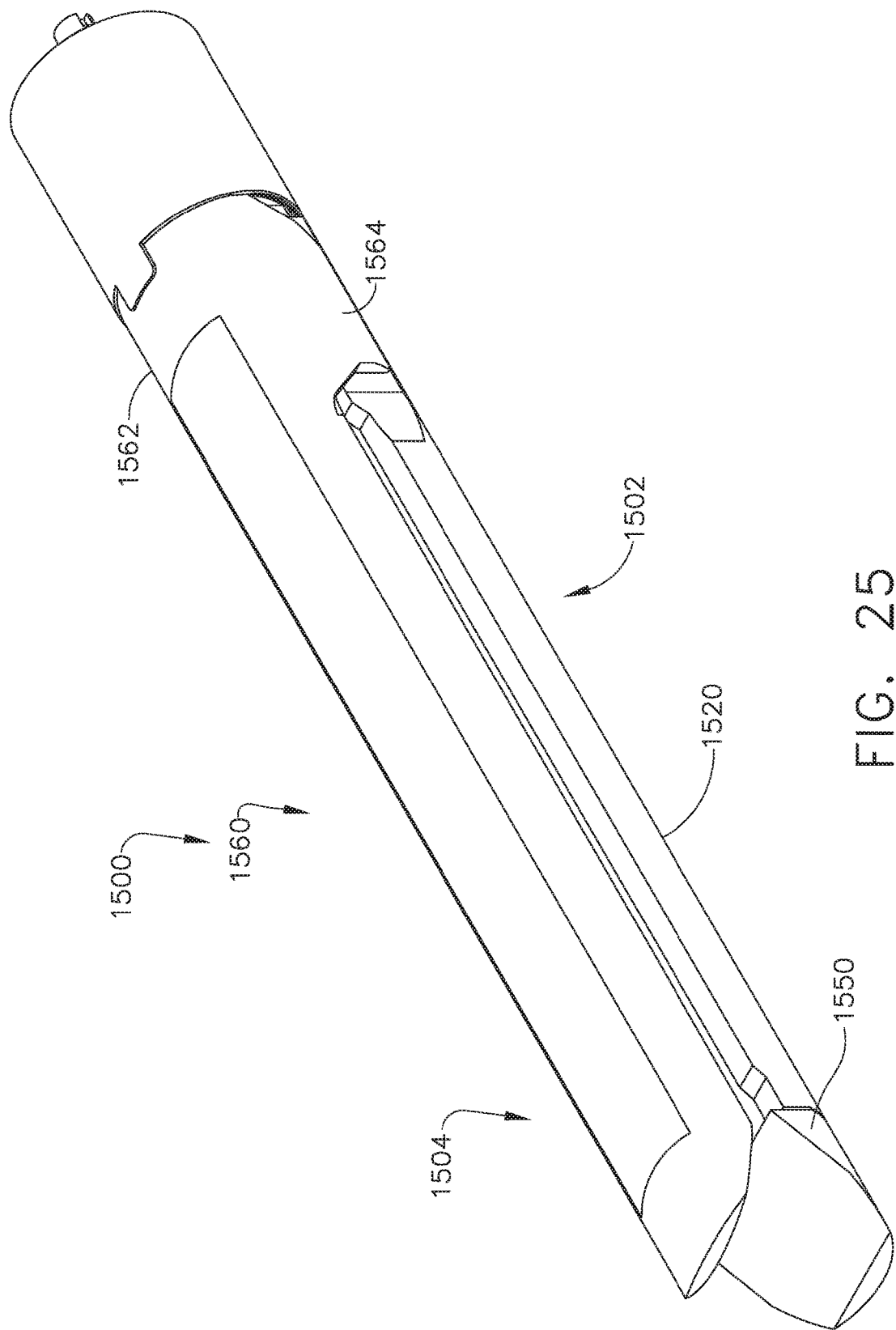
FIG. 25 is a perspective view of a surgical end effector portion of the interchangeable surgical tool assembly of FIG. 23.

The interchangeable surgical tool assembly 1000 includes a surgical end effector 1500 that is configured to cut and fasten tissue. As can be seen in FIGS. 23 and 24, the surgical end effector 1500 is operably coupled to an elongate shaft assembly 1400 by an articulation joint 1702. As will be discussed in further detail below, the elongate shaft assembly 1400 is operably coupled to the tool attachment module 1010 and comprises portions of the primary rotary drive system 1100, the secondary rotary drive system 1200 and the tertiary axial drive system 1300. Referring now to FIGS. 25-28, the surgical end effector 1500 includes an elongate channel 1520 that is configured to operably support a surgical staple cartridge 1550 therein. The surgical staple cartridge 1550 may comprise a compressible or implantable staple cartridge that has a body portion 1552 that consists of a compressible hemostat material such as, for example, oxidized regenerated cellulose ("ORC") or a bio-absorbable foam in which lines of unformed metal staples or other forms of fasteners are supported. In at least some embodiments, in order to prevent the staple from being affected and the hemostat material from being activated during the introduction and positioning process, the entire cartridge may be coated and/or wrapped in a biodegradable film such as a polydioxanon film, sold under the trademark PDS®, a polyglycerol sebacate (PGS) film, and/or other biodegradable films formed from PGA (polyglycolic acid), PCL (polycaprolactone), PLA or PLLA (polylactic acid), PHA (polyhydroxyalkanoate), PGCL (poliglecaprone 25) and/or a composite of PGA, PCL, PLA, PDS, for example, that would be impermeable until ruptured. Varieties of different implantable cartridge arrangements are known and may be employed. For example, various implantable/compressible cartridge arrangements are disclosed in further detail in many of the patent applications and patents that have been incorporated by reference herein in their respective entireties. In the illustrated example, the cartridge body portion 1552 of surgical staple cartridge 1550 is sized to be removably supported within the elongate channel 1520.

The elongate channel 1520 and surgical staple cartridge 1550 installed therein may also be referred to herein a "first jaw" 1502. The surgical end effector 1500 also includes a second jaw 1504 in the form of an anvil assembly 1560 that is supported for movable travel relative to the first jaw. Stated another way, the first and second jaws 1502 and 1504 may be configured for movable travel relative to each other between open positions and closed positions. In the illustrated arrangement, the anvil assembly 1560 comprises an anvil body portion or anvil frame 1562. The anvil frame 1562 includes a proximal anvil portion 1570 that has a pair of trunnion pins 1572 extending laterally therefrom. The trunnion pins 1572 are movably received in pivot slots 1526 that are formed in corresponding upstanding walls 1524 of a channel mounting portion 1522 of the elongate channel

1520. See FIGS. 27 and 28. The anvil frame 1562, in at least one form, includes a pair of downwardly extending tissue stops 1564 that serve to limit the distance in which the target tissue may extend proximally between the first and second jaws 1502, 1504 so that when the target tissue is severed, the fasteners are properly positioned to fasten the cut tissue. When the first and second jaws 1502, 1504 are in the closed position, the tissue stops 1564 are outside of the upstanding walls 1524 of the channel mounting portion 1522 and the proximal anvil portion 1570 is located between the upstanding walls 1524. See FIG. 28.

Anvil Concentric Drive Member

Figure 26:
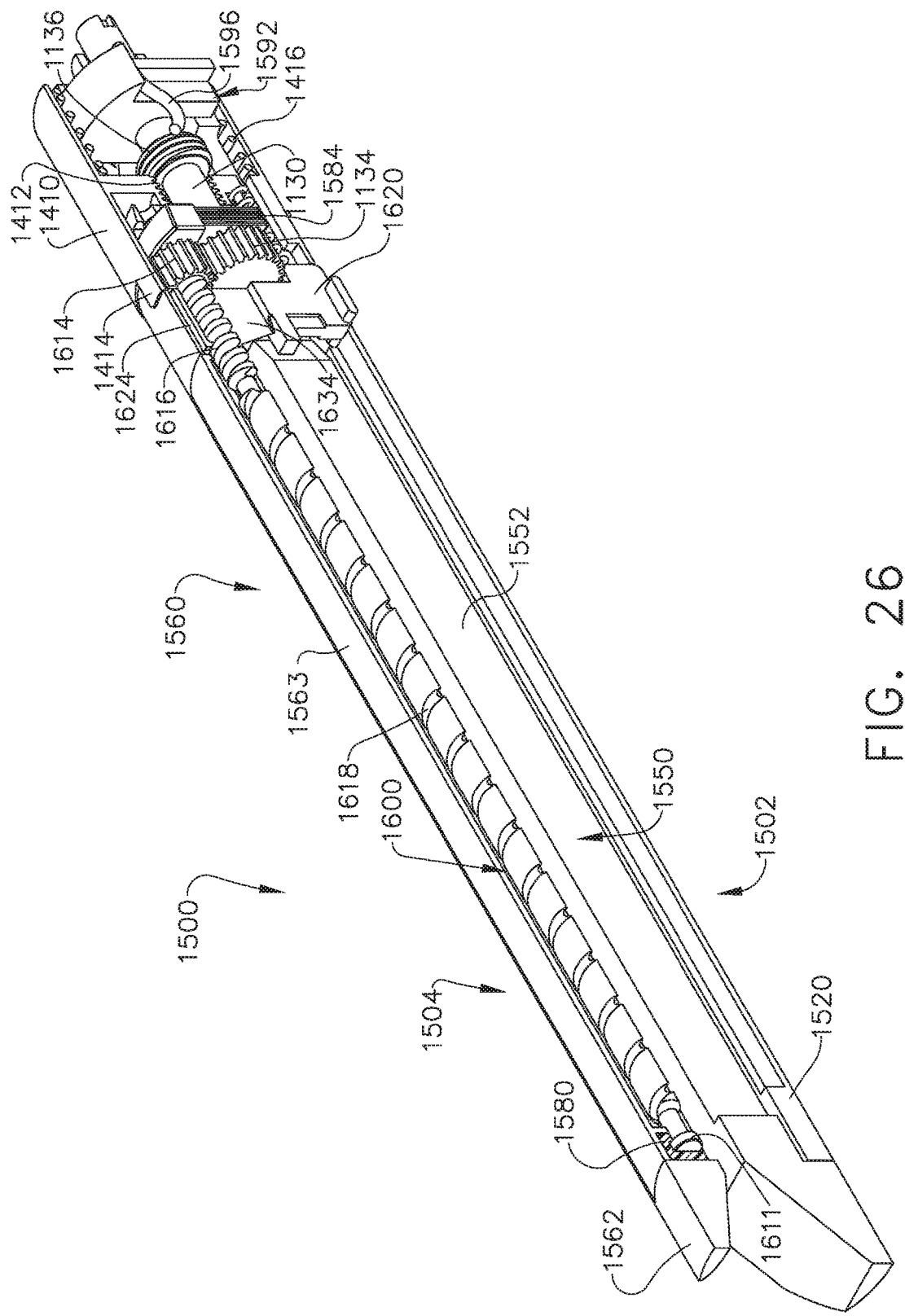
FIG. 26 is a cross-sectional perspective view of the surgical end effector of FIG. 25.

The anvil assembly 1560 operably supports an anvil concentric drive member 1600 for operably driving a firing member 1620 through the end effector 1500. The anvil concentric drive member 1600 may, for example, be centrally disposed within the anvil frame 1562 and substantially extend the length thereof. The anvil concentric drive member 1600 in the illustrated embodiment comprises an anvil drive shaft 1610 that includes a distal bearing lug 1611 and a proximal bearing lug 1612. The distal bearing lug 1611 is rotatably housed in a distal bearing housing 1580 that is supported in a bearing pocket in the anvil frame 1562. The proximal bearing lug 1612 is rotatably supported in the anvil assembly 1560 by a floating bearing housing 1582 that is movably supported in a bearing pocket 1574 that is formed in the proximal anvil portion 1570. See FIG. 27. The proximal and distal bearing housing arrangements may serve to prevent or at least minimize an occurrence of compressive forces on the anvil drive shaft 1610 which might otherwise cause the anvil drive shaft 1610 to buckle under high force conditions. The anvil drive shaft 1610 further includes a driven firing gear 1614, a proximal threaded or helix section 1616 and a distal threaded or helix section 1618. In the illustrated arrangement, the proximal threaded section 1616 has a first length "FL" and the distal threaded section 1618 has a distal length "DL" that is greater than the first length FL. In at least one arrangement, for example, the first length FL may be approximately 3-5 threads per inch using only one acme thread lead and the distal length DL may be approximately 9-15 threads per inch with 2-4 acme thread leads for more power. However, the proximal threaded section 1616 and the distal threaded section 1618 may have other lengths. See FIG. 31. As can be seen in FIG. 26, the pitch of the distal threaded section 1618 is greater than the pitch of the proximal threaded section 1616. Stated another way, the lead of the distal threaded section 1618 is greater than the lead of the proximal threaded section 1616. In one arrangement, the lead of the distal threaded section 1618 may be approximately twice as large as the lead of the proximal threaded section 1616. As can also be seen in FIG. 31, a dead space 1617 may be provided between the proximal threaded section 1616 and the distal threaded section 1618. In at least one example, the anvil drive shaft 1610 may be fabricated in one piece from extruded gear stock.

To facilitate assembly of the various anvil components, the anvil assembly 1560 includes an anvil cap 1563 that may be attached to the anvil frame 1562 by welding, snap features, etc. In addition, the anvil assembly 1560 includes a pair of anvil plates or staple forming plates 1568 that may contain various patterns of staple forming pockets or forming pockets on the bottom surfaces thereof that correspond to the staple arrangements in the surgical staple cartridge 1550 that is supported in the elongate channel 1520. The staple forming plates 1568 may be made of a metal or similar material and be welded to or otherwise attached to the anvil frame 1562. In other arrangements, a single anvil plate that has a slot therein to accommodate a firing member may also be employed. Such anvil plate or combination of plates may serve to improve the overall stiffness of the anvil assembly. The anvil plate(s) may be flat and have the staple forming pockets or forming pockets "coined" therein, for example.

Figure 29:
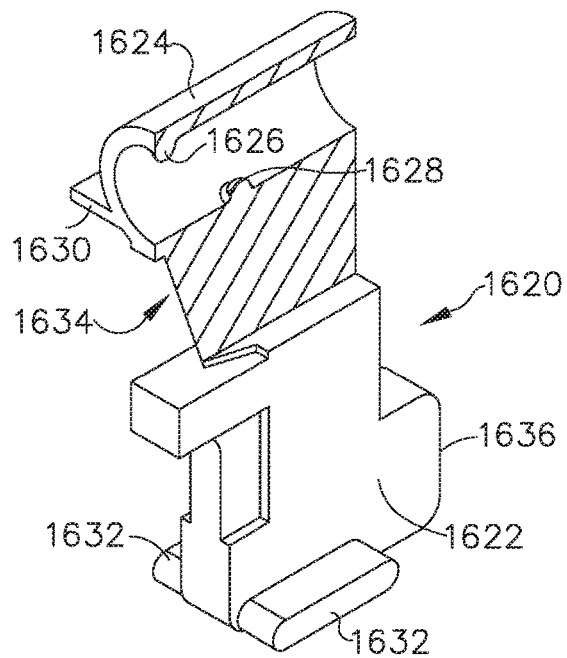
FIG. 29 is a cross-sectional perspective view of a firing member or cutting member in accordance with at least one embodiment.

FIG. 29 illustrates one form of a firing member 1620 that includes a body portion 1622 that has a knife nut portion 1624 formed thereon or otherwise attached thereto. The knife nut portion 1624 is configured to be received on the anvil drive shaft 1610. A distal thread nodule 1626 and a proximal thread nodule 1628 that are configured to engage the proximal threaded section 1616 and the distal threaded section 1618 are formed in the knife nut portion 1624. The distal thread nodule 1626 is spaced from the proximal thread nodule 1628 relative to the length of the dead space 1617 such that when the knife nut portion 1624 spans across the dead space 1617, the distal thread nodule 1626 is in threaded engagement with the distal threaded section 1618 and the proximal thread nodule 1628 is in threaded engagement with the proximal threaded section 1616. In addition, an anvil engaging tab 1630 protrudes laterally from opposite lateral portions of the knife nut 1624 and is oriented to engage the corresponding staple forming plate 1568 that are attached to the anvil frame 1562. The firing member 1620 further includes a channel engaging tab 1632 that protrudes from each lateral side of the body portion 1622 to engage portions of the elongate channel 1520 as will be discussed in further detail below. The firing member 1620 also includes a tissue cutting surface 1634.

Figure 16:
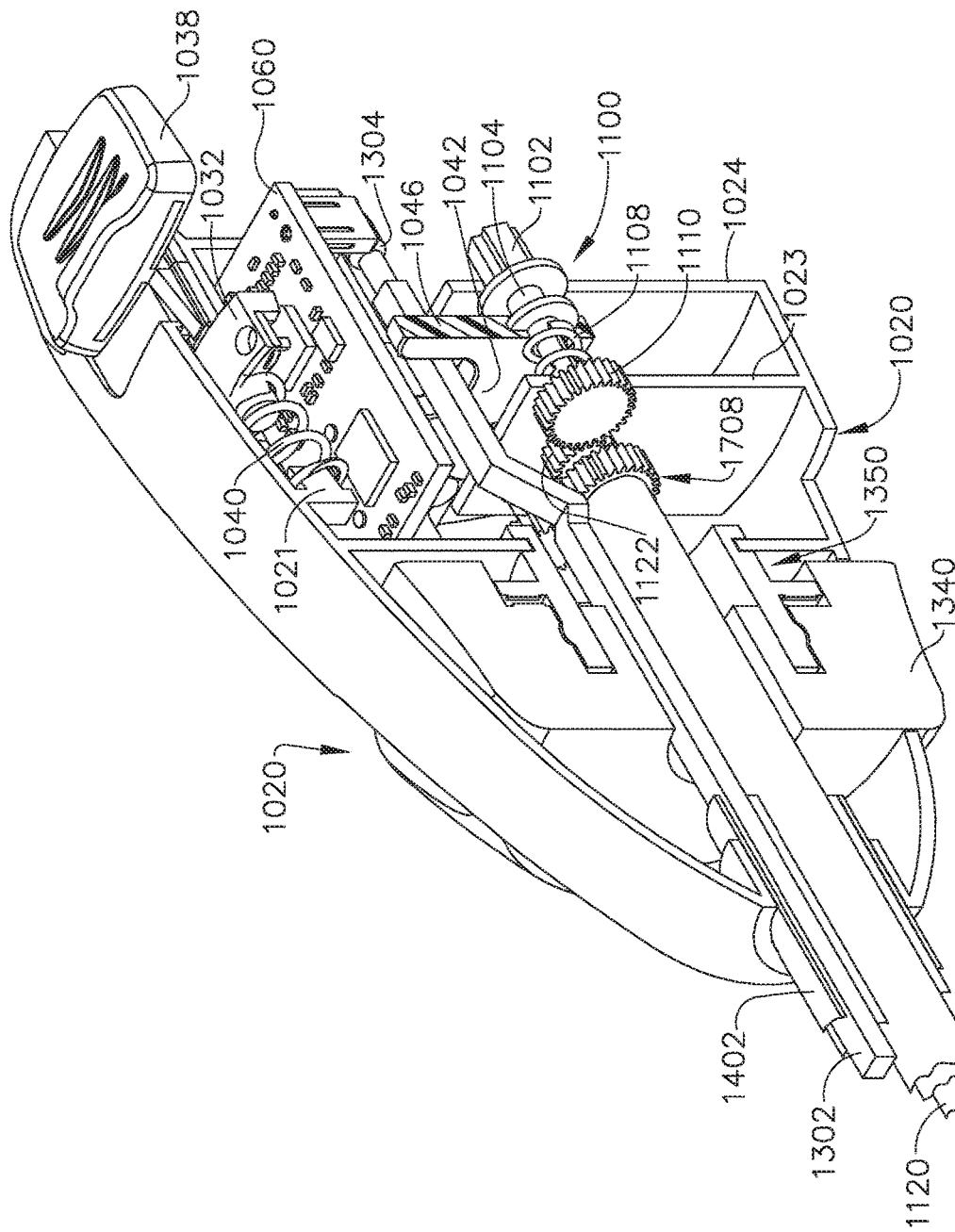
FIG. 16 is a partial cross-sectional perspective view of the tool attachment module portion of FIG. 15.
Figure 17:
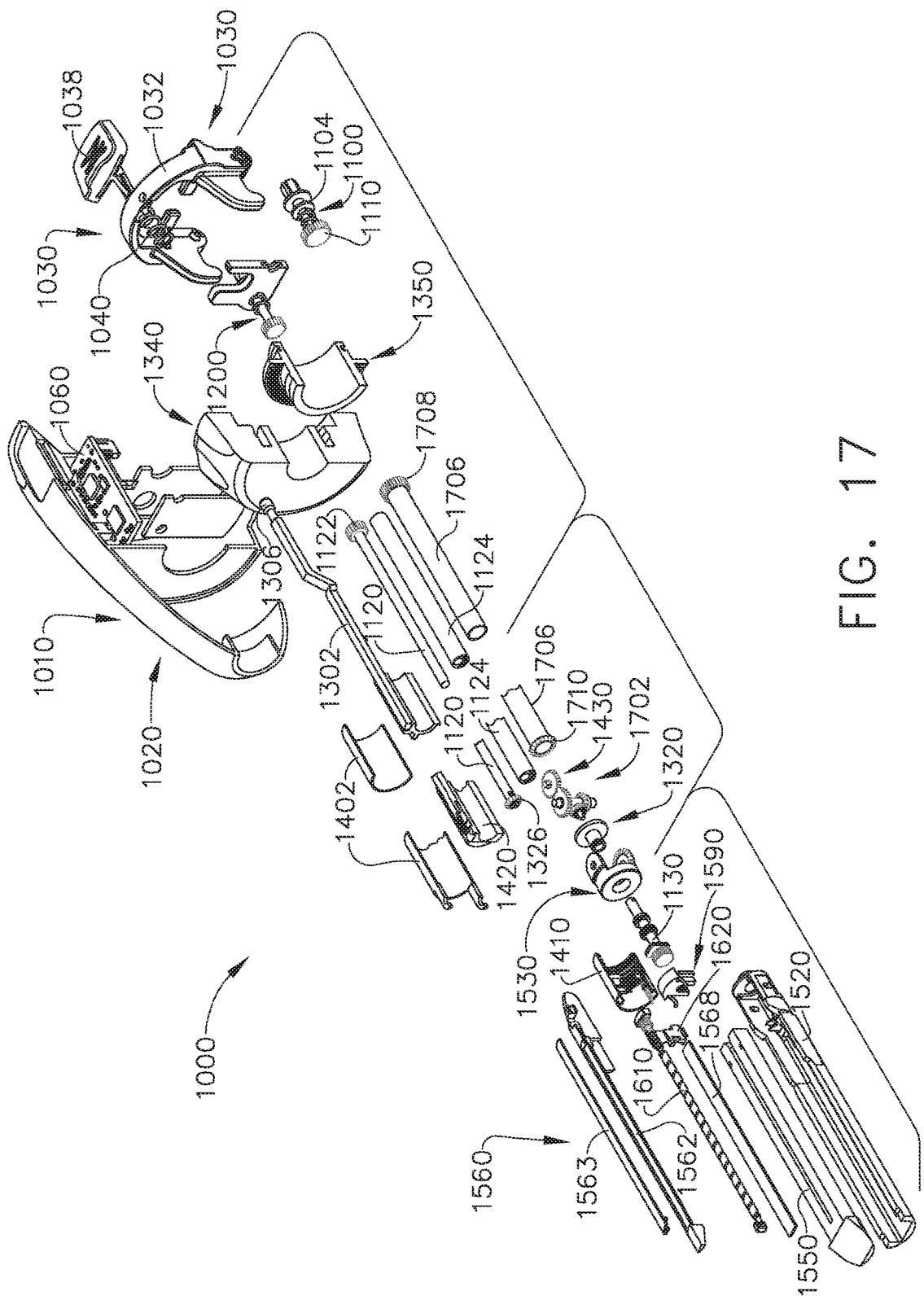
FIG. 17 is an exploded assembly view of portions of the interchangeable surgical tool assembly of FIG. 16.
Figure 30:
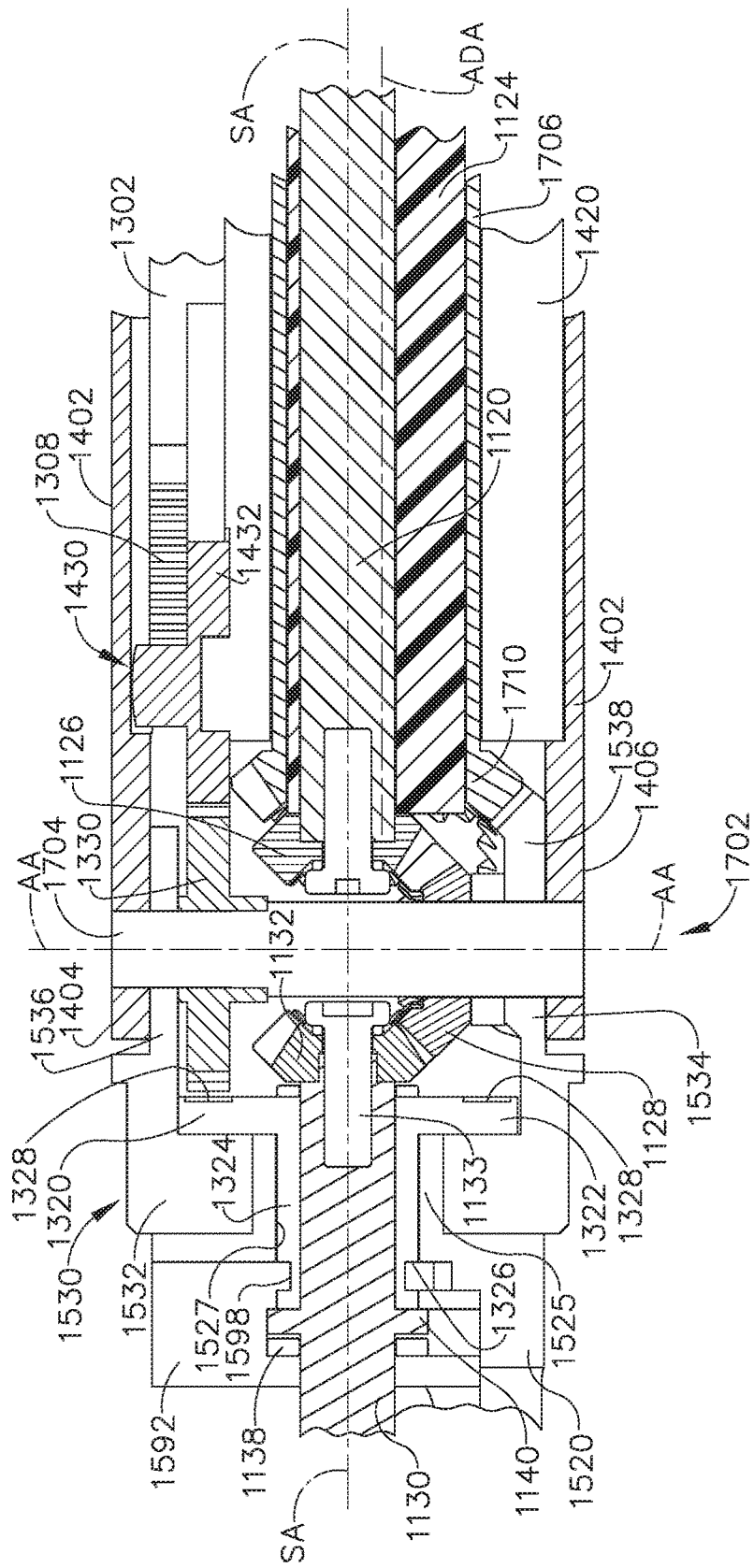
FIG. 30 is a cross-sectional elevational view of an articulation joint in accordance with at least one embodiment.
Figure 32:
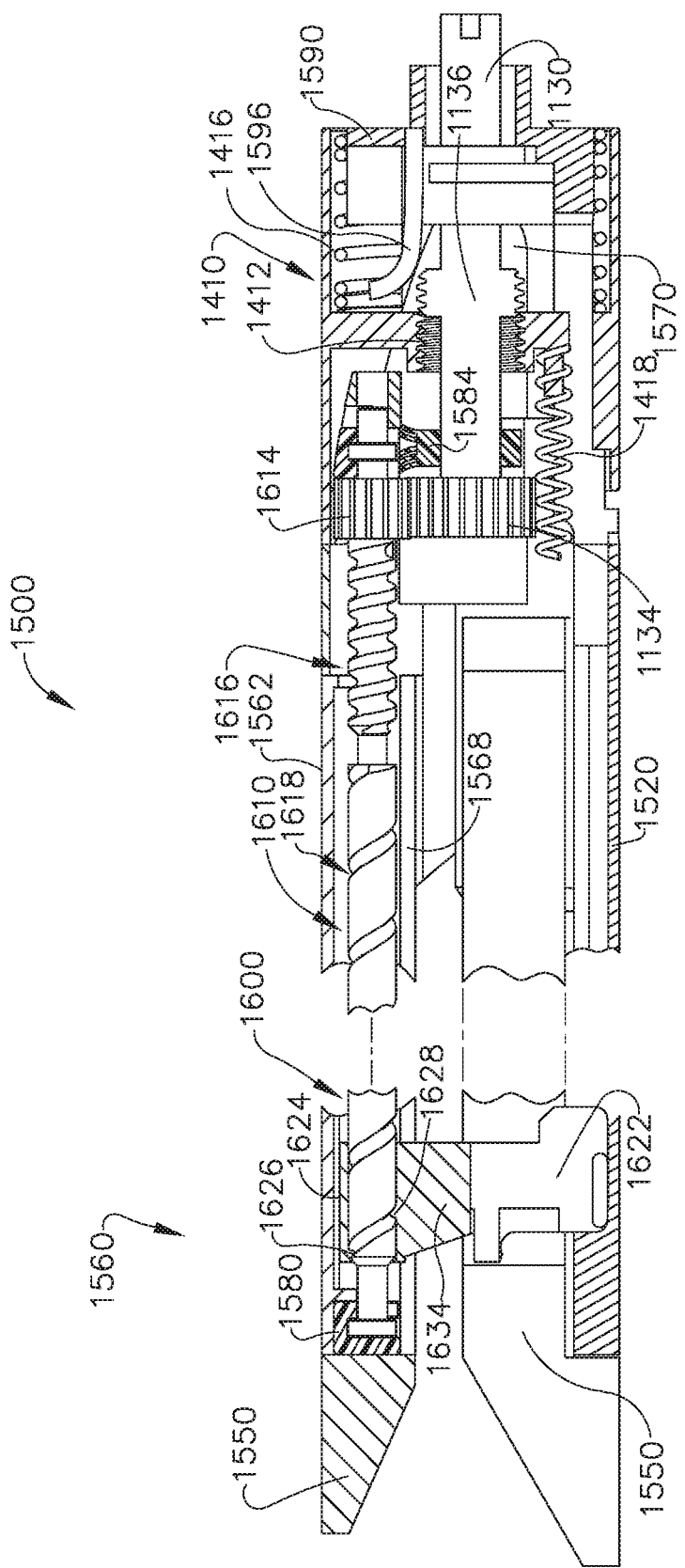
FIG. 32 is another cross-sectional view of the surgical end effector of FIG. 25 with the firing member FIG. 29 in an ending position.

Rotation of the anvil drive shaft 1610 in a first rotary direction will result in the axial movement of the firing member 1620 from a starting position (FIG. 35) to an ending position (FIG. 32). Similarly, rotation of the anvil drive shaft 1610 in a second rotary direction will result in the axial retraction of the firing member 1620 from the ending position back to the starting position. The anvil drive shaft 1610 ultimately obtains rotary motion from a proximal drive shaft 1120 that operably interfaces with the primary transfer shaft 1104. Referring again to FIGS. 16-18, a proximal drive gear 1110 is mounted to the primary transfer shaft 1104 and is supported in meshing engagement with a power driven gear 1122 that is mounted to a proximal end of the proximal drive shaft 1120. The proximal drive shaft 1120 is rotatably supported within a power shaft support tube 1124 and has a power bevel gear 1126 attached to its distal end. See FIG. 30. As indicated above, the illustrated interchangeable surgical tool assembly 1000 includes an articulation joint 1702 that facilitates articulation of the surgical end effector 1500. In at least one embodiment as illustrated in FIG. 30, the articulation joint 1702 comprises an articulation shaft 1704 that is mounted to a distal end of an outer spine tube 1402 of the elongate shaft assembly. In particular, the outer spine tube 1402 includes a pair of distally protruding pivot tabs 1404, 1406 that are attached to the corresponding ends of the articulation shaft 1704 such that the articulation shaft 1704 defines an articulation axis "A-A" that is transverse to a shaft axis "SA-SA" defined by the elongate shaft assembly 1400.

Figure 31:
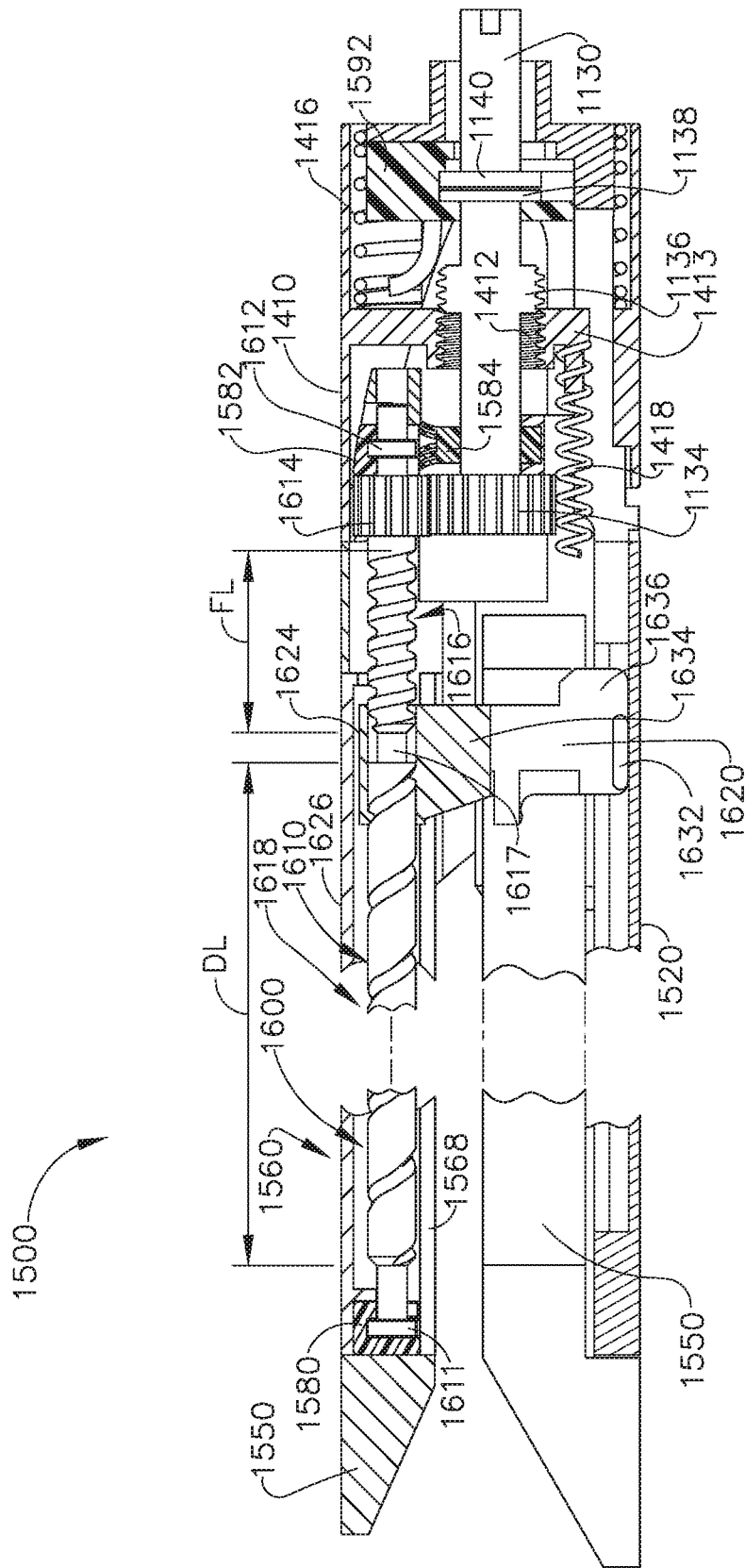
FIG. 31 is a cross-sectional view of the surgical end effector of FIG. 25 with the firing member of FIG. 29 in a firing position.

Still referring to FIG. 30, the power bevel gear 1126 is in meshing engagement with a centrally disposed power transfer gear 1128 that is rotatably journaled on the articulation shaft 1704. The primary rotary drive system 1100 of the illustrated embodiment further includes a distal power shaft 1130 that has a distal driven gear 1132 attached to the proximal end thereof by a screw or other fastener 1133. The distal power shaft 1130 may also be referred to herein as a rotary output drive shaft. The distal driven gear 1132 is in meshing engagement with the centrally disposed power transfer gear 1128. Turning next to FIGS. 31 and 32, a distal drive gear 1134 is attached to the distal end of the distal power shaft 1130. The distal drive gear 1134 is configured for meshing engagement with the driven firing gear 1614 on the anvil drive shaft 1610 when the anvil assembly 1560 is in the closed position as shown in FIGS. 31 and 32. The anvil drive shaft 1610 is said to be "separate and distinct" from the distal power shaft 1130. That is, at least in the illustrated arrangement for example, the anvil drive shaft 1610 is not coaxially aligned with the distal power shaft 1130 and does not form a part of the distal power shaft 1130. In addition, the anvil drive shaft 1610 is movable relative to the distal power shaft 1130, for example, when the anvil assembly 1560 is moved between open and closed positions. FIG. 31 illustrates the anvil assembly 1560 in a closed position and the firing member 1620 in a pre-firing position. As can be seen in that Figure, the distal thread nodule 1626 in the knife nut 1624 of the firing member 1620 is engaged with the distal threaded portion 1618 such that rotation of the anvil drive shaft 1610 drives (fires) the firing member 1620 to the end position illustrated in FIG. 32. Further details regarding the operation of the firing member 1620 are provided below.

Opening and Closing Systems

Figure 36:
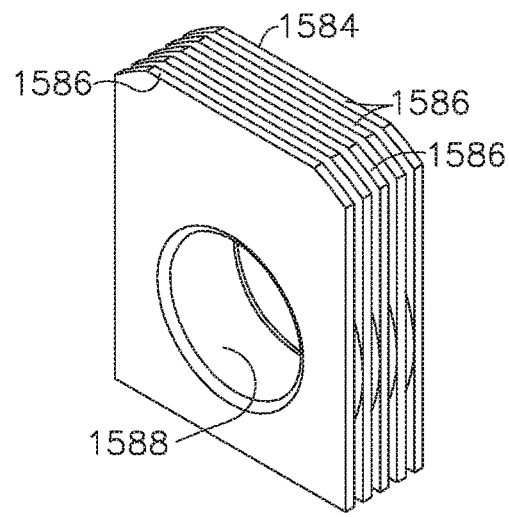
FIG. 36 is a perspective view of a bearing spring in accordance with at least one embodiment.
Figure 33:
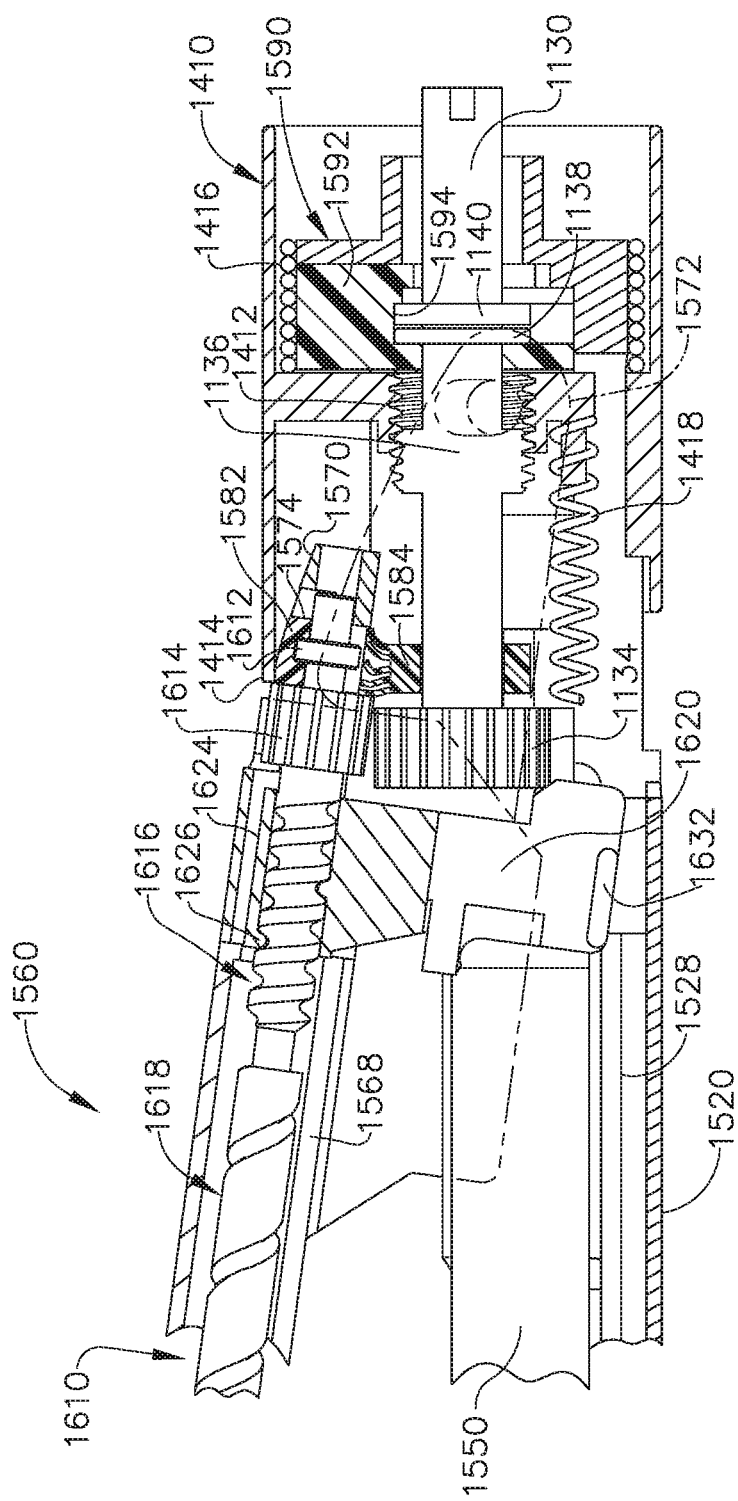
FIG. 33 is another cross-sectional view of a portion of the surgical end effector of FIG. 25 with an anvil assembly in an open position.

In the illustrated arrangement, the anvil assembly 1560 is closed by distally advancing a closure tube 1410 that is a portion of the elongate shaft assembly 1400. As can be seen in FIGS. 27 and 31-35, the closure tube 1410 includes an internally threaded closure nut 1412 that is configured for threaded engagement with a closure thread segment 1136 that is formed on the distal power shaft 1130. FIG. 33 illustrates the anvil assembly 1560 in an open position. As was discussed above, the proximal bearing lug 1612 is rotatably supported in the anvil assembly 1560 by a floating bearing housing 1582 that is movably supported in a bearing pocket 1574 in the proximal anvil portion 1570. A bearing spring 1584 is journaled on the distal power shaft 1130 and is configured to apply a biasing force to the bearing housing 1582 during opening and closing of the anvil assembly 1560. Such biasing force serves to urge the anvil assembly 1560 into the open position. In at least one arrangement, the bearing spring 1584 comprises an assembly of plates 1586 fabricated from, for example, 17-4, 416 or 304 stainless steel that are laminated together by a more annealed stainless steel material and which have a hole 1588 for receiving the distal power shaft 1130 therethrough. See FIG. 36.

Figure 27:
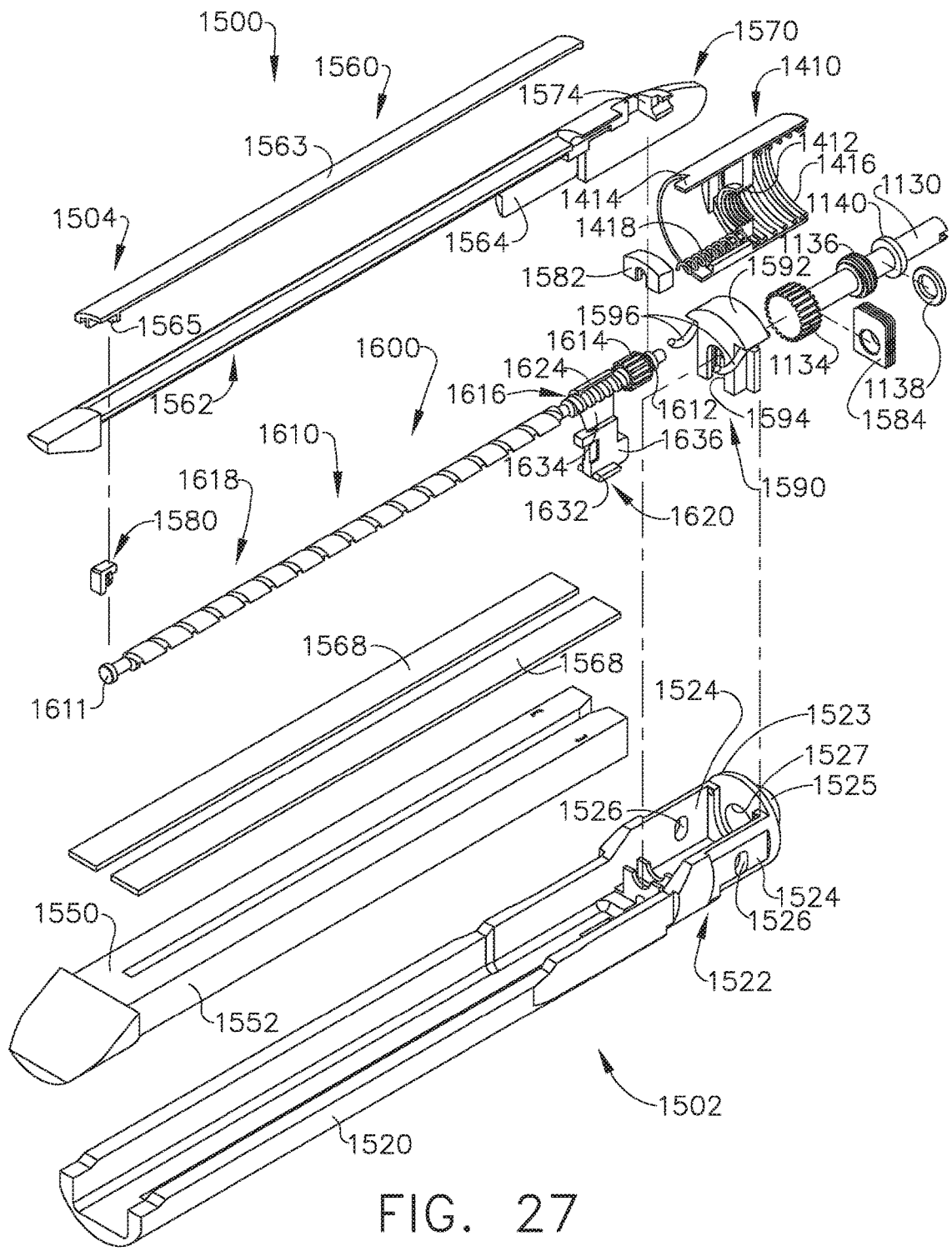
FIG. 27 is an exploded assembly view of the surgical end effector of FIG. 25.
Figure 28:
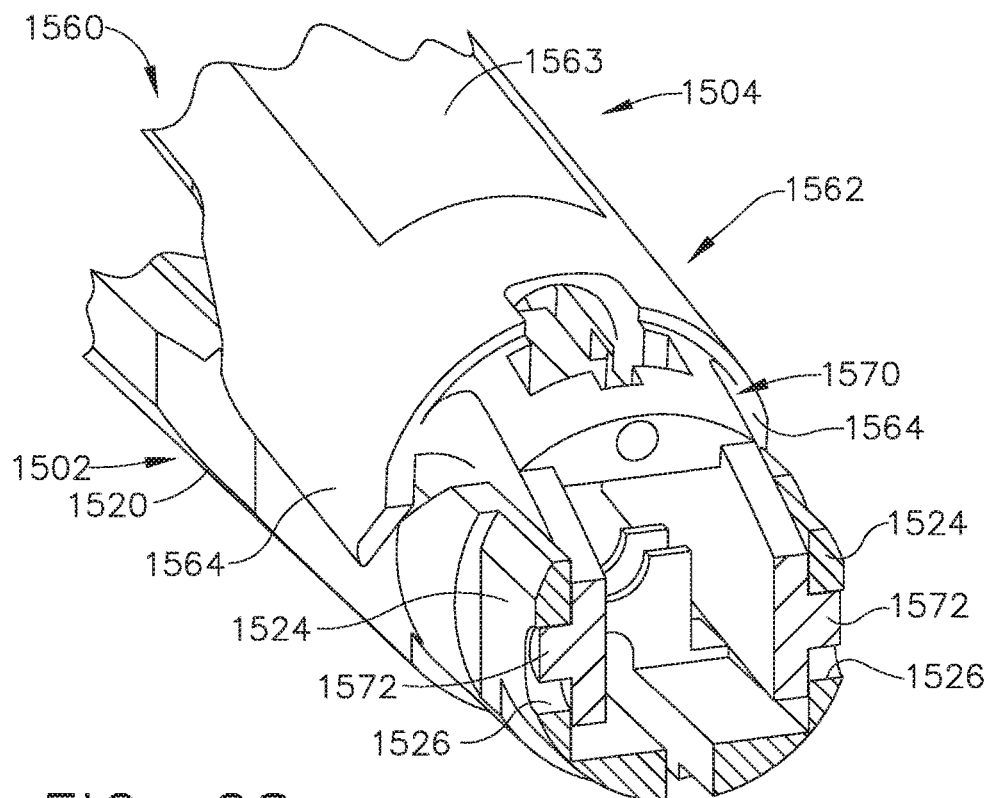
FIG. 28 is a partial rear cross-sectional view of the surgical end effector of FIG. 25.

As indicated above, the anvil trunnion pins 1572 are received in vertically oriented pivot slots 1526 that are formed in the upstanding walls 1524 of the elongate channel 1520 to afford the anvil assembly 1560 with the ability to move vertically relative to the elongate channel 1520 as well as relative to the surgical staple cartridge 1550 supported therein. Such movement of the anvil assembly 1560 relative to the elongate channel 1520 may serve to accommodate different thicknesses of tissue that is clamped therebetween. To that end, in the illustrated example, the surgical end effector 1500 also includes an anvil spring assembly 1590 for managing the magnitude of the tissue gap between the staple forming plates 1568 and the upper surface of the surgical staple cartridge 1550. As can be most particularly seen in FIG. 27, the anvil spring assembly 1590 in the illustrated example includes a bearing mount 1592 that is mounted between the upstanding walls 1524 of the elongate channel 1520. As can be seen in FIGS. 27 and 33, the bearing mount 1592 has a somewhat U-shaped bearing cavity 1594 therein that is configured to operably receive therein a shaft bearing 1138 as well as a bearing stop flange 1140 that is formed on or otherwise attached to the distal power shaft 1130. Such arrangement serves to rotatably support the distal power shaft 1130 within the proximal end portion or channel mounting portion 1522 of the elongate channel 1520. Two spring tabs 1596 extend from the bearing mount 1592 and are oriented to apply a downward biasing force to the proximal anvil portion 1570. See FIG. 32. Such biasing force serves to bias the proximal anvil portion 1570 downward such that the anvil trunnion pins 1572 are biased downward within their corresponding vertical pivot slots 1526 and enable the anvil assembly 1560 to vertically move to accommodate different thicknesses of tissue. As the anvil assembly 1560 is closed, the target tissue that is captured between the anvil assembly 1560 and the surgical staple cartridge 1550 will result in the compression of the cartridge body 1552 and the staples or fasteners supported therein will be pressed through the tissue into forming contact with the staple forming plates 1568 on the underside of anvil assembly 1560. Depending upon the arrangement of staples of fasteners in the staple cartridge 1550, the staples may be formed in several discreet lines through the staple cartridge body and the clamped tissue. For example, there may be a total of six lines of staples (three lines of staple on each side of a central area through which the firing member 1620 may pass). In at least one arrangement, for example, the staples in one line may be offset or staggered from the staples in adjacent lines.

As can be seen in FIG. 33 when the anvil assembly 1560 is in the open position, the closure thread segment 1136 on the distal power shaft 1130 remains in threaded engagement with the closure nut 1412. When in the open position, the firing member 1620 is located in its proximal-most or starting position on the proximal threaded portion 1616 of the anvil drive shaft 1610. As can be seen in FIG. 33, when in that proximal starting position, the channel engagement tabs 1632 on the firing member are able to clear the channel ledges 1528 formed in the elongate channel 1520 to enable the firing member 1620 to pivot with the anvil assembly 1560 to the open position. When in that position (which may also be referred to as a "fully open position"), the driver firing gear 1614 may remain in contact with the distal drive gear 1134, but it is not in meshing engagement therewith. Thus, rotation of the distal power shaft 1130 will not result in rotation of the anvil drive shaft 1610.

To commence the closing process, the distal power shaft 1130 is rotated in a first rotary direction. This initial rotation of the distal power shaft 1130 causes the closure tube 1410 to move in the distal direction DD by virtue of the threaded engagement between the closure thread segment 1136 on the distal power shaft 1130 and the internally threaded closure nut 1412. As the closure tube 1410 moves distally, a closure tab 1414 that is formed on the distal end of the closure tube 1410 contacts the proximal anvil portion 1570 and moves into camming contact therewith to cause the anvil assembly 1560 to pivot to an initial closed position. Further rotation of the distal power shaft 1130 will result in the distal movement of the closure tube 1410 until the closure tube reaches a "fully closed" position wherein the internally threaded closure nut 1412 has threadably disengaged from the closure thread segment 1136. When in that position, for example, the internally threaded closure nut 1412 is distal to the closure thread segment 1136 and further rotation of the distal power shaft 1130 in the first rotary direction will not affect movement of the closure tube 1410. A closure spring 1416 serves to bias the closure tube 1410 distally to retain the internally threaded closure nut 1412 out of threaded engagement with the closure thread segment 1136.

Figure 34:
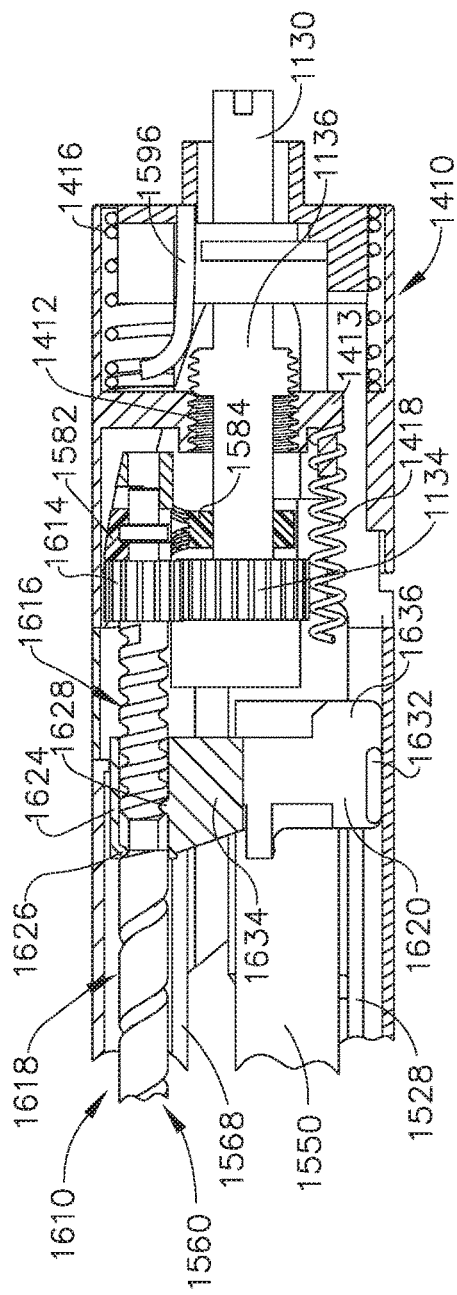
FIG. 34 is another cross-sectional view of a portion of the surgical end effector of FIG. 25 with the firing member of FIG. 29 in a pre-firing position.

Once the anvil assembly 1560 has been moved to the closed position, the driven firing gear 1614 on the anvil drive shaft 1610 will now be in meshing engagement with the distal drive gear 1134 on the distal power shaft 1130. Further rotation of the distal power shaft 1130 in the first rotary direction will thereby result in the rotation of the anvil drive shaft 1610 and cause the firing member 1620 to move distally on the proximal threaded portion 1616. Continued rotation of the anvil drive shaft 1610 in the first rotary direction will result in the distal movement of the firing member 1620. FIG. 34 illustrates the position of the firing member 1620 just prior to engagement between the distal thread nodule 1626 and the distal threaded portion 1618 of the firing drive shaft. FIG. 31 illustrates the position of the firing member 1620 after the distal thread nodule 1626 has initially threadably engaged the distal threaded portion 1618 of the anvil drive shaft 1610. When in that position, the anvil engaging tabs 1630 on the firing member 1620 have engaged the corresponding staple forming plates 1568 that are attached to the anvil frame 1562 and the channel engaging tabs 1632 have engaged the corresponding ledges 1528 on the elongate channel 1520 to maintain a desired spacing between the anvil assembly 1560 and the elongate channel 1520.

Continued rotation of the distal power shaft 1130 in the first rotary direction causes the anvil drive shaft 1610 to also rotate. Now that the distal thread nodule 1626 has engaged the distal threaded portion 1618 of the anvil drive shaft 1610, the firing member 1620 will move at a "firing speed" that is faster than a "pre-firing speed" that the firing member 1620 moves when threadably engaged with the proximal threaded portion 1616 of the anvil drive shaft 1610. This speed difference is due to the differences in the thread leads of the proximal and distal threaded portions 1616, 1618. As the firing member 1620 moves distally through the end effector 1500, the tissue cutting surface 1634 passes between the staple forming plates 1568 and cuts through the tissue that has been clamped between the anvil assembly 1560 and the surgical staple cartridge 1550. Thus, the tissue is first stapled when the anvil assembly 1560 is moved to the fully closed position. The tissue is thereafter cut when the firing member is distally advanced through the end effector 1500. Thus, the staple forming process may "separate and distinct" from the tissue cutting process.

Figure 35:
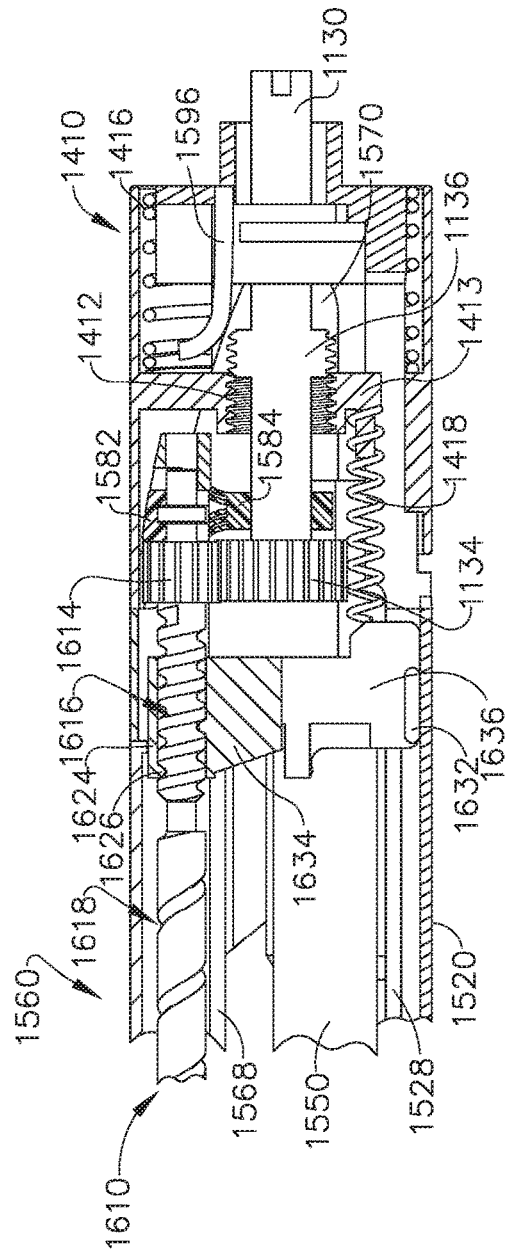
FIG. 35 is another cross-sectional view of a portion of the surgical end effector of FIG. 34 wherein the firing member has been returned to a starting position to thereby urge the internally threaded closure nut into threaded engagement with the closure thread segment on the distal power shaft.

FIG. 32 illustrates the position of the firing member 1620 at the end firing position or near the end firing position. Once the firing member 1620 has reached the end firing position which may, for example, be determined by sensors, encoders, etc.—not shown, the distal power shaft 1130 may be rotated in a second rotary direction or "retraction direction" which also causes the anvil drive shaft 1610 to rotate in the opposite direction. Rotation of the anvil drive shaft 1610 in the second rotary direction will cause the firing member 1620 to move proximally to the position shown in FIG. 35. As can be seen in FIG. 35, the closure tube 1410 is fitted with a closure tube reset spring 1418 that extends distally from a lug 1413 on the closure nut 1412. The firing member 1620 is formed with a proximally extending reset tab 1636 that is configured to contact and apply a proximal compression force to the closure tube reset spring 1418 when the firing member 1620 returns to the starting position. Such proximal compression force serves to urge the closure tube 1410 and, more particularly, the internally threaded closure nut 1412 against the closure thread segment 1136 on the distal power shaft 1130 so that the closure nut threads threadably re-engage the closure thread segment 1136 on the distal power shaft 1130. As the distal power shaft 1130 continues to rotate in the second rotary direction, the interaction between the closure thread segment 1136 and the closure nut 1412 causes the closure tube 1410 to move proximally so that the closure tab 1414 moves out of camming contact with the proximal anvil portion 1570 to thereby permit the bearing spring 1584 to urge the anvil assembly 1560 to the open position (FIG. 33). The tissue contained between the anvil assembly 1560 and the elongate channel 1520 may also serve to urge the anvil assembly 1560 to the open position wherein the tissue may be removed therefrom.

Articulation System

As indicated above, the illustrated example includes an articulation system 1700 that facilitates articulation of the surgical end effector 1500 about the articulation axis AA that is transverse to the shaft axis SA. In the illustrated example, the surgical end effector 1500 is also capable of being selectively rotated about the shaft axis SA distal to the articulation joint 1702 as represented by arrow 1703 in FIG. 24. In the illustrated example, the articulation system 1700 is actuated by the second rotary drive system 320 in the handle assembly 20. As was discussed above, the interchangeable surgical tool assembly 1000 includes a secondary rotary drive system 1220 that is configured to operably interface with a second rotary drive system 320 on the handle assembly. In the illustrated arrangement, the secondary rotary drive 1220 comprises a portion of the articulation system 1700. In the illustrated example, the articulation system 1700 comprises an articulation drive shaft 1706 that is rotatably supported on the power shaft support tube 1124. As indicated above, the proximal drive shaft 1120 rotatably extends through the power shaft support tube 1124. In the illustrated arrangement, the proximal drive shaft 1120 is coaxially aligned on the shaft axis SA. The power shaft support tube 1124 is configured such that the articulation drive shaft 1706 is not coaxially aligned on the shaft axis SA. Stated another way, the articulation drive shaft 1706 has an articulation drive shaft axis "ADA" that is offset from the shaft axis SA when the articulation drive shaft 1706 is mounted on the power shaft support tube 1124. See FIG. 30. Such arrangement facilitates the formation of a relatively compact nested gear arrangement in the vicinity of the articulation joint 1702 as can be seen in FIG. 38-42. In the illustrated arrangement for example, a proximal articulation driven gear 1708 is mounted to the proximal end of the articulation drive shaft 1706. See FIG. 19. The proximal articulation driven gear 1708 is arranged in meshing engagement with a secondary drive gear 1206 that is mounted to a distal end of the secondary transfer shaft 1204. Rotation of the secondary transfer shaft 1204 and the secondary drive gear 1206 will result in the rotation of the proximal articulation driven gear 1708 as well as of the articulation drive shaft 1706. A distal articulation drive gear 1710 is attached to the distal end of the articulation drive shaft 1706. The distal articulation drive gear 1710 is supported in meshing engagement with a channel articulation gear 1538 that is formed on a channel mounting fixture 1530.

Figure 37:
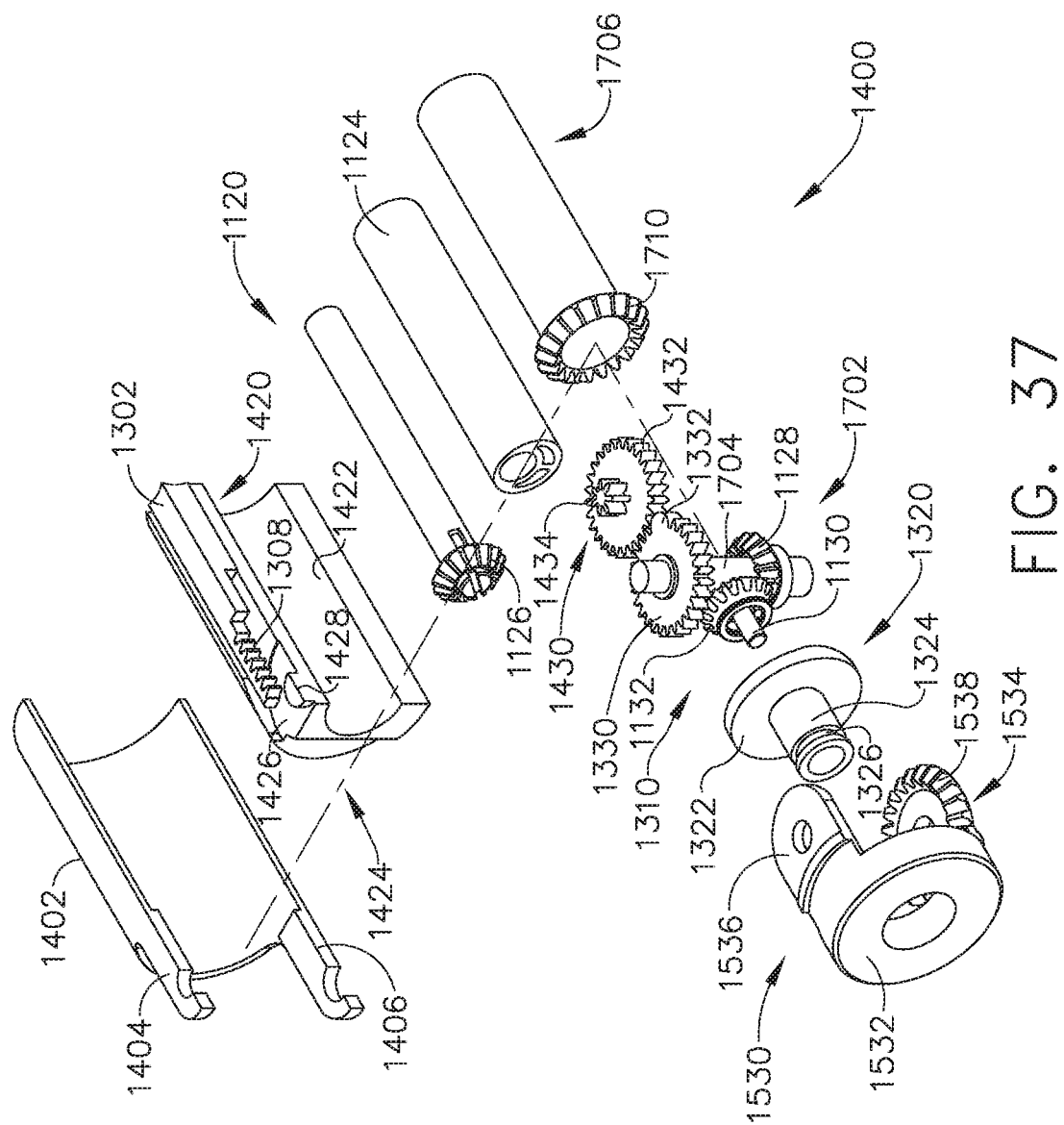
FIG. 37 is an exploded assembly view of the articulation joint of FIG. 30.

More specifically and with reference to FIGS. 30 and 37, in the illustrated example, the channel mounting fixture 1530 comprises a disc-like body portion 1532 that has a lower shaft attachment tab 1534 and an upper shaft attachment tab 1536 formed thereon. The articulation shaft 1704 extends through corresponding holes in the lower and upper shaft attachment tabs 1536, 1534 to be attached to the pivot tabs 1404, 1406 in the outer spine tube 1402. Such arrangement serves to permit the channel mounting fixture 1530 to rotate about the articulation axis AA relative to the outer shaft spine tube 1402. The channel articulation gear 1538 is formed on the lower shaft attachment tab 1534 and is retained in meshing engagement with distal articulation drive gear 1710. Referring now to FIG. 27, in the illustrated example, the channel mounting portion 1522 of the elongate channel 1520 includes an upstanding proximal wall 1523 that has a mounting hub 1525 proximally protruding therefrom. A shaft hole 1527 extends through the mounting hub 1525 and upstanding proximal wall 1523 that is configured to permit the distal power shaft 1130 to extend therethrough. In the illustrated example, the channel mounting fixture 1530 is frictionally mounted on the mounting hub 1525 to complete the coupling of the end effector 1500 to the articulation joint 1702. See FIG. 30.

Figure 38:
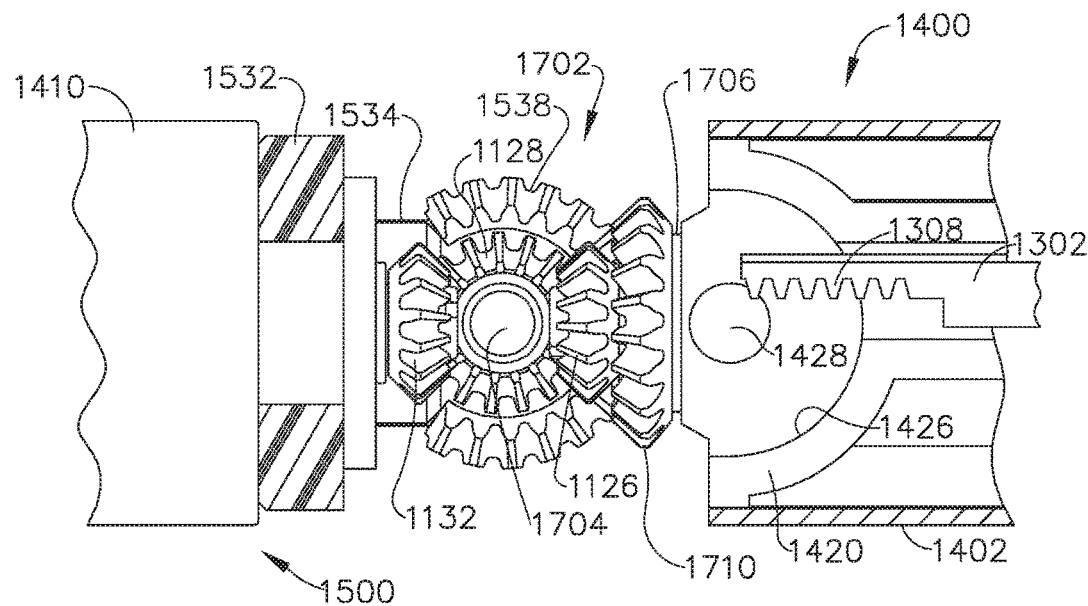
FIG. 38 is a top view of the articulation joint of FIG. 30 with the surgical end effector of FIG. 25 in an unarticulated orientation.
Figure 39:
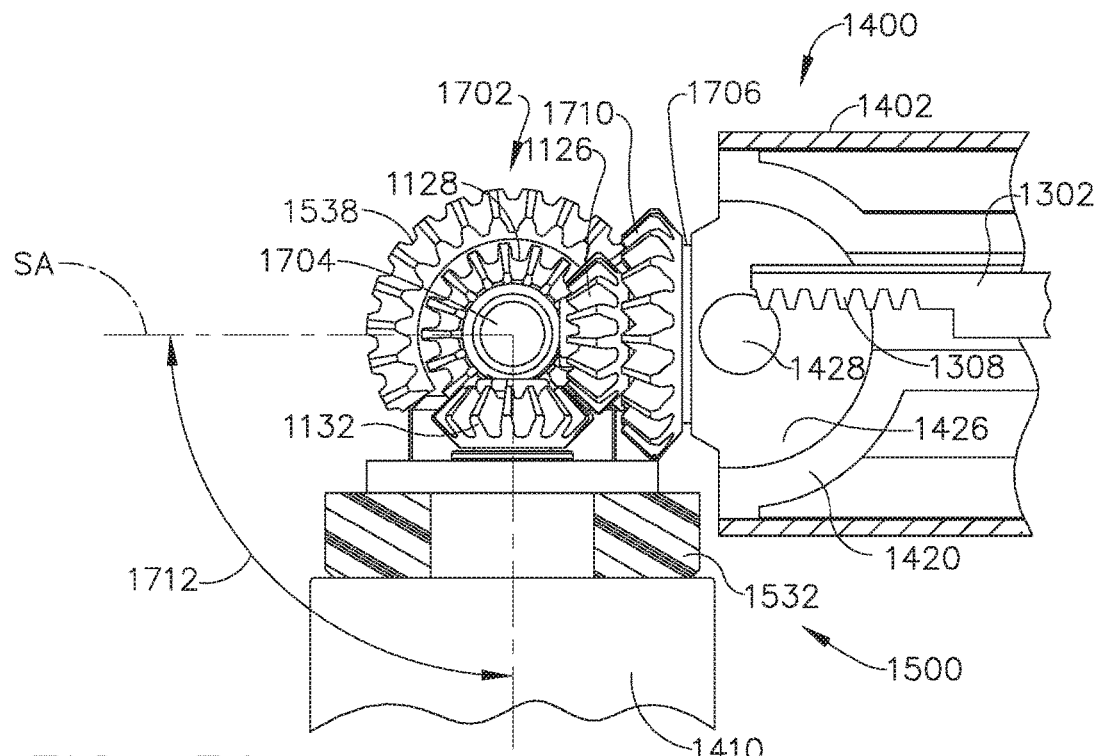
FIG. 39 is another top view of the articulation joint of FIG. 30 with the surgical end effector in a maximum articulated orientation.
Figure 40:
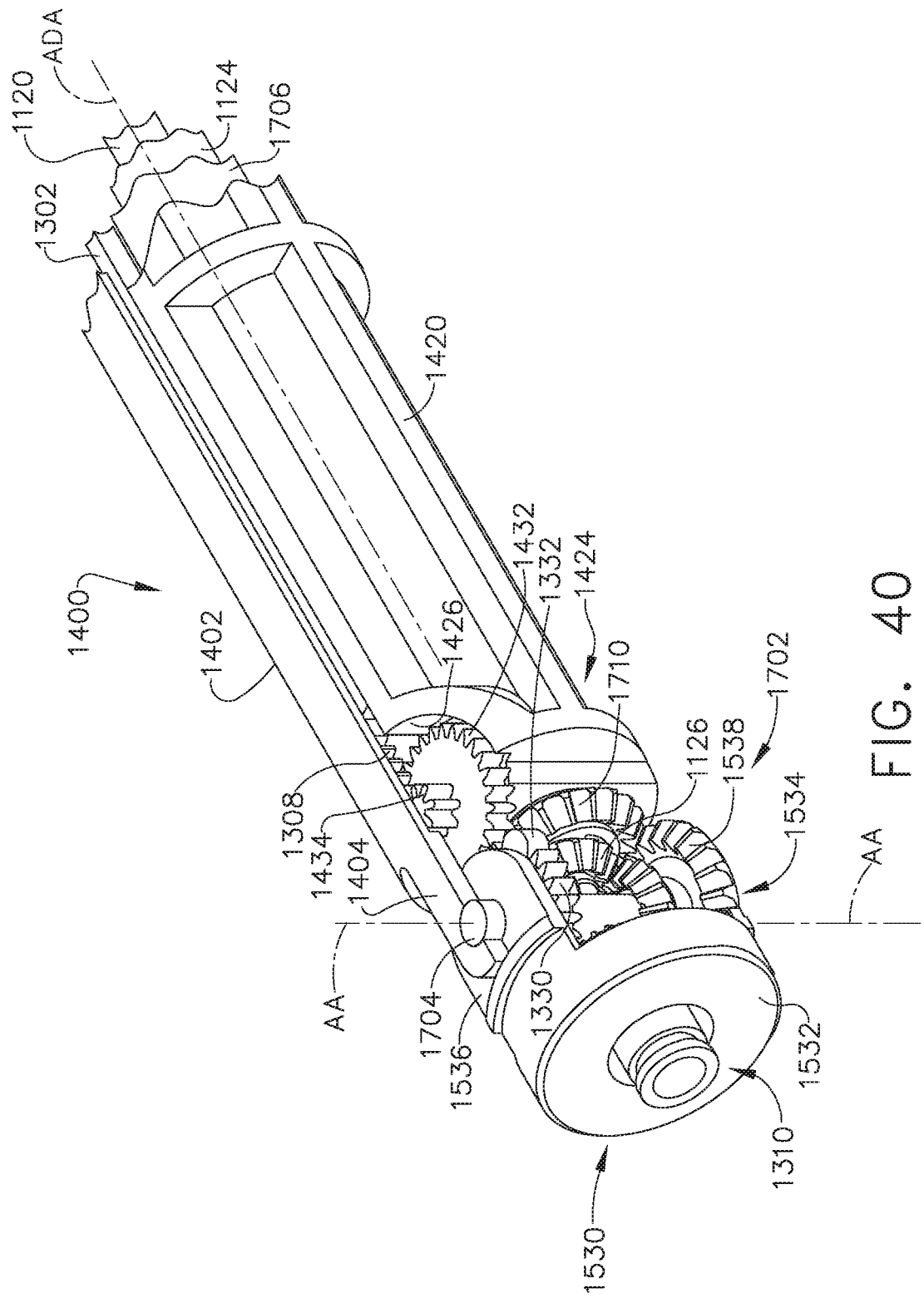
FIG. 40 is a perspective view of a portion of the elongate shaft assembly of FIG. 23 showing the articulation joint of FIG. 30 and portions of a surgical end effector rotary locking system embodiment.
Figure 41:
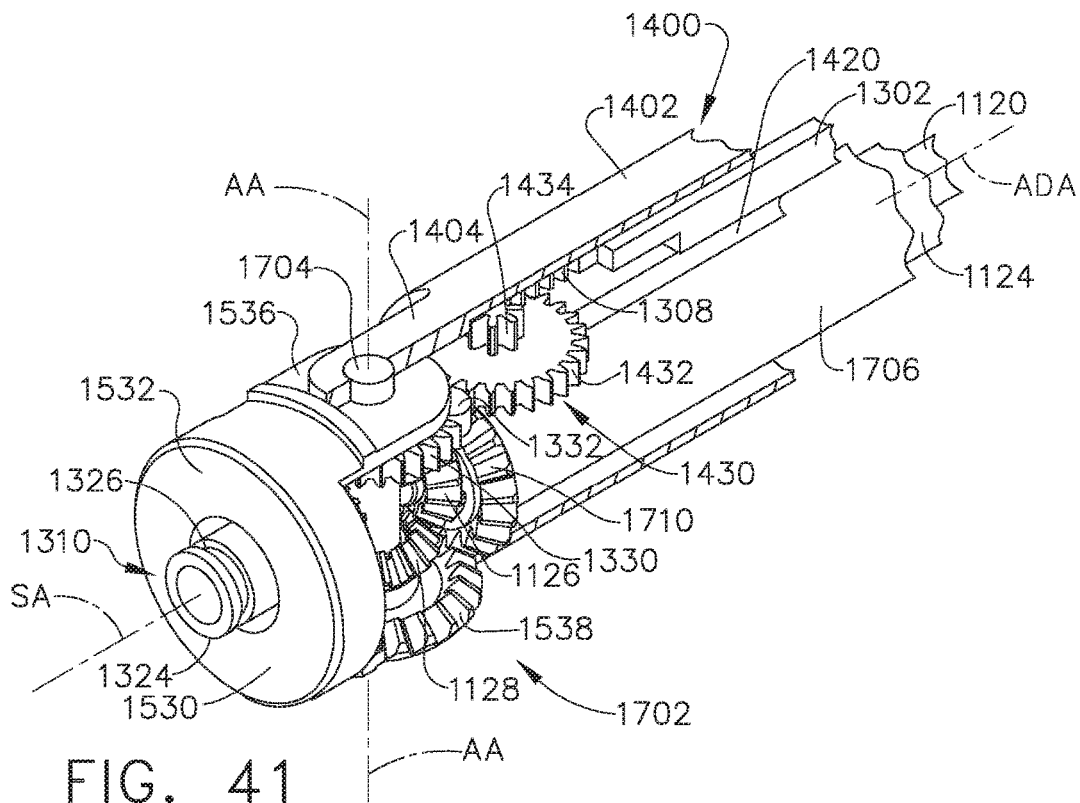
FIG. 41 is a partial cross-sectional perspective view of the surgical end effector rotary locking system of FIG. 40 in an unlocked orientation.

FIGS. 30, 38 and 39 best illustrate operation of the articulation joint 1702. Rotation of the articulation drive shaft 1704 in a first rotary direction by the second rotary drive system 320 will result in rotation or articulation of the surgical end effector 1500 in an articulation angle 1711 (FIG. 39) relative to the shaft axis SA. In at least one example, the articulation angle 1711 may be between 0°-90°, for example. Rotation of the articulation drive shaft 1704 in an opposite rotary direction will result in the articulation of the surgical end effector 1500 in an opposite articulation direction. Once the surgical end effector 1500 has been articulated to the desired orientation, power to the second rotary drive system 320 (and ultimately to the secondary rotary drive system 1200) is discontinued. The friction between the components (i.e., gears) of the secondary rotary drive system 1200, as well as the components (i.e., gears) of the articulation system 1700, serves to retain the surgical end effector 1500 in the articulated orientation. In alternative arrangements, however, gears 306 and 326 may be locked in place. For example, when gear 252 engages these gears, the shifting mechanism that engages gear 252 with gear 306 can disengage the lock. This can be accomplished with a simple cam surface that disengages the locking means when the gear 252 moves to engage.

End Effector Rotation

Figure 42:
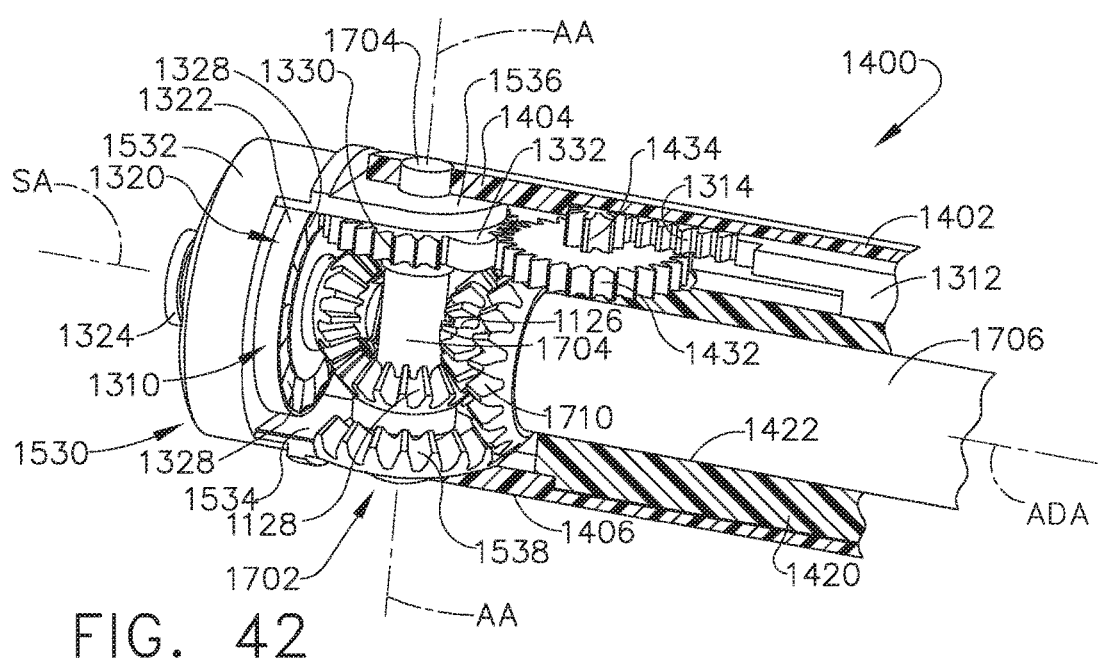
FIG. 42 is another partial cross-sectional perspective view of the surgical end effector rotary locking system of FIGS. 40 and 41 in an unlocked orientation.

The illustrated interchangeable surgical tool assembly 1000 is configured to employ the primary rotary drive system 1100 to selectively rotate the surgical end effector 1500 about the shaft axis SA. In addition, in the illustrated example, the tertiary axial drive system 1300 is configured to selectively lock the surgical end effector 1500 in the desired rotary orientation. As can be seen in FIGS. 37 and 42, for example, the elongate shaft assembly 1400 includes an elongate shaft support tube 1420 that extends from the tool mounting portion 1010 to just proximal of the articulation joint 1702. The elongate shaft support tube 1420 includes an "off-axis" passageway 1422 for rotatably supporting the articulation drive shaft 1706 therethrough. The elongate shaft support tube 1420 further includes a distal end 1424 that has a gear cavity 1426 and a gear axle 1428 formed therein for accommodating a locking gear assembly 1430 therein. See FIG. 37. The locking gear assembly 1430 includes drive gear 1432 that is received within the gear cavity 1426 in the elongate shaft support tube 1420. In addition, the locking gear assembly 1430 has a smaller driven gear 1434 attached thereto. As was briefly discussed above, the tertiary axial drive system 1300 includes a tertiary actuation shaft 1302 that is also referred to herein as a locking control rod 1302. The locking control rod 1302 has a shaft attachment lug 1306 formed on the proximal end 1304 thereof. When the interchangeable surgical tool assembly 1000 is coupled to the handle assembly 20, the shaft attachment lug 1306 is received in the shaft attachment socket 414 on the distal end 412 of the third drive actuator member 410. Thus, actuation of the third axial drive 400 will result in the axial movement of the locking control rod 1302. In the illustrated arrangement, the axially movable locking control rod 1302 has a gear rack 1308 formed in its distal end that is configured for meshing engagement with the driven gear 1434. Axial movement of the locking control rod 1302 will result in rotation of the locking gear assembly 1430 in a first rotary direction about the gear axle 1428 and axial movement of the locking control rod 1302 in the proximal direction will result in rotation of the locking gear assembly 1430 in a second rotary direction.

Figure 43:
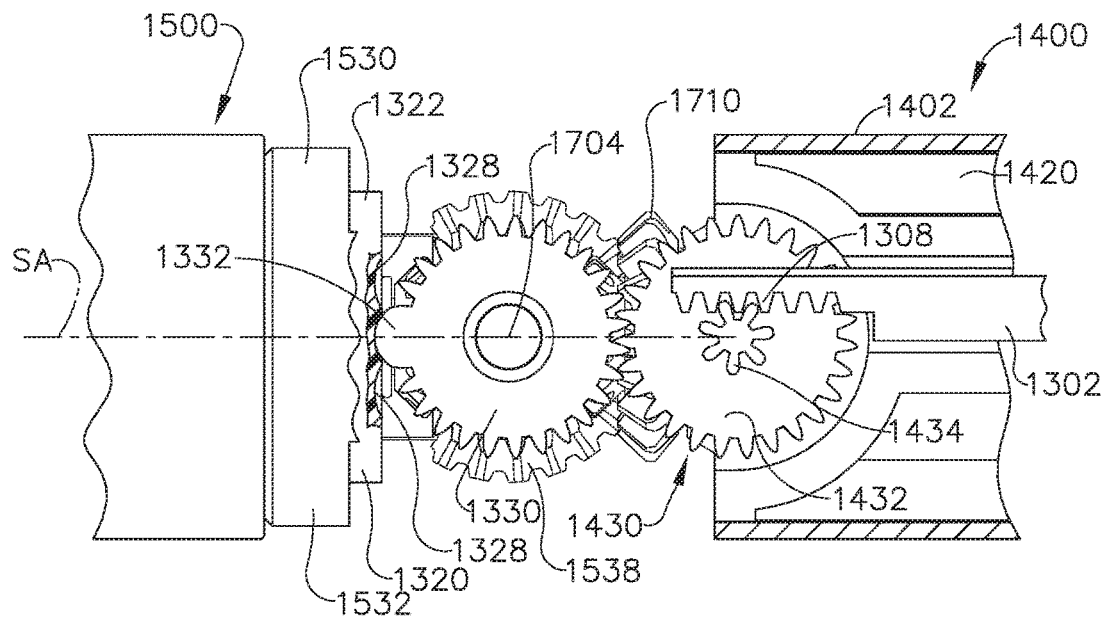
FIG. 43 is a top view of the surgical end effector rotary locking system of FIGS. 40-42 in a locked orientation.
Figure 44:
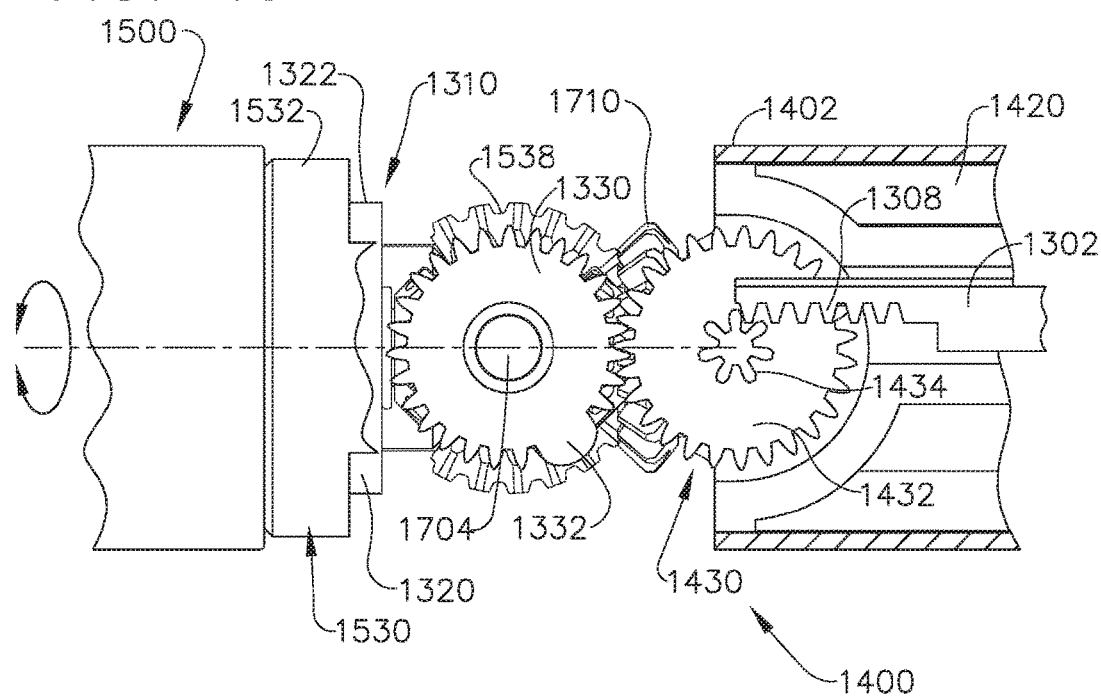
FIG. 44 is a top view of the surgical end effector rotary locking system of FIGS. 40-43 in an unlocked orientation.

In the illustrated example, the tertiary drive system 1300 is configured to operably interface with an end effector rotary locking system 1310. In at least one embodiment, the end effector rotary locking system 1310 comprises a rotation locking disc 1320 that includes a disc-like body 1322 that has a hollow mounting stem 1324 protruding therefrom. As can be seen in FIG. 30, the mounting stem 1324 extends through the shaft hole 1527 in the mounting hub 1525. The distal end of the mounting stem 1324 includes an annular groove 1326 that is configured to receive an inwardly extending fastener flange 1598 that is formed on the bearing housing 1592 of the anvil spring assembly 1590. The proximal-facing surface of the disc-like body 1322 of the rotation locking disc 1320 has a plurality of lock detents 1328 radially arranged thereon. The lock detents 1328 are arranged to be frictionally engaged by a lock member that, in at least one form comprises a lock lug 1332 that is formed on a lock gear 1330 that is journaled on the articulation shaft 1704. See FIGS. 43 and 44. As can be seen in those Figures, the lock gear 1330 is supported in meshing engagement with drive gear 1432 of the locking gear assembly 1430. Actuation of the tertiary actuation shaft 1302 by the tertiary drive system 1300 will result in rotation of the locking gear assembly 1430. Actuation of the locking gear assembly 1430 will result in the rotation of the lock gear 1330 about the articulation shaft 1704. When the lock lug 1332 on the lock gear 1330 is in engagement with a lock detent 1328, the rotation locking disc 1320, as well as the end effector 1500, is prevented from rotating about the shaft axis SA. For example, the lock lug 1332 frictionally engages the corresponding lock detent 1328 and serves to urge the rotation locking disc 1320 into further frictional engagement with the body portion 1532 of the channel mounting fixture 1530. Such frictional engagement between those two components serves to prevent the locking disc 1320 as well as the elongate channel 1520 from rotating about the shaft axis SA. FIG. 43 illustrates the lock lug 1332 in locking engagement with one of the lock detents 1328 and FIG. 44 illustrates the lock lug 1332 in an unlocked orientation whereby the locking disc 1320 is free to rotate about the shaft axis SA.

In the illustrated embodiment of the interchangeable surgical tool assembly 1000, rotation of the end effector 1500 about the shaft axis SA is controlled by a remote rotation dial 1340 that is rotatably supported on the nozzle frame 1020. The remote rotation dial 1340 operably interfaces with a rheostat mounting assembly 1350 that is mounted within the nozzle frame 1020. As can be seen in FIG. 23, for example, the remote rotation dial 1340 includes a plurality of scallops 1341 around its perimeter and is accessible on both sides of the nozzle frame 1020. Such arrangement may enable the user to engage and rotate the remote rotation dial 1340 with a finger of the same hand that is gripping the handle assembly 20 or the remote rotation dial may be engaged with the user's other hand as well. Referring to FIGS. 18, 20 and 21, the rheostat mounting assembly 1350 includes a hollow mounting hub 1352 that has an annular groove 1354 for receiving a corresponding mounting bulkhead 1028 that is formed in the nozzle frame 1020. In at least one arrangement, the mounting hub 1352 includes an annular retention detent 1356 that is configured to retain the remote rotation dial 1340 on the hollow mounting hub 1352 while permitting the remote rotation dial 1340 to rotate relative thereto. The rheostat mounting assembly 1350 includes a radially extending flange portion 1358 that supports a collection of stationary contacts 1360 thereon. See FIG. 18. The flange portion 1358 is received within a rheostat cavity 1342 in the remote rotation dial 1340. A rotary contact assembly 1344 is mounted within the rheostat cavity 1342 and is configured to interface with the stationary contacts 1360 as the remote rotation dial 1340 is rotated on the rheostat mounting assembly 1350. The rheostat mounting assembly is wired to or is otherwise in communication with the tool circuit board 1060.

In at least one arrangement, rotation of the surgical end effector 1500 about the shaft axis SA is commenced by rotating the remote rotation dial 1340. In at least one arrangement, the control system or CPU 224 is configured to rotate the surgical end effector 1500 in the same rotary direction as the remote rotation dial 1340 is rotated. Initial rotation of the remote rotation dial 1340 will cause the control system or CPU 224 in the handle assembly 20 to activate the third axial drive system 400 in the handle assembly 20. In particular, the control system or CPU 224 actuates the solenoid 402 which results in the axial movement of the third actuator member 410. Axial movement of the third actuator member 410 results in the axial movement of the tertiary actuation shaft or locking control rod 1302 which is operably coupled thereto. Axial movement of the locking control rod 1302 results in the rotation of the locking gear assembly 1430. Rotation of the locking gear assembly 1430 will cause the lock gear 1330 to rotate to the unlocked position (FIG. 44). The control system or CPU 224 will then activate the first rotary drive system 300. The reader will appreciate that because the lock lug 1332 has rotated out of engagement with the corresponding lock detent 1328 on the rotation locking disc 1320 that the rotation locking disc 1320 is now capable of rotating about the shaft axis SA. However, friction between the rotation locking disc 1320 and the mounting hub 1525 on the channel mounting portion 1522 may temporarily prevent the surgical end effector 1500 from rotating.

Actuation of the first rotary drive system 300 will result in the application of rotary drive motion to the first drive socket 302 because the shifter solenoid 260 has not been actuated and shifter spring 166 has biased the shifter gear 250 into meshing engagement with the first driven gear 306 on the first drive socket 302. See FIGS. 6 and 7. Rotation of the first drive socket 302 will result in rotation of the primary transfer shaft 1104 which is in operable engagement with the first drive socket 302. Rotation of the primary transfer shaft 1104 will result in the rotation of the proximal drive gear 1110 that is attached to the primary transfer shaft 1104. Because the proximal drive gear 1110 is in meshing engagement with the power driven gear 1122 that is attached to the proximal drive shaft 1120, the proximal drive shaft 1120 is also rotated. See FIG. 19.

Referring now to FIG. 30, rotation of the proximal drive shaft 1120 will ultimately result in the rotation of the distal driven gear 1132 that is attached to the distal power shaft 1130. Rotation of the distal driven gear 1132 will result in rotation of the distal power shaft 1130. The friction between the distal power shaft 1130 and the rotation locking disc 1320, as well as the friction between the bearing housing 1592 and the distal power shaft 1130 and the rotation locking disc 1320, as well as the friction between the closure nut 1412 of the closure tube 1410 and the closure thread segment 1136 on the distal power shaft 1130 in total ("second amount of friction") is greater than the friction between the mounting hub portion 1525 of the elongate channel 1520 and the channel mounting fixture 1530, as well as the friction between the rotation locking disc 1320 and the channel mounting fixture 1530 in total ("first amount of friction") so as to permit the elongate channel 1520 and closure tube 1410 to rotate with the distal power shaft 1130 relative to the channel mounting fixture 1530 about the shaft axis SA. In one arrangement, for example, the rotary position of the remote rotation dial 1340 will, through the control system or CPU 224, determine the rotary position of the distal power shaft 1130 and ultimately the surgical end effector 1500. Once the user has positioned the surgical end effector 1500 in the desired rotary position about the shaft axis SA and has discontinued rotation of the remote rotation dial 1340, the control system or CPU 224 will discontinue power to the first rotary drive system 300 as well as to the third axial drive system 400. In at least one embodiment, the solenoid 402 is "spring loaded" such that upon deactivation, the spring component thereof will bias the third drive actuator member 410 distally which will result in the proximal movement of the locking control rod 1302. Such axial movement of the locking control rod 1302 will result in the rotation of the lock gear 1330 to thereby bring the lock lug 1332 into retaining engagement with the corresponding lock detent 1328 on the rotation locking disc 1320 and thereby lock the surgical end effector 1500 into that rotary orientation. Thus, should power be lost to the handle assembly 20 and, more particularly to the third drive system 400, the solenoid spring will cause the end effector rotary locking system 1310 to move to the locked orientation to thereby prevent rotation of the surgical end effector 1500 relative to the elongate shaft assembly 1400. As can be appreciated from the foregoing discussion, when the interchangeable surgical tool assembly 1000 is operably coupled to the handle assembly 20, the third axial drive system 400 is employed to unlock the end effector locking system 1310 and the first rotary drive system 300 is employed to rotate the surgical end effector 1500 relative to the elongate shaft assembly 1400. The reader will appreciate that such rotation of the surgical end effector 1500 is completely distal to the articulation joint 1702. Thus, the outer spine tube 1402, as well as the articulation joint 1702, remain stationary during the rotation process.

One general method of operating and controlling the surgical instrument 10 will now be described. FIG. 1 illustrates the surgical instrument 10 after the interchangeable surgical tool assembly 1000 has been operably attached to the handle assembly 20. As indicated above, coupling the tool attachment module portion 1010 of the interchangeable surgical tool assembly 1000 to the tool attachment portion 500 of the handle assembly 20 causes the tool circuit board 1060 to be coupled to or otherwise communicate with the handle circuit board 220 that comprises the control system or CPU 224. Once connected or in communication with the control system or CPU 224, the tool circuit board 1060 may provide specific software to the control system or CPU 224 that is unique to that particular interchangeable surgical tool assembly. The clinician may also position the grip portion 100 of the handle assembly 20 in the desired position relative to the primary housing portion 30 that may be best suited for the type of interchangeable surgical tool assembly being used.

As can be seen in FIG. 3, the illustrated handle assembly 20 includes right and left control button assemblies 270R, 270L that interface with the control system or CPU 224. In one exemplary arrangement, each control button assembly 270R, 270L includes a first button 272, a second button 274 and a third button 276 that each interface with the control system or CPU 224. It will be understood that in at least one embodiment, the control button 272 on the right control button assembly 270R may perform the same control function as the control button 272 on the left control button assembly 270L. Similarly, the control button 274 on the right control button assembly 270R may perform the same control function as the control button 274 on the left control button assembly 270L. Likewise, the control button 276 on the right control button assembly 270R may perform the same control function as the control button 276 on the left control button assembly 270L. Such arrangements enable the clinician to control the surgical instrument from both sides of the handle assembly 20. In at least one arrangement, the control buttons 272, 274, 276 comprise "Hall Effect" sensors or linear sensors so actuation of the buttons can indicate the intensity of the user's request as well as the speed desired, for example.

In one arrangement, the first and second control buttons 272, 274 may be used to control operation of the articulation system 1700. For example, the control button 272 may be used to initiate articulation of the surgical end effector 1500 about the articulation axis AA to the right (arrow "R" in FIG. 1). Upon actuation of the first control button 272, the control system or CPU 224 activates the shifter solenoid 260 of the rotary drive selector system 240 to move the shifter gear 250 into meshing engagement with the second driven gear 326 on the second drive socket 322. Thereafter, the control system 224 or CPU actuates the motor 200 to apply rotary motion to the second rotary drive system 320 in the rotary direction necessary to cause the articulation system 1700 to articulate the surgical end effector to the right (arrow R). In one arrangement, the amount of depression or actuation force applied to the control button, may dictate the speed at which the motor rotates. In addition, or in the alterative, the clinician may also depress the rocker switch 206 to affect the motor rotation speed. Once the surgical end effector 1500 has been articulated to the desired position, the user discontinues actuation of the first control button 270 (and the rocker switch 206). Once the control button 270 has been deactivated, the control system or CPU 224 deactivates the shifter solenoid 260. The spring component of the shifter solenoid 260 moves the shifter gear 250 into meshing engagement with the first driven gear 306 on the first drive socket 302. Thus, further actuation of the motor 200 will result in actuation of the first rotary drive 300. Actuation of the second control button 274 will operate in the same manner, but will result in rotation of the motor 200 so as to cause the articulation system 1700 to articulate the surgical end effector 1500 to the left (arrow L in FIG. 1).

As was discussed above, the surgical end effector 1500 may also be rotated about the shaft axis relative to the articulation joint 1702. To commence rotation of the surgical end effector 1500, the clinician rotates the remote rotational dial 1340 in the rotary direction in which he or she intends the surgical end effector 1500 to rotate. Rotation of the remote rotation dial 1340 causes the control system or CPU 224 to actuate the third axial drive system 400. In particular, the solenoid 402 is actuated to axially move the third drive actuator member 410 and the locking control rod 1302 in the proximal direction. As the locking control rod 1302 moves proximally, the gear rack 1308 causes the locking gear assembly 1430 to rotate the lock gear 1330 so as to disengage the lock lug 1332 from the corresponding lock detent 1328 in the rotation locking disc 1320. See FIGS. 41 and 42. The control system or CPU retains the solenoid 402 in that actuated orientation and then activates the motor 200 to apply rotary motion to the first rotary drive system 300 in the direction necessary to rotate the surgical end effector 1500 in the desired rotary direction. Actuation of the first rotary drive system 300 will result in rotation of the distal drive shaft 1130 which will result in rotation of the surgical end effector 1500 about the shaft axis SA. Once the surgical end effector 1500 has been rotated to the desired position, rotation of the remote rotation dial 1340 by the clinician is discontinued. Thereafter, the control system or CPU 224 will deactivate the motor 200 as well as the solenoid 402. The spring component of the solenoid 402 will then bias the third drive actuator member 410 and the locking control rod 1302 in the distal position to thereby cause the lock gear 1330 to rotate in an opposite direction so as to cause the lock lug 1332 to engage the corresponding lock detent 1328 in the rotation locking disc 1320. The surgical end effector 1500 is locked in that rotary position.

In at least one arrangement, the third buttons 276 may comprise a "home state" button that communicates with the control system or CPU 224 to return the surgical end effector 1500 to a home state wherein the surgical end effector is unarticulated and also rotated back to an in initial rotary orientation. For example, when the third button 276 is actuated, the CPU may unlock the end effector rotary locking system 1310 by actuating the solenoid 402 to cause the lock lug 1332 to disengage from the rotation locking disc 1320 and then actuate the first rotary drive system 300 to cause the surgical end effector to rotate back to a starting rotary position. Thereafter, the solenoid 402 is de-actuated to cause the lock lug 1332 to re-engage the rotation locking disc to lock the surgical end effector 1500 in that rotary orientation. The control system or CPU 224 may then actuate the shifter solenoid 260 to bring the shifter gear 250 into meshing engagement with the second driven gear 326 on the second drive socket 322. After the second rotary drive system 320 is ready for actuation, the control system or CPU 224 may then actuate the motor 200 to return the surgical end effector 1500 to the unarticulated position.

Once the surgical end effector 1500 has been rotated and/or articulated into a desired configuration, discontinuing actuation of the articulation system 1700 as well discontinuing rotation of the remote rotation dial 1340 will result in the motor 200 being operably engaged with the first rotary drive system 300 in the manner discussed herein. The clinician may then manipulate the surgical end effector 1500 so as to position the target tissue between the anvil assembly 1560 and the surgical staple cartridge 1550. The clinician may commence the closing and firing processes by actuating the rocker switch 206. Actuation of the rocker switch 206 will cause the control system or CPU 224 to actuate the motor 200 to cause the motor to apply a rotary control motion in a first rotary direction to the first rotary drive system 300. Rotation of the first rotary drive system 300 will cause the distal power shaft 1130 to rotate and commence the closing process in the manner described above. Once the anvil assembly 1560 is fully closed, the control system or CPU 224 may stop the motor 200 and provide the clinician with an indication (sound, vibration, notice on a display screen, etc.) that the anvil is fully closed. This may happen regardless of whether the rocker switch 206 remains actuated or not. Then, when the clinician desires for the firing member to cut the target tissue which was stapled during the closing process, the clinician may then re-actuate the rocker switch 206 to start the motor and cause the firing member to be distally driven through the end effector in the above-described manner. The rocker switch 206 may be configured such that the speed in which the motor rotates is proportional to the distance that the rocker switch is depressed or otherwise actuated. In other arrangements, the control system or CPU 224 may not stop the motor between the closure and firing sequences. Various forms of sensors and/or encoders may be employed to monitor the position of the firing member during the firing process. Once the firing member has reach the ending position, the rotary direction of the motor is reversed by the control system or CPU 224 until the firing member as returned to the starting position wherein the anvil assembly 1560 is biased to the open position in the above described manner.

FIGS. 40A and 40B illustrate one example arrangement for supplying electrical signals from the circuit board 1060 in the tool attachment module portion 1010 to the end effector attached thereto while enabling the end effector to be selectively articulated and rotated in the various manners described herein. As can be seen in those Figures, conductors (wires) 1401A, 1401B extend along the exterior of the outer spine tube 1402 of the elongate shaft assembly. The conductors 1401A, 1401B extend from the tool attachment module 1010 along the spine tube 1402 and enter a hole 1531 in the channel mounting fixture 1530. To accommodate articulation of the end effector about the articulation joint 1702, a loop 1403 may be provided in the conductors 1401A, 1401B to provide a sufficient amount of slack therein. Conductor 1401A extends into the channel mounting fixture 1530 and has a proximally-facing contact 1405A attached thereto. Similarly, conductor 1401B extends into the channel mounting fixture 1530 and has a proximally-facing contact 1405B attached thereto. These contacts 1405A, 1405B correspond to conductive tracks 1325A, 1325B, respectively that are mounted on the distal surface 1323 of the disc-like body 1322 of the rotation locking disc 1320. When assembled together, contact 1405A is in rotational electrical contact with track 1325A and contact 1405B is in rotational electrical contact with track 1325B. Such arrangement permits relative rotation of the channel mounting fixture 1530 and the rotation locking disc 1320 while facilitating electrical contact between the conductors 1401A, 1401B and the tracks 1325A, 1325B. End effector wires 1327A, 1327B are attached to the tracks 1325A, 1325B, respectively and extend through the hollow mounting stem 1324 of the rotation locking disc 1320. The end effector wires 1327A, 1327B may then be attached to sensors, lights, etc. in the end effector. Such arrangement serves to supply electrical power to the end effector from the tool attachment module 1010 while facilitating articulation and rotation of the end effector.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Paten Application Publication No. 2012/0298719, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES; now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;
U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Paten Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Paten Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility.

A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a housing assembly;
   a motor assembly operably supported in said housing assembly;
   at least one rotary drive system comprising:
      a system drive shaft rotatably supported by said housing assembly;
      a driven bevel gear axially movable on said system drive shaft between a first position wherein said driven bevel gear is in meshing engagement with a driver bevel gear of said motor assembly and a second position wherein said driven bevel gear is out of meshing engagement with said driver bevel gear; and
      a drive system biasing member for biasing said driven bevel gear into said second position; and
   a bailout system comprising:
      a bailout drive train supported by said housing assembly and configured for selective operable engagement and disengagement with said at least one rotary drive system; and
      a bailout handle assembly selectively movable between a stored position within said housing assembly and an actuation position such that, when said bailout handle assembly is in said stored position, said at least one rotary drive system is retained in operable engagement with said motor assembly and when said bailout handle assembly is in said actuation position, said bailout drive train is in operable engagement with said at least one rotary drive system, and wherein said housing assembly further comprises a bailout access panel that is maneuverable between a closed position wherein said bailout handle assembly is completely enclosed within said housing assembly in said stored position and an open position wherein said bailout handle assembly is actuatable such that a portion of said bailout access panel is configured to bias said driven bevel gear into said first position when said bailout access panel is in said closed position.

2. The surgical instrument of claim 1, wherein when said bailout access panel is in said closed position, said bailout access panel positively retains said at least one rotary drive system in operable engagement with said motor assembly and prevents said bailout drive train from operable engagement with said motor assembly.

3. The surgical instrument of claim 1, wherein said bailout access panel is removably attachable to said housing assembly.

4. The surgical instrument of claim 1, wherein said bailout drive train comprises:
a bailout drive shaft operably interfacing with said bailout handle assembly such that manual actuation of said bailout handle assembly applies rotary motion to said bailout drive shaft;
a bailout driven gear on said system drive shaft;
a bailout drive gear axially movable on said bailout drive shaft between an unactuated position wherein said bailout drive gear is not in meshing engagement with said bailout driven gear and an actuated position wherein said bailout drive gear is in meshing engagement with said bailout driven gear; and
a bailout biasing member configured to bias said bailout drive gear into meshing engagement with said bailout driven gear when said bailout access panel is in said open position.

5. The surgical instrument of claim 4, wherein said bailout access panel is configured to bias said bailout drive gear out of meshing engagement with said bailout driven gear when said bailout access panel is in said open position.

6. The surgical instrument of claim 1, further comprising a bailout handle biasing member for biasing said bailout handle assembly to said actuation position when said bailout access panel is in said open position.

7. The surgical instrument of claim 6, wherein said bailout handle assembly is configured to apply rotary motions to a bailout drive shaft upon application of manually-generated ratcheting motions thereto.

8. A surgical instrument, comprising:
a housing assembly;
a motor assembly operably supported within a portion of said housing assembly;
at least one rotary drive system supported by said housing assembly and configured for selective operable engagement and disengagement with said motor assembly;
an access panel interfacing with said housing assembly and being maneuverable between an open position and a closed position, said access panel operably interfacing with said at least one rotary drive system to positively retain said at least one rotary drive system in operable engagement with said motor assembly when said access panel is in said closed position; and
means for disengaging said at least one rotary drive system from said motor assembly and manually applying a rotary motion to said at least one rotary drive system upon manipulation thereof when said access panel has been maneuvered to said open position.

9. A surgical instrument, comprising:
a handle assembly configured for operable attachment to a surgical tool assembly, a portion of said handle assembly being maneuverable between an open position and a closed position;
a motor assembly operably supported by said handle assembly;
at least one rotary drive system operably supported by said handle assembly and being configured for selective operable engagement and disengagement with said motor assembly; and
a bailout system, comprising:
a bailout drive train supported by said handle assembly and configured for selective operable engagement and disengagement with said at least one rotary drive system;
a bailout actuator assembly selectively movable between a stored position within said handle assembly and an actuation position such that, when said bailout actuator assembly is in said stored position, said at least one rotary drive system is retained in operable engagement with said motor assembly and when said bailout actuator assembly is in said actuation position, said bailout drive train is in operable engagement with said at least one rotary drive system; and
an actuator biaser configured to bias said bailout actuator assembly from said stored position to said actuation position when said portion of said handle assembly is maneuvered into said open position.

10. The surgical instrument of claim 9, wherein said portion of said handle assembly comprises a bailout access panel that is maneuverable between said closed position and said open position, wherein said bailout actuator assembly is completely enclosed within said handle assembly in said stored position when said bailout access panel is in said closed position, wherein said bailout actuator assembly is in said actuation position when said bailout access panel is in said open position, and wherein said bailout actuator assembly is manually actuatable when said bailout actuator assembly is in said actuation position.

11. The surgical instrument of claim 10, wherein said bailout access panel is removably attachable to said handle assembly.

12. The surgical instrument of claim 10, wherein when said bailout access panel is in said closed position, said bailout access panel positively retains said at least one rotary drive system in operable engagement with said motor assembly and prevents said bailout drive train from operably engaging said motor assembly.

13. The surgical instrument of claim 10, wherein said at least one rotary drive system comprises:
a system drive shaft rotatably supported by said handle assembly;
a driven bevel gear axially movable on said system drive shaft between a first position wherein said driven bevel gear is in meshing engagement with a driver bevel gear of said motor assembly and a second position wherein said driven bevel gear is out of meshing engagement with said driver bevel gear; and
a drive system biasing member for biasing said driven bevel gear into said second position and wherein a portion of said bailout access panel is configured to bias said driven bevel gear into said first position when said bailout access panel is in said closed position.

14. The surgical instrument of claim 13, wherein said bailout drive train comprises:
a bailout drive shaft operably interfacing with said bailout actuator assembly such that manual actuation of said bailout actuator assembly will apply rotary motion to said bailout drive shaft;
a bailout driven gear on said system drive shaft;
a bailout drive gear axially movable on said bailout drive shaft between an unactuated position wherein said bailout drive gear is not in meshing engagement with said bailout driven gear and an actuated position wherein said bailout drive gear is in meshing engagement with said bailout driven gear; and a bailout biasing member configured to bias said bailout drive gear into meshing engagement with said bailout driven gear when said bailout access panel is in said open position.

15. The surgical instrument of claim 14, wherein said bailout access panel is configured to bias said bailout drive gear out of meshing engagement with said bailout driven gear when said bailout access panel is in said open position.

16. The surgical instrument of claim 10, wherein said bailout actuator assembly is configured to apply rotary motions to a bailout drive shaft upon application of manually-generated ratcheting motions thereto.

17. The surgical instrument of claim 10, wherein said at least one rotary drive system comprises:
 a system drive shaft rotatably supported by said handle assembly;
 a driven bevel gear axially movable on said system drive shaft between a first position wherein said driven bevel gear is in meshing engagement with a driver bevel gear of said motor assembly and a second position wherein said driven bevel gear is out of meshing engagement with said driver bevel gear;
 a drive system biasing member for biasing said driven bevel gear into said second position, wherein a portion of said bailout access panel is configured to bias said driven bevel gear into said first position when said bailout access panel is in said closed position;
 a first rotary drive system configured to apply first rotary drive motions to the surgical tool assembly coupled to said handle assembly;
 a second rotary drive system configured to apply second rotary drive motions to the surgical tool assembly coupled to said handle assembly; and
 a rotary drive selector system operably interfacing with said system drive shaft for selectively operably engaging said first and second rotary drive systems to said system drive shaft.

18. The surgical instrument of claim 10, wherein said bailout actuator assembly comprises a bailout lever pivotally supported by said handle assembly for pivotal travel between said stored position and said actuation position.

* * * * *